US012559750B2

(12) United States Patent
Drygin et al.

(10) Patent No.: US 12,559,750 B2
(45) **Date of Patent: *Feb. 24, 2026**

(54) METHODS AND COMPOSITIONS FOR TREATMENT OF POLYCYSTIC KIDNEY DISEASE

(71) Applicant: Regulus Therapeutics Inc., San Diego, CA (US)

(72) Inventors: Denis Drygin, San Diego, CA (US); Garth A. Kinberger, San Diego, CA (US); Edmund Chun Yu Lee, San Diego, CA (US)

(73) Assignee: Regulus Therapeutics Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/052,052

(22) Filed: Feb. 12, 2025

(65) Prior Publication Data

US 2025/0188466 A1 Jun. 12, 2025

Related U.S. Application Data

(63) Continuation of application No. 18/610,891, filed on Mar. 20, 2024, which is a continuation of application No. PCT/US2022/077766, filed on Oct. 7, 2022.

(60) Provisional application No. 63/253,933, filed on Oct. 8, 2021.

(51) Int. Cl.
*C12N 15/113* (2010.01)
*A61P 13/12* (2006.01)

(52) U.S. Cl.
CPC ............ *C12N 15/113* (2013.01); *A61P 13/12* (2018.01); *C12N 2310/113* (2013.01); *C12N 2310/315* (2013.01); *C12N 2310/321* (2013.01); *C12N 2310/322* (2013.01); *C12N 2310/3341* (2013.01)

(58) Field of Classification Search
CPC ............ C12N 15/113; C12N 2310/113; C12N 2310/315; C12N 2310/321; C12N 2310/322; C12N 2310/3341; C12N 2310/3231; C12N 2310/333; C12N 2310/336; A61P 13/12; A61K 31/7088
See application file for complete search history.

(56) References Cited

U.S. PATENT DOCUMENTS

| | | | |
|---|---|---|---|
| 7,683,036 B2 | 3/2010 | Esau et al. | |
| 10,633,657 B2 | 4/2020 | Androsavich et al. | |
| 11,168,325 B2 | 11/2021 | Androsavich et al. | |
| 2008/0280940 A1 | 11/2008 | Farber et al. | |
| 2009/0143326 A1 | 6/2009 | Obad et al. | |
| 2010/0267814 A1* | 10/2010 | Bennett | A61P 35/04 514/44 R |
| 2012/0088902 A1 | 4/2012 | Currie et al. | |
| 2012/0115917 A1 | 5/2012 | Toler et al. | |
| 2013/0236453 A1 | 9/2013 | Croce et al. | |
| 2020/0392503 A1 | 12/2020 | Allerson et al. | |
| 2022/0025372 A1 | 1/2022 | Androsavich et al. | |
| 2022/0380767 A1 | 12/2022 | Allerson et al. | |
| 2023/0109466 A1 | 4/2023 | Allerson | |
| 2024/0141350 A1 | 5/2024 | Allerson et al. | |

FOREIGN PATENT DOCUMENTS

| | | | |
|---|---|---|---|
| CN | 101300008 | A | 11/2008 |
| EP | 1777301 | A2 | 4/2007 |
| JP | 2007529459 | A | 10/2007 |
| WO | 2005089731 | A2 | 9/2005 |
| WO | 2005103298 | A2 | 11/2005 |
| WO | 2006020768 | A2 | 2/2006 |
| WO | 2007112753 | A2 | 10/2007 |
| WO | 2007126150 | A1 | 11/2007 |
| WO | 2008042973 | A2 | 4/2008 |
| WO | 2008091703 | A2 | 7/2008 |
| WO | 2008131191 | A2 | 10/2008 |
| WO | 2008151639 | A2 | 12/2008 |
| WO | 2009043353 | A2 | 4/2009 |
| WO | 2009109665 | A1 | 9/2009 |
| WO | 2011060100 | A1 | 5/2011 |
| WO | 2013165320 | A1 | 11/2013 |
| WO | 2014179446 | A2 | 11/2014 |
| WO | 2015061684 | A1 | 4/2015 |
| WO | 2015123449 | A2 | 8/2015 |
| WO | 2017035319 | A1 | 3/2017 |
| WO | 2018047148 | A1 | 3/2018 |
| WO | 2018106566 | A1 | 6/2018 |
| WO | 2018106568 | A1 | 6/2018 |
| WO | 2021153762 | A1 | 8/2021 |
| WO | 2023060237 | A1 | 4/2023 |
| WO | 2023060238 | A2 | 4/2023 |
| WO | 2024215846 | A1 | 10/2024 |

OTHER PUBLICATIONS

Abraham et al., "Nucleobase analogs for degenerate hybridization devised through conformational pairing analysis", Biotechniques 43(5):617-624 (2007).
Anonymous "Securities and Exchange Commission Form 8-K," Retrieved from the internet: http://pdf.secdatabase.com/19/0001193125-21-169262.pdf, pp. 1-34 (2021).
Carney, "MicroRNA-17: A New Drug Target for ADPKD," Nature Reviews Nephrology, Mar. 6, 2017, 1 page.
Davis et al., "Improved targeting of miRNA with antisense oligonucleotides," Nucleic Acids Res. 34(8):2294-304 (2006).
Hajarnis et al., "Chapter 13: MicroRNAs and Polycystic Kidney Disease," Brisbane: Codon Publications, Nov. 2015, 13 pages.
Hajarnis et al., "MicroRNA-17 Family Promotes Polycystic Kidney Disease Progression Through Modulation of Mitochondrial Metabolism," Nature Communications, 2017, 8:1-14.

(Continued)

*Primary Examiner* — Kimberly Chong
(74) *Attorney, Agent, or Firm* — McNeill PLLC

(57) ABSTRACT

Provided herein are methods for the treatment of polycystic kidney disease, including autosomal dominant polycystic kidney disease, using modified oligonucleotides targeted to miR-17.

15 Claims, 7 Drawing Sheets

Specification includes a Sequence Listing.

(56) References Cited

OTHER PUBLICATIONS

International Search Report and Written Opinion issued in International Application No. PCT/US2022/077766, mailed Feb. 6, 2023, 14 pages.
International Search Report and Written Opinion issued in International Application No. PCT/US2022/077767, mailed Mar. 27, 2023, 25 pages.
International Search Report and Written Opinion issued in International Application No. PCT/US2024/024006, mailed Jun. 27, 2024, 19 pages.
International Search Report and Written Opinion issued in International Application No. PCT/US2017/064432, dated Apr. 4, 2018, 20 pages.
International Search Report and Written Opinion of the International Searching Authority in International Application No. PCT/US2017/064428, dated Mar. 26, 2018, 17 pages.
International Search Report and Written Opinion issued in International Application No. PCT/US2016/048603, dated Nov. 30, 2016, 17 pages.
Kamiya et al., "Introduction of 2,6-Diaminopurines into Serinol Nucleic Acid Improves Anti-miRNA Performance," ChemBioChem 18(19):1917-1922 (2017).
Koizumi, "Nucleic Acids Therapeutics Using Chemical Modified Oligonucleotides," Medchem News, 2015, 25(2):103-108.
Kurschat et al., "An Approach to Cystic Kidney Diseases: the Clinician's View," Nature Reviews, 2014, 10:687-699.
Lakhia et al., "MicroRNA-21 Aggravates Cyst Growth in a Model of Polycystic Kidney Disease," J Am Soc Nephrol, 2015, 27:1-12.
Lee et al., "Discovery and preclinical evaluation of anti-miR-17 oligonucleotide RGLS4326 for the treatment of polycystic kidney disease," Nature Communications 10(1)1-14 (2019).
Lee et al., "Discovery of Next-generation Anti-miR-17 Oligonucleotide RGLS8429 for Treatment of Autosomal Dominant Polycystic Kidney Disease (ADPKD)," Regulus presentation, 1 page (2022).
Lee, "Discovery of Next-generation Anti-miR-17 Oligonucleotide RGLS8429 for Treatment of ADPKD," Regulus presentation, Federation of American Society of Experimental Biology (FASEB), The Polycystic Kidney Disease Conference: Hurdles and Advances in Molecular Mechanisms and Therapies, 14 pages (2022).
Liu et al., "2-aminopurine probe in combination with catalyzed hairpin assembly signal amplification for simple and sensitive detection of microRNA", Talanta, Elsevier vol. 174, pp. 336-340 (2017), Abstract Only, 1 page.
Matsubara et al., "Apoptosis Induction by Antisense Oligonucleotides Against miR-17-5p and miR-20a in Lung Cancers Overexpressing miR-17-92," Oncogene, 2007, 26(41):6099-6105.
Murphy et al., "Silencing of the miR-17 92 Cluster Family Inhibits Medulloblastoma Progression," Cancer Research 73(23):7068-7078 (2013).
NIH Grant 1R01DK102572-01A1, "MicroRNAs: New Regulators of Disease Progression in Polycystic Kidney Disease," Awarded May 11, 2015, downloaded Feb. 20, 2018, 2 pages.
NIH Grant 1R03DK099568-01, "Mirna Based Therapeutics in Polycystic Kidney Disease," Awarded Jul. 19, 2013, downloaded Feb. 20, 2018, 2 pages.
NIH Grant 5R01DK102572-02, "MicroRNAs: New Regulators of Disease Progression in Polycystic Kidney Disease," Awarded May 2, 2016, downloaded Feb. 20, 2018, 2 pages.
NIH Grant 5R01DK102572-03, "MicroRNAs: New Regulators of Disease Progression in Polycystic Kidney Disease," Awarded May 1, 2017, downloaded Feb. 20, 2018, 2 pages.
NIH Grant 5R03DK099568-02, "Mirna-Based Therapeutics in Polycystic Kidney Disease," Awarded Jun. 14, 2014, downloaded Feb. 20, 2018, 2 pages.
Noureddine, et al., "MicroRNAs and Polycystic Kidney Disease," Drug Discovery Today, Disease Models, 2013, 10(3):e137-e143.
Patel et al., "Inactivation of miR-17~92 Suppresses Cyst Growth in Genetic Models of ADPKD," Presentation, Kidney Week, Oct. 2014, 17 pages.
Patel et al., "miR-17~92 miRNA Cluster Promotes Kidney Cyst Growth in Polycystic Kidney Disease," PNAS, 2013, 110(26):10765-10770.
Presentation by Lee, "Discovery of the next-generation anti-miR-17 oligonucleotide RGLS8429 for treatment of ADPKD," Regulus R&D Day, 11 pages (2023).
Serva et al., "miR-17-5p Regulates Endocytic Trafficking Through Targeting TBC1D2/Armus," PLOS One, 2012, 7(12): e52555, 1-15.
Seth et al., "Short Antisense Oligonucleotides with Novel 2'-4' Conformationaly Restricted Nucleoside Analogues Show Improved Potency without Increased Toxicity in Animals," J. Med. Chem. 52:10-13 (2009).
Stenvang et al., "Inhibition of microRNA function by antimiR oligonucleotides," Silence 3(1): 1-17 (2012).
Sun et al., "MicroRNA-17 Post-Transcriptionally Regulates Polycystic Kidney Disease-2 Gene and Promotes Cell Proliferation," Mol Biol Rep, 2010, 37(6):2951-2958.
Tran et al., "The RNA-Binding Protein Bicaudal C Regulates Polycystin 2 in the Kidney by Antagonizing miR-17 Activity," Development, 2010, 137(7):1107-1116.
Yheskel et al., "Anti-microRNA screen uncovers miR-17 family within miR-17~92 cluster as the primary driver of kidney cyst growth," Scientific Reports 9:1920, 11 pages (2019).
Yheskel et al., "Therapeutic microRNAs in Polycystic Kidney Disease," Current Opin Nephrol Hypertens, 2017, 26: 1-8.
U.S. Appl. No. 19/019,923, filed Jan. 14, 2025.
U.S. Appl. No. 18/693,783, filed Mar. 20, 2024.
Regulus press release entitled "Regulus Therapeutics Announces Strategic Prioritization of RGLS8429, its Next-Generation Candidate for the Treatment of Autosomal Dominate Polycystic Kidney Disease," Oct. 12, 2021, 3 pages.
Valencia et al., "Deciphering and overcoming off-target AMPAR inhibition of anti-miR oligonucleotide RGLS4326," poster presented at the 2024 meeting of the Oligonucleotide Therapeutics Society (Oct. 6-9, 2024).

* cited by examiner

Guanosine
G

Inosine
I

2-Aminopurine
AP

Purine numbering 2,6-Diaminopurine
DAP

IsoGuanosine
IsoG

Adenosine
A

SEQUENCE LISTING

```
Sequence total quantity: 30
SEQ ID NO: 1          moltype = RNA  length = 23
FEATURE               Location/Qualifiers
misc_feature          1..23
                      note = Synthetic: miR-17
source                1..23
                      mol_type = other RNA
                      organism = synthetic construct
SEQUENCE: 1
caaagtgctt acagtgcagg tag                                          23

SEQ ID NO: 2          moltype = RNA  length = 23
FEATURE               Location/Qualifiers
misc_feature          1..23
                      note = Synthetic: miR-20a
source                1..23
                      mol_type = other RNA
                      organism = synthetic construct
SEQUENCE: 2
taaagtgctt atagtgcagg tag                                          23

SEQ ID NO: 3          moltype = RNA  length = 23
FEATURE               Location/Qualifiers
misc_feature          1..23
                      note = Synthetic: miR-20b
source                1..23
                      mol_type = other RNA
                      organism = synthetic construct
SEQUENCE: 3
caaagtgctc atagtgcagg tag                                          23

SEQ ID NO: 4          moltype = RNA  length = 23
```

```
FEATURE               Location/Qualifiers
misc_feature          1..23
                      note = Synthetic: miR-93
source                1..23
                      mol_type = other RNA
                      organism = synthetic construct
SEQUENCE: 4
caaagtgctg ttcgtgcagg tag                                          23

SEQ ID NO: 5          moltype = RNA  length = 23
FEATURE               Location/Qualifiers
misc_feature          1..23
                      note = Synthetic: miR-106a
source                1..23
                      mol_type = other RNA
                      organism = synthetic construct
SEQUENCE: 5
aaaagtgctt acagtgcagg tag                                          23

SEQ ID NO: 6          moltype = RNA  length = 21
FEATURE               Location/Qualifiers
misc_feature          1..21
                      note = Synthetic: miR-106b
source                1..21
                      mol_type = other RNA
                      organism = synthetic construct
SEQUENCE: 6
taaagtgctg acagtgcaga t                                            21

SEQ ID NO: 7          moltype = RNA  length = 14
FEATURE               Location/Qualifiers
misc_feature          1..14
                      note = Synthetic: nucleobase sequence
source                1..14
                      mol_type = other RNA
                      organism = synthetic construct
SEQUENCE: 7
ctacctgcac tgta                                                    14

SEQ ID NO: 8          moltype = RNA  length = 13
FEATURE               Location/Qualifiers
misc_feature          1..13
                      note = Synthetic: nucleobase sequence
source                1..13
                      mol_type = other RNA
                      organism = synthetic construct
SEQUENCE: 8
ctacctgcac tgt                                                     13

SEQ ID NO: 9          moltype = RNA  length = 12
FEATURE               Location/Qualifiers
misc_feature          1..12
                      note = Synthetic: nucleobase sequence
source                1..12
                      mol_type = other RNA
                      organism = synthetic construct
SEQUENCE: 9
ctacctgcac tg                                                      12

SEQ ID NO: 10         moltype = RNA  length = 11
FEATURE               Location/Qualifiers
misc_feature          1..11
                      note = Synthetic: nucleobase sequence
source                1..11
                      mol_type = other RNA
                      organism = synthetic construct
SEQUENCE: 10
ctacctgcac t                                                       11

SEQ ID NO: 11         moltype = RNA  length = 10
FEATURE               Location/Qualifiers
misc_feature          1..10
                      note = Synthetic: nucleobase sequence
source                1..10
                      mol_type = other RNA
                      organism = synthetic construct
SEQUENCE: 11
ctacctgcac                                                         10
```

-continued

```
SEQ ID NO: 12           moltype = RNA  length = 11
FEATURE                 Location/Qualifiers
misc_feature            1..11
                        note = Synthetic: RG-NG-1004
modified_base           1..11
                        mod_base = OTHER
                        note = S-constrained ethyl nucleoside
source                  1..11
                        mol_type = other RNA
                        organism = synthetic construct
SEQUENCE: 12
taagcacttt g                                                      11

SEQ ID NO: 13           moltype = RNA  length = 11
FEATURE                 Location/Qualifiers
misc_feature            1..11
                        note = Synthetic: RG-NG-1005
modified_base           1..2
                        mod_base = OTHER
                        note = S-constrained ethyl nucleoside
modified_base           3
                        mod_base = OTHER
                        note = 2'-O-methyl nucleoside
modified_base           5..7
                        mod_base = OTHER
                        note = S-constrained ethyl nucleoside
modified_base           8..9
                        mod_base = OTHER
                        note = 2'-O-methyl nucleoside
modified_base           10..11
                        mod_base = OTHER
                        note = S-constrained ethyl nucleoside
source                  1..11
                        mol_type = other RNA
                        organism = synthetic construct
SEQUENCE: 13
taagcacttt g                                                      11

SEQ ID NO: 14           moltype = RNA  length = 15
FEATURE                 Location/Qualifiers
modified_base           3
                        mod_base = OTHER
                        note = thymine
modified_base           5
                        mod_base = OTHER
                        note = thymine
misc_feature            1..15
                        note = Synthetic: RG-NG-1018
modified_base           1..3
                        mod_base = OTHER
                        note = 2'-O-methoxyethyl nucleoside
modified_base           4
                        mod_base = OTHER
                        note = S-constrained ethyl nucleoside
modified_base           5
                        mod_base = OTHER
                        note = 2'-O-methoxyethyl nucleoside
modified_base           7..8
                        mod_base = OTHER
                        note = S-constrained ethyl nucleoside
modified_base           9
                        mod_base = OTHER
                        note = 2'-O-methyl nucleoside
modified_base           10..12
                        mod_base = OTHER
                        note = 2'-fluoro nucleoside
modified_base           13
                        mod_base = OTHER
                        note = 2'-O-methyl nucleoside
modified_base           14..15
                        mod_base = OTHER
                        note = S-constrained ethyl nucleoside
source                  1..15
                        mol_type = other RNA
                        organism = synthetic construct
SEQUENCE: 14
actgtaagca ctttc                                                  15

SEQ ID NO: 15           moltype = RNA  length = 15
```

-continued

```
FEATURE                 Location/Qualifiers
modified_base           3
                        mod_base = OTHER
                        note = thymine
misc_feature            1..15
                        note = Synthetic: RG-NG-1019
modified_base           1..2
                        mod_base = OTHER
                        note = S-constrained ethyl nucleoside
modified_base           4..5
                        mod_base = OTHER
                        note = S-constrained ethyl nucleoside
modified_base           7..8
                        mod_base = OTHER
                        note = S-constrained ethyl nucleoside
modified_base           9
                        mod_base = OTHER
                        note = 2'-O-methyl nucleoside
modified_base           10..12
                        mod_base = OTHER
                        note = 2'-fluoro nucleoside
modified_base           13
                        mod_base = OTHER
                        note = 2'-O-methyl nucleoside
modified_base           14..15
                        mod_base = OTHER
                        note = S-constrained ethyl nucleoside
source                  1..15
                        mol_type = other RNA
                        organism = synthetic construct
SEQUENCE: 15
actgtaagca ctttc                                                            15

SEQ ID NO: 16           moltype = RNA  length = 13
FEATURE                 Location/Qualifiers
modified_base           1
                        mod_base = OTHER
                        note = thymine
modified_base           3
                        mod_base = OTHER
                        note = thymine
misc_feature            1..13
                        note = Synthetic: RG-NG-1020
modified_base           1
                        mod_base = OTHER
                        note = 2'-O-methoxyethyl nucleoside
modified_base           2
                        mod_base = OTHER
                        note = S-constrained ethyl nucleoside
modified_base           3
                        mod_base = OTHER
                        note = 2'-O-methoxyethyl nucleoside
modified_base           5..6
                        mod_base = OTHER
                        note = S-constrained ethyl nucleoside
modified_base           7
                        mod_base = OTHER
                        note = 2'-O-methyl nucleoside
modified_base           8..10
                        mod_base = OTHER
                        note = 2'-fluoro nucleoside
modified_base           11
                        mod_base = OTHER
                        note = 2'-O-methyl nucleoside
modified_base           12..13
                        mod_base = OTHER
                        note = S-constrained ethyl nucleoside
source                  1..13
                        mol_type = other RNA
                        organism = synthetic construct
SEQUENCE: 16
tgtaagcact ttc                                                              13

SEQ ID NO: 17           moltype = RNA  length = 11
FEATURE                 Location/Qualifiers
modified_base           1
                        mod_base = OTHER
                        note = thymine
misc_feature            1..11
```

```
                        note = Synthetic: RG-NG-1021
modified_base           1
                        mod_base = OTHER
                        note = 2'-O-methoxyethyl nucleoside
modified_base           3..4
                        mod_base = OTHER
                        note = S-constrained ethyl nucleoside
modified_base           5
                        mod_base = OTHER
                        note = 2'-O-methyl nucleoside
modified_base           6..8
                        mod_base = OTHER
                        note = 2'-fluoro nucleoside
modified_base           9
                        mod_base = OTHER
                        note = 2'-O-methyl nucleoside
modified_base           10..11
                        mod_base = OTHER
                        note = S-constrained ethyl nucleoside
source                  1..11
                        mol_type = other RNA
                        organism = synthetic construct
SEQUENCE: 17
taagcacttt c                                                      11

SEQ ID NO: 18           moltype = RNA  length = 11
FEATURE                 Location/Qualifiers
modified_base           1
                        mod_base = OTHER
                        note = thymine
misc_feature            1..11
                        note = Synthetic: RG-NG-1022
modified_base           1..2
                        mod_base = OTHER
                        note = 2'-O-methoxyethyl nucleoside
modified_base           3..4
                        mod_base = OTHER
                        note = S-constrained ethyl nucleoside
modified_base           5
                        mod_base = OTHER
                        note = 2'-O-methyl nucleoside
modified_base           6..8
                        mod_base = OTHER
                        note = 2'-fluoro nucleoside
modified_base           9
                        mod_base = OTHER
                        note = 2'-O-methyl nucleoside
modified_base           10..11
                        mod_base = OTHER
                        note = S-constrained ethyl nucleoside
source                  1..11
                        mol_type = other RNA
                        organism = synthetic construct
SEQUENCE: 18
taagcacttt c                                                      11

SEQ ID NO: 19           moltype = RNA  length = 10
FEATURE                 Location/Qualifiers
modified_base           8
                        mod_base = OTHER
                        note = thymine
misc_feature            1..10
                        note = Synthetic: RG-NG-1030
modified_base           1..2
                        mod_base = OTHER
                        note = 2'-O-methyl nucleoside
modified_base           3..6
                        mod_base = OTHER
                        note = locked nucleic acid (LNA) nucleoside
modified_base           7
                        mod_base = OTHER
                        note = 2'-O-methyl nucleoside
modified_base           8
                        mod_base = OTHER
                        note = locked nucleic acid (LNA) nucleoside
modified_base           10
                        mod_base = OTHER
                        note = 2'-O-methyl nucleoside
source                  1..10
```

-continued

```
                        mol_type = other RNA
                        organism = synthetic construct
SEQUENCE: 19
aagcactttc                                                  10

SEQ ID NO: 20           moltype = RNA  length = 11
FEATURE                 Location/Qualifiers
misc_feature            1..11
                        note = Synthetic: RG-NG-1004
modified_base           1..11
                        mod_base = OTHER
                        note = S-constrained ethyl nucleoside
source                  1..11
                        mol_type = other RNA
                        organism = synthetic construct
SEQUENCE: 20
taagcacttt g                                                11

SEQ ID NO: 21           moltype = RNA  length = 11
FEATURE                 Location/Qualifiers
misc_feature            1..11
                        note = Synthetic: RG-NG-1005
modified_base           1..2
                        mod_base = OTHER
                        note = S-constrained ethyl nucleoside
modified_base           3
                        mod_base = OTHER
                        note = 2'-O-methyl nucleoside
modified_base           5..7
                        mod_base = OTHER
                        note = S-constrained ethyl nucleoside
modified_base           8..9
                        mod_base = OTHER
                        note = 2'-O-methyl nucleoside
modified_base           10..11
                        mod_base = OTHER
                        note = S-constrained ethyl nucleoside
source                  1..11
                        mol_type = other RNA
                        organism = synthetic construct
SEQUENCE: 21
taagcacttt g                                                11

SEQ ID NO: 22           moltype = RNA  length = 15
FEATURE                 Location/Qualifiers
modified_base           3
                        mod_base = OTHER
                        note = thymine
modified_base           5
                        mod_base = OTHER
                        note = thymine
misc_feature            1..15
                        note = Synthetic: RG-NG-1018
modified_base           1..3
                        mod_base = OTHER
                        note = 2'-O-methoxyethyl nucleoside
modified_base           4
                        mod_base = OTHER
                        note = S-constrained ethyl nucleoside
modified_base           5
                        mod_base = OTHER
                        note = 2'-O-methoxyethyl nucleoside
modified_base           7..8
                        mod_base = OTHER
                        note = S-constrained ethyl nucleoside
modified_base           9
                        mod_base = OTHER
                        note = 2'-O-methyl nucleoside
modified_base           10..12
                        mod_base = OTHER
                        note = 2'-fluoro nucleoside
modified_base           13
                        mod_base = OTHER
                        note = 2'-O-methyl nucleoside
modified_base           14..15
                        mod_base = OTHER
                        note = S-constrained ethyl nucleoside
source                  1..15
                        mol_type = other RNA
```

```
                        organism = synthetic construct
SEQUENCE: 22
actgtaagca ctttc                                                    15

SEQ ID NO: 23           moltype = RNA  length = 15
FEATURE                 Location/Qualifiers
modified_base           3
                        mod_base = OTHER
                        note = thymine
misc_feature            1..15
                        note = Synthetic: RG-NG-1019
modified_base           1..2
                        mod_base = OTHER
                        note = S-constrained ethyl nucleoside
modified_base           4..5
                        mod_base = OTHER
                        note = S-constrained ethyl nucleoside
modified_base           7..8
                        mod_base = OTHER
                        note = S-constrained ethyl nucleoside
modified_base           9
                        mod_base = OTHER
                        note = 2'-O-methyl nucleoside
modified_base           10..12
                        mod_base = OTHER
                        note = 2'-fluoro nucleoside
modified_base           13
                        mod_base = OTHER
                        note = 2'-O-methyl nucleoside
modified_base           14..15
                        mod_base = OTHER
                        note = S-constrained ethyl nucleoside
source                  1..15
                        mol_type = other RNA
                        organism = synthetic construct
SEQUENCE: 23
actgtaagca ctttc                                                    15

SEQ ID NO: 24           moltype = RNA  length = 13
FEATURE                 Location/Qualifiers
modified_base           1
                        mod_base = OTHER
                        note = thymine
modified_base           3
                        mod_base = OTHER
                        note = thymine
misc_feature            1..13
                        note = Synthetic: RG-NG-1020
modified_base           1
                        mod_base = OTHER
                        note = 2'-O-methoxyethyl nucleoside
modified_base           2
                        mod_base = OTHER
                        note = S-constrained ethyl nucleoside
modified_base           3
                        mod_base = OTHER
                        note = 2'-O-methoxyethyl nucleoside
modified_base           5..6
                        mod_base = OTHER
                        note = S-constrained ethyl nucleoside
modified_base           7
                        mod_base = OTHER
                        note = 2'-O-methyl nucleoside
modified_base           8..10
                        mod_base = OTHER
                        note = 2'-fluoro nucleoside
modified_base           11
                        mod_base = OTHER
                        note = 2'-O-methyl nucleoside
modified_base           12..13
                        mod_base = OTHER
                        note = S-constrained ethyl nucleoside
source                  1..13
                        mol_type = other RNA
                        organism = synthetic construct
SEQUENCE: 24
tgtaagcact ttc                                                      13

SEQ ID NO: 25           moltype = RNA  length = 11
```

-continued

```
FEATURE                 Location/Qualifiers
modified_base           1
                        mod_base = OTHER
                        note = thymine
misc_feature            1..11
                        note = Synthetic: RG-NG-1021
modified_base           1
                        mod_base = OTHER
                        note = 2'-O-methoxyethyl nucleoside
modified_base           3..4
                        mod_base = OTHER
                        note = S-constrained ethyl nucleoside
modified_base           5
                        mod_base = OTHER
                        note = 2'-O-methyl nucleoside
modified_base           6..8
                        mod_base = OTHER
                        note = 2'-fluoro nucleoside
modified_base           9
                        mod_base = OTHER
                        note = 2'-O-methyl nucleoside
modified_base           10..11
                        mod_base = OTHER
                        note = S-constrained ethyl nucleoside
source                  1..11
                        mol_type = other RNA
                        organism = synthetic construct
SEQUENCE: 25
taagcacttt c                                                        11

SEQ ID NO: 26           moltype = RNA  length = 11
FEATURE                 Location/Qualifiers
modified_base           1
                        mod_base = OTHER
                        note = thymine
misc_feature            1..11
                        note = Synthetic: RG-NG-1022
modified_base           1..2
                        mod_base = OTHER
                        note = 2'-O-methoxyethyl nucleoside
modified_base           3..4
                        mod_base = OTHER
                        note = S-constrained ethyl nucleoside
modified_base           5
                        mod_base = OTHER
                        note = 2'-O-methyl nucleoside
modified_base           6..8
                        mod_base = OTHER
                        note = 2'-fluoro nucleoside
modified_base           9
                        mod_base = OTHER
                        note = 2'-O-methyl nucleoside
modified_base           10..11
                        mod_base = OTHER
                        note = S-constrained ethyl nucleoside
source                  1..11
                        mol_type = other RNA
                        organism = synthetic construct
SEQUENCE: 26
taagcacttt c                                                        11

SEQ ID NO: 27           moltype = RNA  length = 19
FEATURE                 Location/Qualifiers
modified_base           2
                        mod_base = OTHER
                        note = thymine
modified_base           7
                        mod_base = OTHER
                        note = thymine
modified_base           9
                        mod_base = OTHER
                        note = thymine
misc_feature            1..19
                        note = Synthetic: RG-NG-1040
modified_base           1..2
                        mod_base = OTHER
                        note = 2'-O-methoxyethyl nucleoside
modified_base           3
                        mod_base = OTHER
```

```
                        note = S-constrained ethyl nucleoside
modified_base           4..7
                        mod_base = OTHER
                        note = 2'-O-methoxyethyl nucleoside
modified_base           8
                        mod_base = OTHER
                        note = S-constrained ethyl nucleoside
modified_base           9
                        mod_base = OTHER
                        note = 2'-O-methoxyethyl nucleoside
modified_base           10
                        mod_base = OTHER
                        note = DNA
modified_base           11..12
                        mod_base = OTHER
                        note = S-constrained ethyl nucleoside
modified_base           13
                        mod_base = OTHER
                        note = 2'-O-methyl nucleoside
modified_base           14..16
                        mod_base = OTHER
                        note = 2-fluoro nucleoside
modified_base           17
                        mod_base = OTHER
                        note = 2'-O-methyl nucleoside
modified_base           18..19
                        mod_base = OTHER
                        note = S-constrained ethyl nucleoside
source                  1..19
                        mol_type = other RNA
                        organism = synthetic construct
SEQUENCE: 27
ctgcactgta agcactttg                                                19

SEQ ID NO: 28           moltype = RNA  length = 17
FEATURE                 Location/Qualifiers
modified_base           5
                        mod_base = OTHER
                        note = thymine
modified_base           7
                        mod_base = OTHER
                        note = thymine
misc_feature            1..17
                        note = Synthetic: RG-NG-1032
modified_base           1
                        mod_base = OTHER
                        note = S-constrained ethyl nucleoside
modified_base           2..5
                        mod_base = OTHER
                        note = 2'-O-methoxyethyl nucleoside
modified_base           6
                        mod_base = OTHER
                        note = S-constrained ethyl nucleoside
modified_base           7
                        mod_base = OTHER
                        note = 2'-O-methoxyethyl nucleoside
modified_base           8
                        mod_base = OTHER
                        note = DNA
modified_base           9..10
                        mod_base = OTHER
                        note = S-constrained ethyl nucleoside
modified_base           11
                        mod_base = OTHER
                        note = 2'-O-methyl nucleoside
modified_base           12..14
                        mod_base = OTHER
                        note = 2-fluoro nucleoside
modified_base           15
                        mod_base = OTHER
                        note = 2'-O-methyl nucleoside
```

-continued

```
modified_base           16..17
                        mod_base = OTHER
                        note = S-constrained ethyl nucleoside
source                  1..17
                        mol_type = other RNA
                        organism = synthetic construct
SEQUENCE: 28
gcactgtaag cactttg                                                        17

SEQ ID NO: 29           moltype = RNA  length = 10
FEATURE                 Location/Qualifiers
misc_feature            1..10
                        note = Synthetic: 5'N+1
modified_base           1..3
                        mod_base = OTHER
                        note = S-constrained ethyl nucleoside
modified_base           4
                        mod_base = OTHER
                        note = 2'-O-methyl nucleoside
modified_base           5..7
                        mod_base = OTHER
                        note = 2'-fluoro nucleoside
modified_base           8
                        mod_base = OTHER
                        note = 2'-O-methyl nucleoside
modified_base           9..10
                        mod_base = OTHER
                        note = S-constrained ethyl nucleoside
source                  1..10
                        mol_type = other RNA
                        organism = synthetic construct
SEQUENCE: 29
aagcacttta                                                                10

SEQ ID NO: 30           moltype = RNA  length = 10
FEATURE                 Location/Qualifiers
misc_feature            1..10
                        note = Synthetic: RG-NG-1030
modified_base           1..2
                        mod_base = OTHER
                        note = 2'-O-methyl nucleoside
modified_base           3..6
                        mod_base = OTHER
                        note = locked nucleic acid (LNA) nucleoside
modified_base           7
                        mod_base = OTHER
                        note = 2'-O-methyl nucleoside
modified_base           8
                        mod_base = OTHER
                        note = locked nucleic acid (LNA) nucleoside
modified_base           10
                        mod_base = OTHER
                        note = 2'-O-methyl nucleoside
source                  1..10
                        mol_type = other RNA
                        organism = synthetic construct
modified_base           8
                        mod_base = OTHER
                        note = thymine
SEQUENCE: 30
aagcactttc                                                                10
```

METHODS AND COMPOSITIONS FOR TREATMENT OF POLYCYSTIC KIDNEY DISEASE

CROSS-REFERENCE TO RELATED APPLICATIONS

This application is a continuation of U.S. application Ser. No. 18/610,891, filed Mar. 20, 2024, which is a continuation of International Application No. PCT/US2022/077766, filed Oct. 7, 2022, which claims the benefit of priority of U.S. Provisional Application No. 63/253,933, filed Oct. 8, 2021, each of which is incorporated by reference herein in its entirety for any purpose.

SEQUENCE LISTING

The present application contains a Sequence Listing, which has been submitted electronically in XML format. Said XML copy, created on Mar. 3, 2025, is named "01138-0043-01US-T1.xml" and is 115,682 bytes in size. The information in the electronic format of the sequence listing is incorporated herein by reference in its entirety.

FIELD

Provided herein are compositions and methods for the treatment of polycystic kidney disease.

BACKGROUND

Polycystic kidney disease is characterized by the accumulation of numerous fluid-filled cysts in the kidney. These cysts are lined by a single layer of epithelial cells called the cyst epithelium. Over time, the cysts increase in size due to elevated cell proliferation and active secretion of fluid by the cyst epithelium. The enlarged cysts compress surrounding normal tissue, resulting in a decline of kidney function. The disease eventually progresses to end-stage renal disease, requiring dialysis or kidney transplant. At this stage, the cysts may be surrounded by areas of fibrosis containing atrophic tubules. Polycystic kidney disease can also cause cysts to develop in the liver and elsewhere in the body.

A number of genetic disorders can result in polycystic kidney disease (PKD). The various forms of PKD are distinguished by the manner of inheritance, for example, autosomal dominant or autosomal recessive inheritance; the involvement of organs and presentation of phenotypes outside of the kidney; the age of onset of end-stage renal disease, for example, at birth, in childhood or adulthood; and the underlying genetic mutation that is associated with the disease. See, for example, Kurschat et al., 2014, Nature Reviews Nephrology, 10: 687-699.

SUMMARY

Embodiment 1. A compound comprising a modified oligonucleotide, wherein the modified oligonucleotide has the following structure in the 5' to 3' orientation:

$$(N'')_p\text{—}(N)_r\text{—}(N')_q$$

wherein each N'' is, independently, a modified or unmodified nucleoside;

p is from 0 to 14; wherein if p is not 0, the nucleobase sequence of $(N'')_p$ is complementary to an equal-length portion of the nucleobase sequence of miR-17;

each N of $(N)_r$ is, independently, a modified or unmodified nucleotide, and the nucleobase sequence of $(N)_r$ is 5'-AGCACUUU-3';

N' is a nucleoside comprising a modified sugar moiety;

q is 0 or 1; wherein if q is 1, the nucleobase of N' is a uracil nucleobase, a cytosine nucleobase, or a purine nucleobase, provided that the purine nucleobase does not have a hydrogen bond acceptor at position 6; and each cytosine is independently selected from a non-methylated cytosine and a 5-methylcytosine; or a pharmaceutically acceptable salt thereof.

Embodiment 2. The compound of embodiment 1, wherein the structure of $(N)_r$ is:

$$A_SG_SC_MA_FC_FU_FU_MU_S$$

wherein nucleosides followed by subscript "M" are 2'-O-methyl nucleosides;

nucleosides followed by subscript "F" are 2'-fluoro nucleosides; and nucleosides followed by subscript "S" are S-cEt nucleosides.

Embodiment 3. The compound of embodiment 1 or embodiment 2, wherein at least one internucleoside linkage is a phosphorothioate internucleoside linkage.

Embodiment 4. The compound of any one of embodiments 1 to 3, wherein each internucleoside linkage is a phosphorothioate internucleoside linkage.

Embodiment 5. The compound of any one of embodiments 1 to 4, wherein q is 1.

Embodiment 6. The compound of any one of embodiments 1 to 4, wherein q is 0.

Embodiment 7. The compound of any one of embodiments 1 to 6, wherein p is 0.

Embodiment 8. The compound of any one of embodiments 1 to 6, wherein p is selected from 1, 2, 3, 4, 5, 6, 7, 8, 9, 10, 11, 12, 13, or 14.

Embodiment 9. The compound of embodiment 8, wherein the nucleobase sequence of $(N'')_p$ has no more than one mismatch to the nucleobase sequence of miR-17 (SEQ ID NO: 1).

Embodiment 10. The compound of embodiment 8, wherein the nucleobase sequence of $(N'')_p$ has no mismatches to the nucleobase sequence of miR-17 (SEQ ID NO: 1).

Embodiment 11. The compound of any one of embodiments 8, 9, or 10, wherein the nucleobase sequence of $(N'')_p$ is selected from CUACCUGCACUGUA (SEQ ID NO: 7), CUACCUGCACUGU (SEQ ID NO: 8), CUACCUGCACUG (SEQ ID NO: 9), CUACCUGCACU (SEQ ID NO: 10), CUACCUGCAC (SEQ ID NO: 11), CUACCUGCA, CUACCUGC, CUACCUG, CUACCU, CUACC, CUAC, CUA, CU, and C.

Embodiment 12. The compound of any one of embodiments 1 to 5 or 7 to 11, wherein the nucleobase of N' is a purine nucleobase that does not have a hydrogen bond acceptor at position 6.

Embodiment 13. The compound of embodiment 12, wherein the nucleobase of N' is selected from adenosine, 2-aminopurine, 2,6-diaminopurine, and isoguanosine.

Embodiment 14. The compound of any one of embodiments 1 to 13, wherein the sugar moiety of N' is not a 2'-O-methyl sugar.

Embodiment 15. The compound of any one of embodiments 1 to 14, wherein the sugar moiety of N' is a 2'-O-methoxyethyl sugar or an S-cEt sugar.

Embodiment 16. The compound of embodiment 2, wherein the structure of the modified oligonucleotide is 5'-$A_SG_SC_MA_FC_FU_FU_MU_SA_S$-3', wherein each cytosine is a non-methylated cytosine.

Embodiment 17. The compound of embodiment 2, wherein the structure of the modified oligonucleotide is 5'-$A_SG_SC_MA_FC_FU_FU_MU_SU_S$-3', wherein each cytosine is a non-methylated cytosine.

Embodiment 18. The compound of embodiment 2, wherein the structure of the modified oligonucleotide is 5'-$A_SG_SC_MA_FC_FU_FU_MU_SC_S$-3', wherein each cytosine is a non-methylated cytosine.

Embodiment 19. The compound of embodiment 2, wherein the structure of the modified oligonucleotide is 5'-$A_SG_SC_MA_FC_FU_FU_MU_S$-3', wherein each cytosine a non-methylated cytosine.

Embodiment 20. The compound of any one of embodiments 1 to 19, wherein the compound consists of the modified oligonucleotide.

Embodiment 21. The compound of any one of embodiments 1 to 20, wherein the pharmaceutically acceptable salt is a sodium salt.

Embodiment 22. A modified oligonucleotide having the structure:

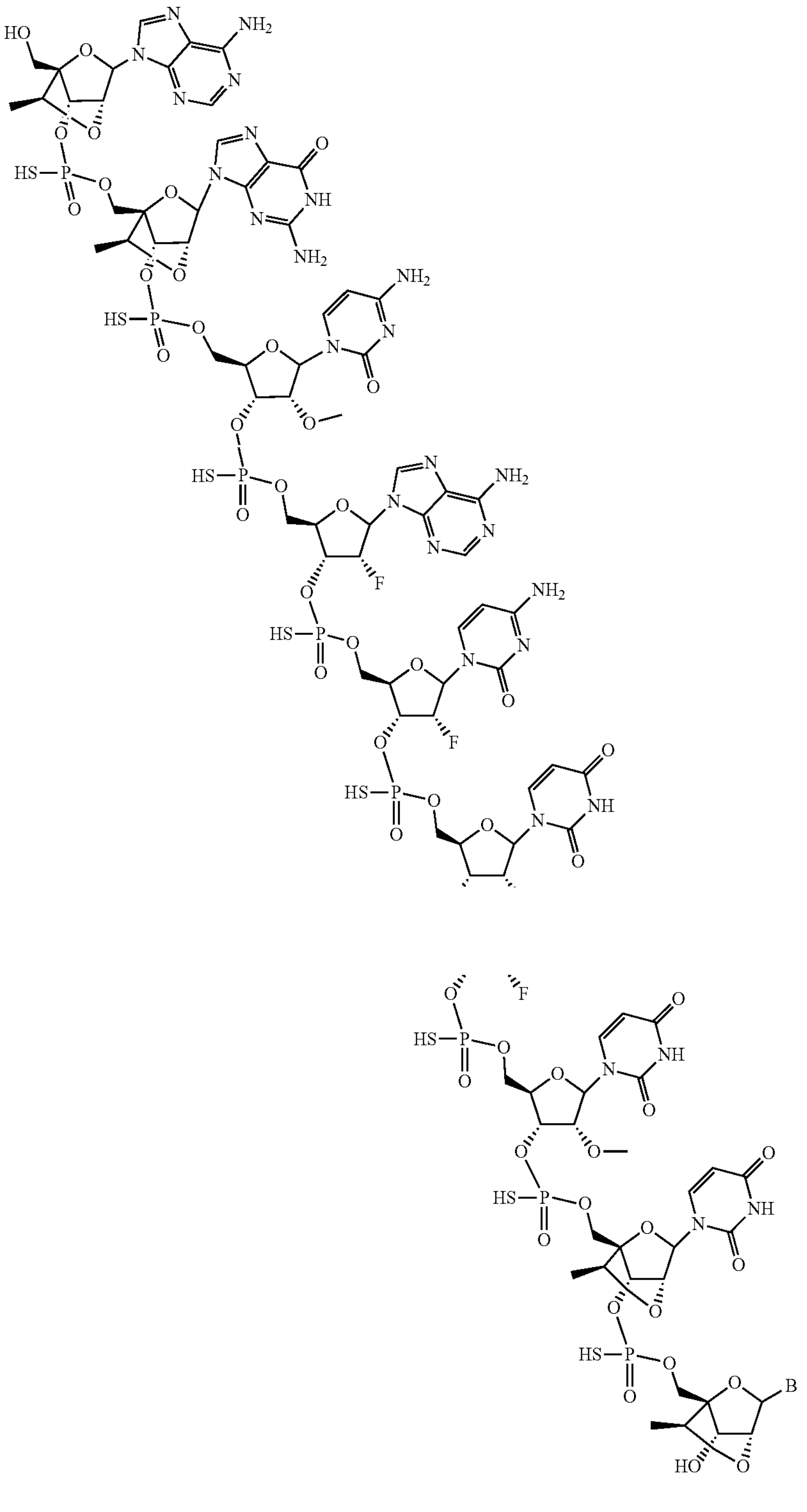

wherein B is a uridine nucleobase, a cytosine nucleobase, or a purine nucleobase, provided that the purine nucleobase does not have a hydrogen bond acceptor at position 6; or a pharmaceutically acceptable salt thereof.

Embodiment 23. The modified oligonucleotide of embodiment 22, wherein B is selected from adenosine, 2-aminopurine, 2,6-diaminopurine, and isoguanosine.

Embodiment 24. The modified oligonucleotide of embodiment 22 or embodiment 23, wherein the pharmaceutically acceptable salt is a sodium salt.

Embodiment 25. A modified oligonucleotide having the structure:

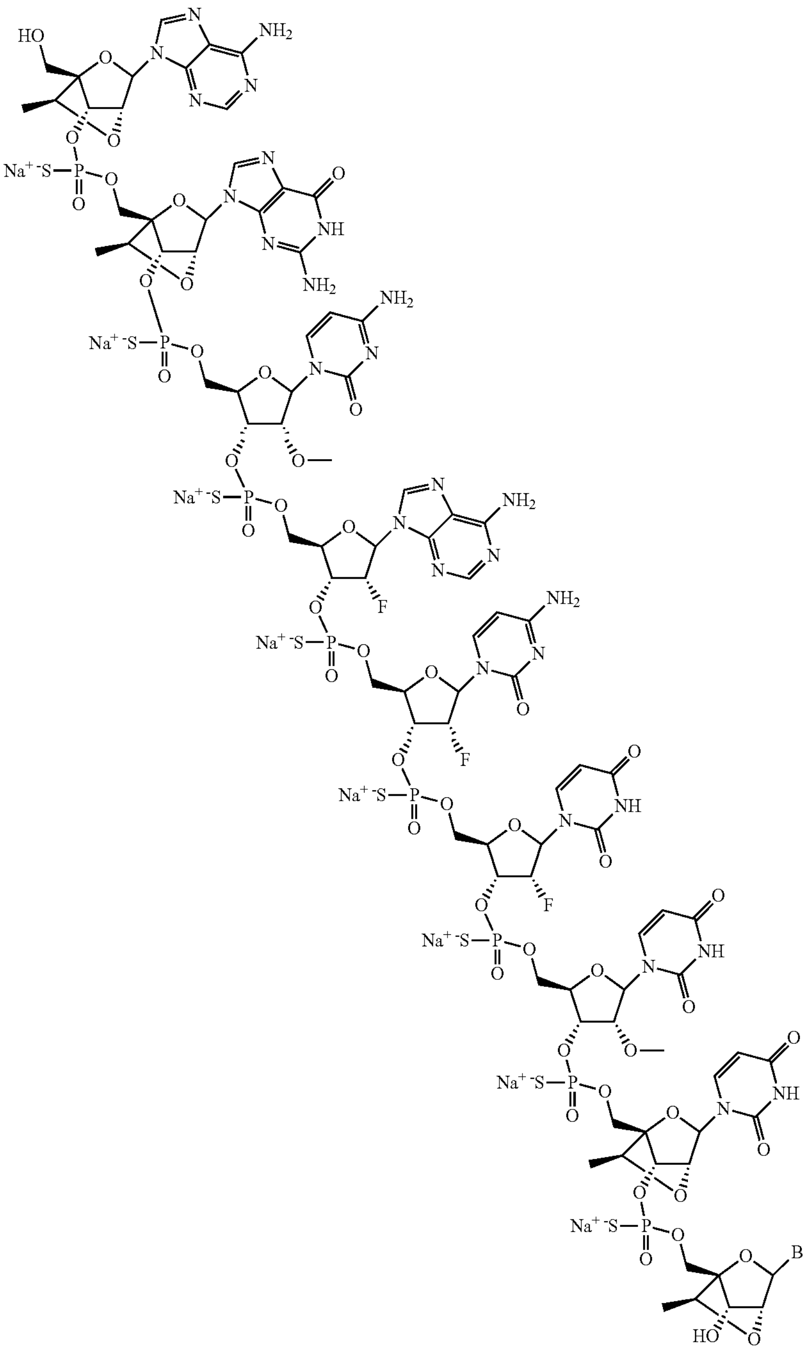

wherein B is a uridine nucleobase, a cytosine nucleobase, or a purine nucleobase, provided that the purine nucleobase does not have a hydrogen bond acceptor at position 6.

Embodiment 26. The modified oligonucleotide of embodiment 25, wherein B is selected from adenosine, 2-aminopurine, 2,6-diaminopurine, and isoguanosine.

Embodiment 27. A modified oligonucleotide having the structure:

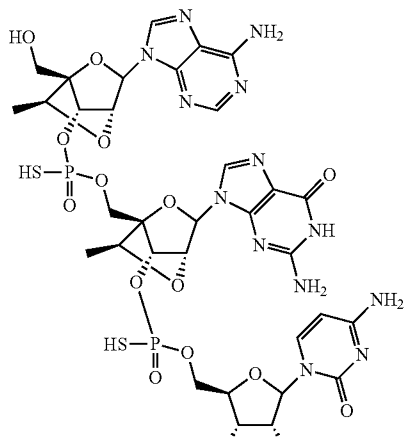
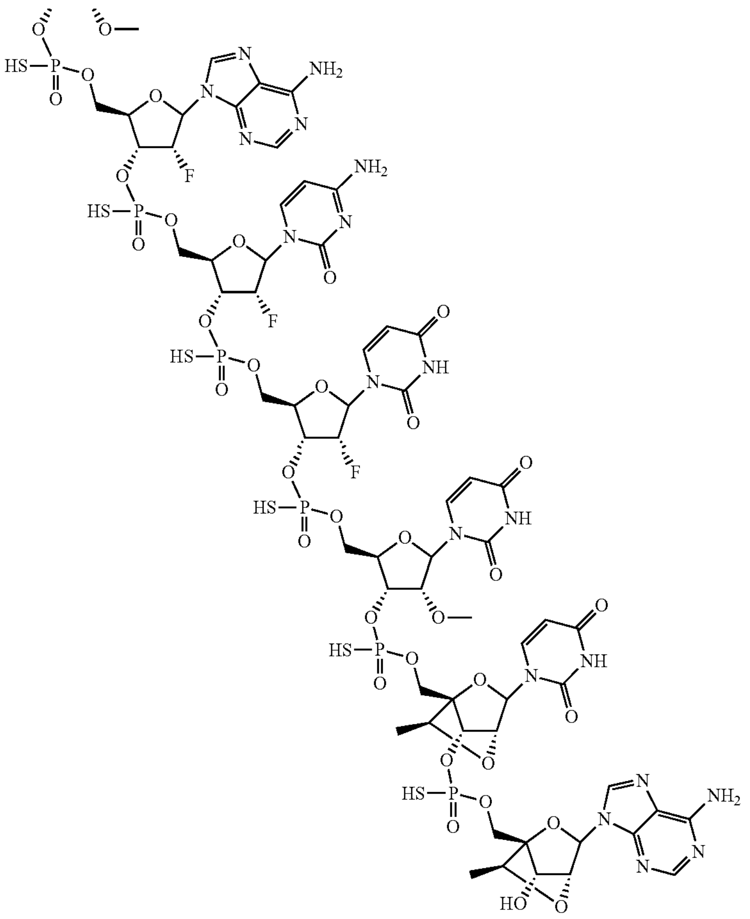
or a pharmaceutically acceptable salt thereof.
Embodiment 28. The modified oligonucleotide of embodiment 27, wherein the pharmaceutically acceptable salt is a sodium salt.
Embodiment 29. A modified oligonucleotide having the structure:

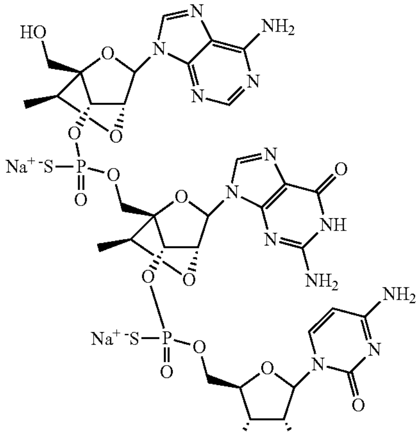
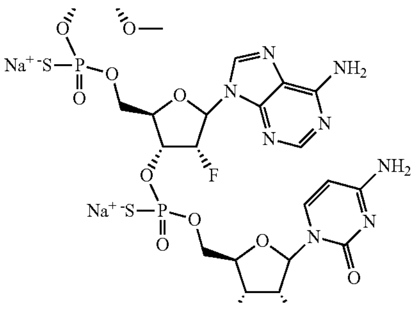
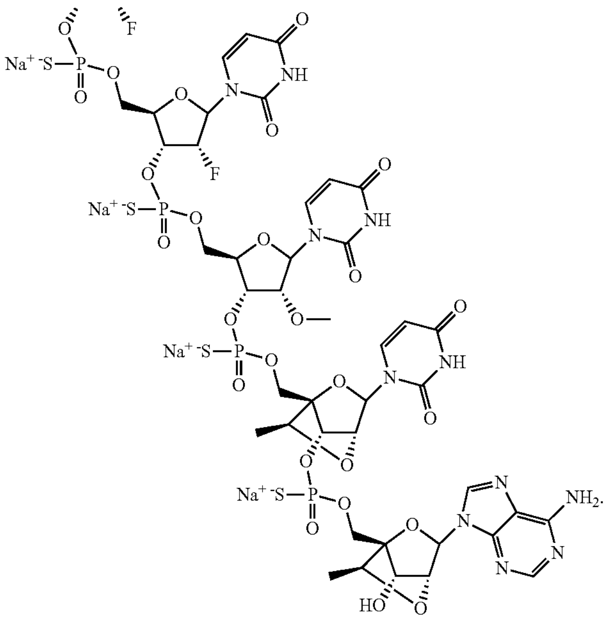

Embodiment 30. A pharmaceutical composition comprising a compound of any one of embodiments 1 to 21 or a modified oligonucleotide of any one of embodiments 22 to 29 and a pharmaceutically acceptable diluent.

Embodiment 31. The pharmaceutical composition of embodiment 30, wherein the pharmaceutically acceptable diluent is an aqueous solution.

Embodiment 32. The pharmaceutical composition of embodiment 31, wherein the aqueous solution is a saline solution.

Embodiment 33. A pharmaceutical composition comprising a compound of any one of embodiments 1 to 21 or a modified oligonucleotide of any one of embodiments 22 to 29, which is a lyophilized composition.

Embodiment 34. A pharmaceutical composition consisting essentially of a compound of any one of embodiments 1 to 21 or a modified oligonucleotide of any one of embodiments 22 to 29 in a saline solution.

Embodiment 35. A method for inhibiting the activity of one or more members of the miR-17 family in a cell, comprising contacting the cell with a compound of any one of embodiments 1 to 21 or a modified oligonucleotide of any one of embodiments 22 to 29.

Embodiment 36. A method for inhibiting the activity of one or more members of the miR-17 family in a subject, comprising administering to the subject a compound of any one of embodiments 1 to 21, a modified oligonucleotide of any one of embodiments 22 to 29, or a pharmaceutical composition of any one of embodiments 30 to 34.

Embodiment 37. The method of embodiment 36, wherein the subject has a disease associated with miR-17.

Embodiment 38. A method of treating polycystic kidney disease comprising administering to a subject in need thereof a compound comprising a modified oligonucleotide, wherein the modified oligonucleotide has the following structure in the 5' to 3' orientation:

$$(N'')_p—(N)_r—(N')_q$$

wherein each N'' is, independently, a modified or unmodified nucleoside;

p is from 0 to 14; wherein if p is not 0, the nucleobase sequence of $(N'')_p$ is complementary to an equal-length portion of the nucleobase sequence of miR-17;

each N of $(N)_r$ is, independently, a modified or unmodified nucleotide, and the nucleobase sequence of $(N)_r$ is 5'-AGCACUUU-3';

N' is a nucleoside comprising a modified sugar moiety;

q is 0 or 1; wherein if q is 1, the nucleobase of N' is a uridine nucleobase, a cytosine nucleobase, or a purine nucleobase, provided that the purine nucleobase does not have an H-bond acceptor at position 6; and each cytosine is independently selected from a non-methylated cytosine and a 5-methylcytosine;

or a pharmaceutically acceptable salt thereof.

Embodiment 39. The method of embodiment 38, wherein the structure of $(N)_r$ is:

$$A_SG_SC_MA_FC_FU_FU_MU_S$$

wherein nucleosides followed by subscript "M" are 2'-O-methyl nucleosides; nucleosides followed by subscript "F" are 2'-fluoro nucleosides; and nucleosides followed by subscript "S" are S-cEt nucleosides.

Embodiment 40. The method of embodiment 38 or embodiment 39, wherein at least one internucleoside linkage is a phosphorothioate internucleoside linkage.

Embodiment 41. The method of any one of embodiments 38 to 40, wherein each internucleoside linkage is a phosphorothioate internucleoside linkage.

Embodiment 42. The method of any one of embodiments 38 to 41, wherein q is 1.

Embodiment 43. The method of any one of embodiments 38 to 41, wherein q is 0.

Embodiment 44. The method of any one of embodiments 38 to 43, wherein p is 0.

Embodiment 45. The method of any one of embodiments 38 to 43, wherein p is selected from 1, 2, 3, 4, 5, 6, 7, 8, 9, 10, 11, 12, 13, or 14.

Embodiment 46. The method of embodiment 45, wherein the nucleobase sequence of $(N'')_p$ has no more than one mismatch to the nucleobase sequence of miR-17 (SEQ ID NO: 1).

Embodiment 47. The compound of embodiment 45, wherein the nucleobase sequence of $(N'')_p$ has no mismatches to the nucleobase sequence of miR-17 (SEQ ID NO: 1).

Embodiment 48. The compound of embodiment 47, wherein the nucleobase sequence of $(N'')_p$ is selected from CUACCUGCACUGUA (SEQ ID NO: 7), CUACCUGCACUGU (SEQ ID NO: 8), CUACCUGCACUG (SEQ ID NO: 9), CUACCUGCACU (SEQ ID NO: 10), CUACCUGCAC (SEQ ID NO: 11), CUACCUGCA, CUACCUGC, CUACCUG, CUACCU, CUACC, CUAC, CUA, CU, and C.

Embodiment 49. The method of any one of embodiments 38 to 42 or 44 to 48, wherein the nucleobase of N' is a purine nucleobase that does not have a hydrogen-bond acceptor at position 6.

Embodiment 50. The method of embodiment 49, wherein the nucleobase of N' is selected from adenosine, 2-aminopurine, 2,6-diaminopurine, and isoguanosine.

Embodiment 51. The method of any one of embodiments 38 to 50, wherein the sugar moiety of N' is not a 2'-O-methyl sugar.

Embodiment 52. The compound of any one of embodiments 38 to 51, wherein the sugar moiety of N' is a 2'-O-methoxyethyl sugar or an S-cEt sugar.

Embodiment 53. The method of embodiment 39, wherein the structure of the modified oligonucleotide is 5'-$A_SG_SC_MA_FC_FU_FU_MU_SA_S$-3', and each cytosine is a non-methylated cytosine.

Embodiment 54. The method of embodiment 39, wherein the structure of the modified oligonucleotide is 5'-$A_SG_SC_MA_FC_FU_FU_MU_SU_S$-3', wherein each cytosine is a non-methylated cytosine.

Embodiment 55. The method of embodiment 39, wherein the structure of the modified oligonucleotide is 5'-$A_SG_SC_MA_FC_FU_FU_MU_SC_S$-3', wherein each cytosine is a non-methylated cytosine.

Embodiment 56. The method of embodiment 39, wherein the structure of the modified oligonucleotide is 5'-$A_SG_SC_MA_FC_FU_FU_MU_S$-3', wherein each cytosine a non-methylated cytosine.

Embodiment 57. The method of any one of embodiments 38 to 56, wherein the compound consists of the modified oligonucleotide.

Embodiment 58. The method of any one of embodiments 38 to 57, wherein the pharmaceutically acceptable salt is a sodium salt.

Embodiment 59. A method of treating polycystic kidney disease comprising administering to a subject in need thereof a modified oligonucleotide having the structure:

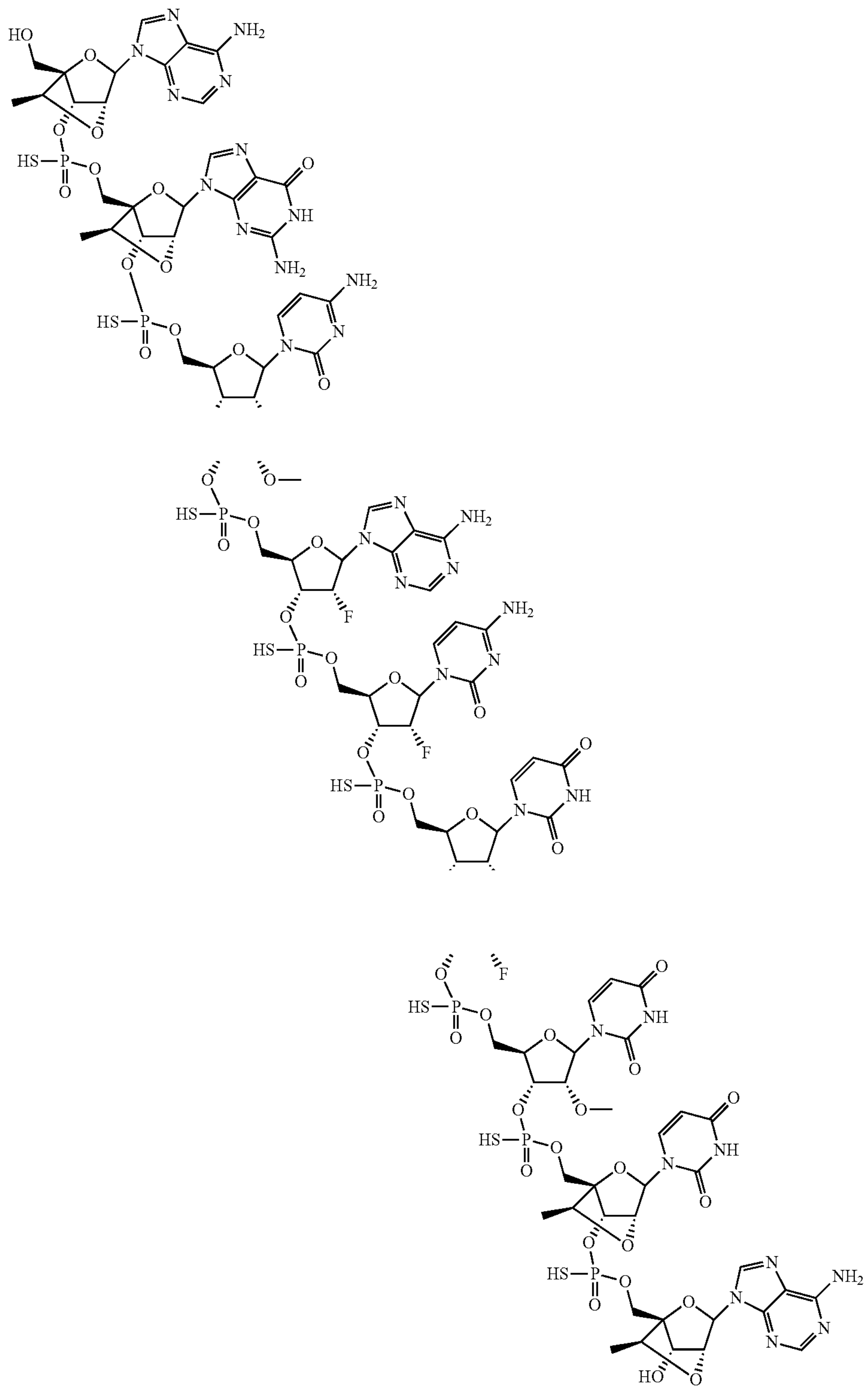

or a pharmaceutically acceptable salt thereof.

Embodiment 60. The method of embodiment 59, wherein pharmaceutically acceptable salt is a sodium salt.

Embodiment 61. The method of embodiment 60, wherein the modified oligonucleotide is present in a pharmaceutical composition comprising a pharmaceutically acceptable diluent.

Embodiment 62. The method of embodiment 61, wherein the pharmaceutically acceptable diluent is a sterile aqueous solution.

Embodiment 63. The method of embodiment 62, wherein the sterile aqueous solution is a saline solution.

Embodiment 64. A method of treating polycystic kidney disease comprising administering to a subject in need thereof a modified oligonucleotide having the structure:

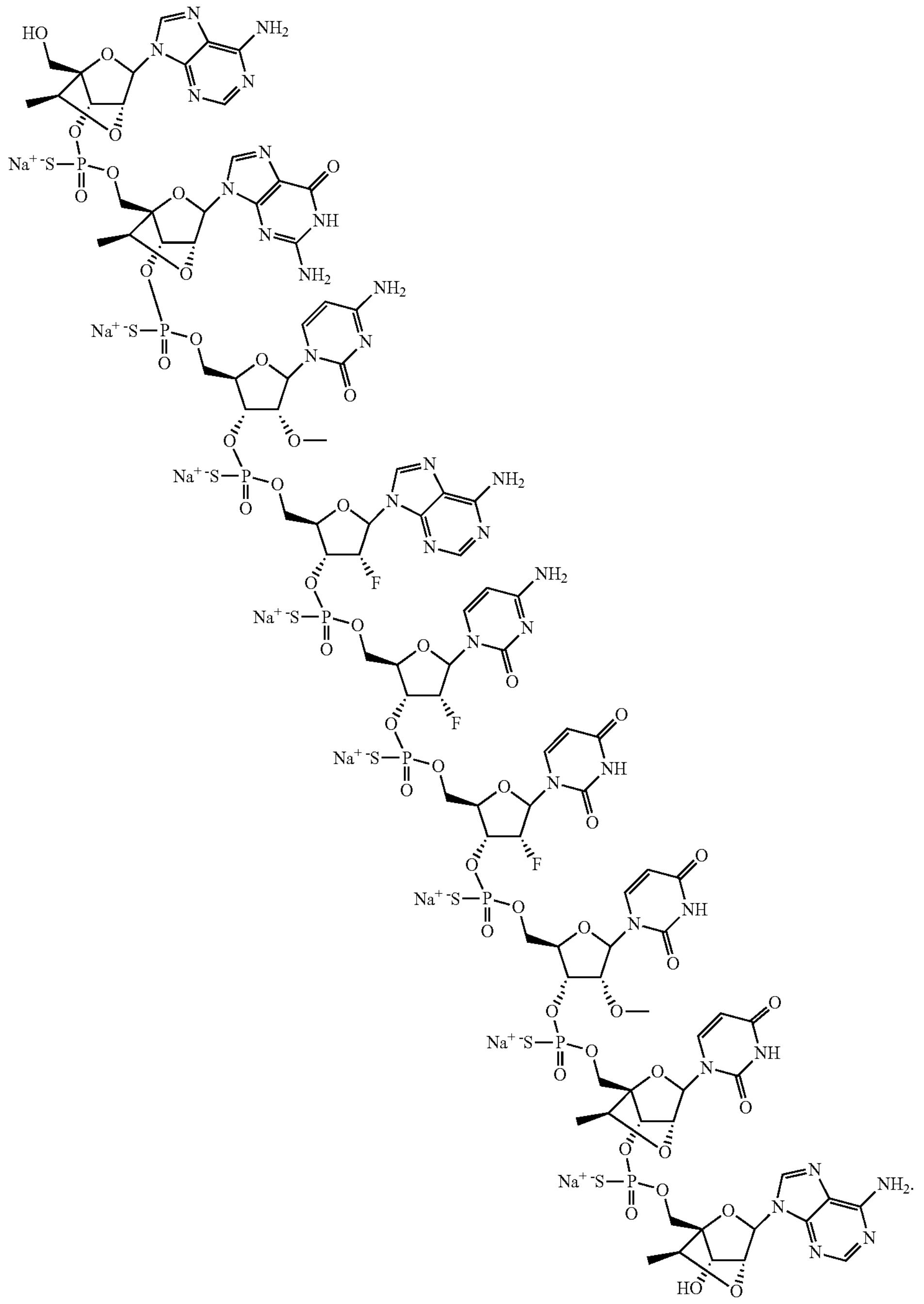

Embodiment 65. The method of embodiment 64, wherein the modified oligonucleotide is present in a pharmaceutical composition comprising a pharmaceutically acceptable diluent.

Embodiment 66. The method of embodiment 65, wherein the pharmaceutically acceptable diluent is a sterile aqueous solution.

Embodiment 67. The method of embodiment 66, wherein the sterile aqueous solution is a saline solution.

Embodiment 68. The method of any one of embodiments 38 to 67, wherein the subject has polycystic kidney disease.

Embodiment 69. The method of any one of embodiments 38 to 67, wherein the subject is suspected of having polycystic kidney disease.

Embodiment 70. The method of any one of embodiments 38 to 68, wherein the subject has been diagnosed as having polycystic kidney disease using clinical, histopathologic, and/or genetic criteria.

Embodiment 71. The method of any one of embodiments 38 to 70, wherein the subject, prior to administration of the compound, modified oligonucleotide, or pharmaceutical composition, was determined to have a decreased level of polycystin-1 (PC1) and/or polycystin-2 (PC2) in the kidney, urine or blood of the subject.

Embodiment 72. The method of any one of embodiments 38 to 71, wherein the polycystic kidney disease is autosomal recessive polycystic kidney disease.

Embodiment 73. The method of any one of embodiments 38 to 71, wherein the polycystic kidney disease is autosomal dominant polycystic kidney disease.

Embodiment 74. The method of any one of embodiments 38 to 73, wherein the subject has a mutation selected from a mutation in the PKD1 gene or a mutation in the PKD2 gene.

Embodiment 75. The method of any one of embodiments 38 to 74, wherein the subject has increased total kidney volume.

Embodiment 76. The method of any one of embodiments 38 to 75, wherein the subject has hypertension.

Embodiment 77. The method of any one of embodiments 38 to 76, wherein the subject has impaired kidney function.

Embodiment 78. The method of any one of embodiments 38 to 77, wherein the administering reduces total kidney volume in the subject.

Embodiment 79. The method of any one of embodiments 38 to 78, wherein the administering slows the rate of increase of total kidney volume in the subject.

Embodiment 80. The method of embodiment 78 or embodiment 79, wherein the total kidney volume is height-adjusted total kidney volume.

Embodiment 81. The method of any one of embodiments 38 to 80, wherein the administering slows the rate of decline of glomerular filtration rate in the subject.

Embodiment 82. The method of any one of embodiments 38 to 81, wherein the administering increases glomerular filtration rate in the subject.

Embodiment 83. The method of embodiment 81 or embodiment 82, wherein the glomerular filtration rate is estimated glomerular filtration rate.

Embodiment 84. The method of any one of embodiments 38 to 83, wherein the administering slows the increase in the growth of cysts in the kidney and/or liver of the subject.

Embodiment 85. The method of any one of embodiments 38 to 84, wherein the administering:

a) improves kidney function in the subject;
b) delays the worsening of kidney function in the subject;
c) reduces kidney pain in the subject;
d) slows the increase in kidney pain in the subject;
e) delays the onset of kidney pain in the subject;
f) reduces hypertension in the subject;
g) slows the worsening of hypertension in the subject;
h) delays the onset of hypertension in the subject;
i) reduces fibrosis in the kidney of the subject;
j) slows the worsening of fibrosis in the kidney of the subject;
k) delays the onset of end stage renal disease in the subject;
l) delays time to dialysis for the subject;
m) delays time to renal transplant for the subject; and/or
n) improves life expectancy of the subject.

Embodiment 86. The method of any one of embodiments 38 to 85, wherein the administering:

a) reduces albuminuria in the subject;
b) slows the worsening of albuminuria in the subject;
c) delays the onset of albuminuria in the subject;
d) reduces hematuria in the subject;
e) slows the worsening of hematuria in the subject;
f) delays the onset of hematuria in the subject;
g) reduces blood urea nitrogen level in the subject;
h) reduces serum creatinine level in the subject;
i) improves creatinine clearance in the subject;
j) reduces albumin:creatinine ratio in the subject;
k) increases polycystin-1 (PC1) in the urine of the subject;
l) increases polycystin-2 (PC2) in the urine of the subject;
m) reduces neutrophil gelatinase-associated lipocalin (NGAL) protein in the urine of the subject; and/or
n) reduces kidney injury molecule-1 (KIM-1) protein in the urine of the subject.

Embodiment 87. The method of one of embodiments 38 to 86, comprising:

a) measuring total kidney volume in the subject;
b) measuring hypertension in the subject;
c) measuring kidney pain in the subject;
d) measuring polycystin-1 (PC1) in the urine of the subject;
e) measuring polycystin-2 (PC2) in the urine of the subject;
f) measuring fibrosis in the kidney of the subject;
g) measuring blood urea nitrogen level in the subject;
h) measuring serum creatinine level in the subject;
i) measuring creatinine clearance in the subject;
j) measuring albuminuria in the subject;
k) measuring albumin:creatinine ratio in the subject;
l) measuring glomerular filtration rate in the subject;
m) measuring neutrophil gelatinase-associated lipocalin (NGAL) protein in the urine of the subject; and/or
n) measuring kidney injury molecule-1 (KIM-1) protein in the urine of the subject.

Embodiment 88. The method of any one of embodiments 38 to 87, comprising administering at least one additional therapy, wherein at least one additional therapy is an anti-hypertensive agent.

Embodiment 89. The method of any one of embodiments 38 to 87, comprising administering at least one additional therapy selected from an angiotensin II converting enzyme (ACE) inhibitor, an angiotensin II receptor blocker (ARB), a diuretic, a calcium channel blocker, a kinase inhibitor, an adrenergic receptor antagonist, a vasodilator, a benzodiazepine, a renin inhibitor, an aldosterone receptor antagonist, an endothelin receptor blocker, an mammalian target of rapamycin (mTOR) inhibitor, a hormone analogue, a vasopressin receptor 2 antagonist, an aldosterone receptor antagonist, a glucosylceramide synthase inhibitor, an anti-hyperglycermic agent, dialysis, and kidney transplant.

Embodiment 90. The method of embodiment 89, wherein the angiotensin II converting enzyme (ACE) inhibitor is selected from captopril, enalapril, lisinopril, benazepril, quinapril, fosinopril, and ramipril.

Embodiment 91. The method of embodiment 89, wherein the angiotensin II receptor blocker (ARB) is selected from candesartan, irbesartan, olmesartan, losartan, valsartan, telmisartan, and eprosartan.

Embodiment 92. The method of embodiment 89, wherein the vasopressin receptor 2 antagonist is tolvaptan.

Embodiment 93. The method of embodiment 89, wherein the aldosterone receptor antagonist is spironolactone.

Embodiment 94. The method of embodiment 89, wherein the kinase inhibitor is selected from bosutinib and KD019.

Embodiment 95. The method of embodiment 89, wherein the mTOR inhibitor is selected from everolimus, rapamycin, and sirolimus.

Embodiment 96. The method of embodiment 89, wherein the hormone analogue is selected from somatostatin and adrenocorticotrophic hormone.

Embodiment 97. The method of embodiment 89, wherein the glucosylceramide synthase inhibitor is venglustat.

Embodiment 98. The method of embodiment 89, wherein the antihyperglycemic agent is metformin.

Embodiment 99. The method of any one of embodiments 38 to 96, comprising administering a therapeutically effective amount of the compound.

Embodiment 100. The method of any one of embodiments 38 to 99, wherein the subject is a human subject.

Embodiment 101. A compound comprising a modified oligonucleotide, wherein the modified oligonucleotide has the following structure in the 5' to 3' orientation:

$$(N'')_p—(N)_r—(N')_q$$

wherein each N" is, independently, a modified or unmodified nucleoside;

p is from 0 to 14; wherein if p is not 0, the nucleobase sequence of $(N'')_p$ is complementary to an equal-length portion of the nucleobase sequence of miR-17;

each N of $(N)_r$ is, independently, a modified or unmodified nucleotide, and the nucleobase sequence of $(N)_r$ is 5'-AGCACUUU-3';

N' is a nucleoside comprising a modified sugar moiety;

q is 0 or 1; wherein if q is 1, the nucleobase of N' is a uridine nucleobase, a cytosine nucleobase, or a purine nucleobase, provided that the purine nucleobase does not have an H-bond acceptor at position 6; and each cytosine is independently selected from a non-methylated cytosine and a 5-methylcytosine; or a pharmaceutically acceptable salt thereof, for use in therapy.

Embodiment 102. The compound of embodiment 101, wherein the therapy is the treatment of polycystic kidney disease.

Embodiment 103. The compound of embodiment 102, wherein the polycystic kidney disease is autosomal dominant polycystic kidney disease (ADPKD).

Embodiment 104. The compound of embodiment 102, wherein the polycystic kidney disease is autosomal recessive polycystic kidney disease (ARPKD).

Embodiment 105. A compound of any one of embodiments 1 to 22, a modified oligonucleotide of any one of embodiments 23 to 29, or a pharmaceutical composition of any one of embodiments 30 to 33, for use in therapy.

DETAILED DESCRIPTION

Figure 1:
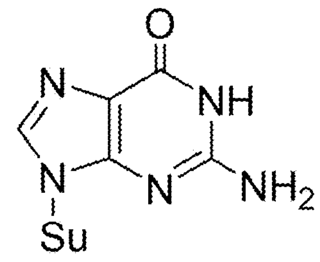
FIG. 1. Purine nucleobase structures.
Figure 1:
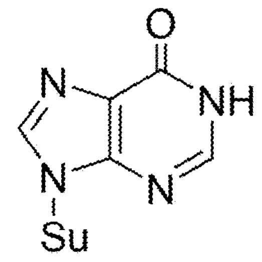
Figure 1:
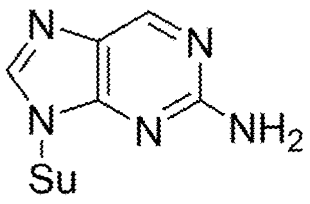
Figure 1:
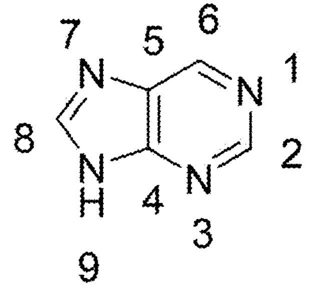
Figure 1:
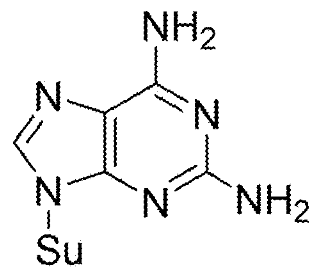
Figure 1:
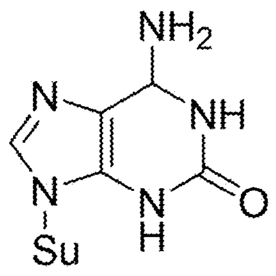
Figure 1:
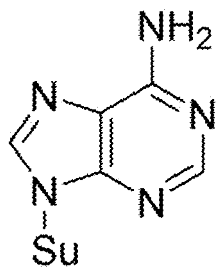

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sanghvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can change, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Definitions

"Polycystic kidney disease" or "PKD" is a cystic kidney disease characterized by the accumulation of numerous fluid-filled cysts in the kidney. Multiple cysts form in at least one kidney, frequently leading to enlargement of the affected kidney(s) and progressive loss of kidney function.

"Marker of polycystic kidney disease" means a medical parameter that is used to assess severity of polycystic kidney disease, kidney function, and/or response of a subject having polycystic kidney disease to treatment. Non-limiting examples of markers of polycystic kidney disease include total kidney volume, hypertension, glomerular filtration rate, and kidney pain.

"Marker of kidney function" means a medical parameter that is used to assess kidney function in a subject. Non-limiting examples of markers of kidney function include glomerular filtration rate, blood urea nitrogen level, and serum creatinine level.

"Autosomal dominant polycystic kidney disease" or "ADPKD" is a polycystic kidney disease caused by one or more genetic mutations in the PKD1 and/or PDK2 gene. 85% of ADPKD is caused by mutations in PKD1, which is located on chromosome 16, with the majority of the remaining ADPKD cases caused by mutations in PKD2, which is located on chromosome 4.

"Autosomal recessive polycystic kidney disease" or "ARPKD" is a polycystic kidney disease caused by one or more genetic mutations in the PKHD1 gene, which is located on chromosome 6. Up to 50% of neonates with ARPKD die from complications of intrauterine kidney disease, and about a third of those who survive develop end stage renal disease (ESRD) within 10 years.

"Nephronophthisis" or "NPHP" means an autosomal recessive cystic kidney disease characterized by corticomedullary cysts, tubular basement membrane disruption, and tubulointerstitial nephropathy.

"Total kidney volume" or "TKV" is a measurement of total kidney volume. Total kidney volume may be determined by Magnetic Resonance Imaging (MRI), Computed Tomography (CT) scan, or ultrasound (US) imaging, and the volume calculated by a standard methodology, such as an ellipsoid volume equation (for ultrasound), or by quantitative stereology or boundary tracing (for CT/MRI).

"Height-adjusted total kidney volume" or "HtTKV" is a measure of total kidney volume per unit height. Patients with an HtTKV value ≥600 ml/m are predicted to develop stage 3 chronic kidney disease within 8 years.

"Kidney pain" means clinically significant kidney pain necessitating medical leave, pharmacologic treatment (narcotic or last-resort analgesic agents), or invasive intervention.

"Worsening hypertension" means a change in blood pressure that requires initiation of or an increase in hypertensive treatment.

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

"Hematuria" means the presence of red blood cells in the urine.

"Albuminuria" means the presence of excess albumin in the urine, and includes without limitation, normal albuminuria, high normal albuminuria, microalbuminuria and macroalbuminuria. Normally, the glomerular filtration permeability barrier, which is composed of podocyte, glomerular basement membrane and endothelial cells, prevents serum protein from leaking into urine. Albuminuria may reflect injury of the glomerular filtration permeability barrier. Albuminuria may be calculated from a 24-hour urine sample, an overnight urine sample or a spot-urine sample.

"High normal albuminuria" means elevated albuminuria characterized by (i) the excretion of 15 to <30 mg of albumin into the urine per 24 hours and/or (ii) an albumin/creatinine ratio of 1.25 to <2.5 mg/mmol (or 10 to <20 mg/g) in males or 1.75 to <3.5 mg/mmol (or 15 to <30 mg/g) in females.

"Microalbuminuria" means elevated albuminuria characterized by (i) the excretion of 30 to 300 mg of albumin into the urine per 24 hours and/or (ii) an albumin/creatinine ratio of 2.5 to <25 mg/mmol (or 20 to <200 mg/g) in males or 3.5 to <35 mg/mmol (or 30 to <300 mg/g) in females.

"Macroalbuminuria" means elevated albuminuria characterized by the excretion of more than 300 mg of albumin into the urine per 24 hours and/or (ii) an albumin/creatinine ratio of >25 mg/mmol (or >200 mg/g) in males or >35 mg/mmol (or >300 mg/g) in females.

"Albumin/creatinine ratio" means the ratio of urine albumin (mg/dL) per urine creatinine (g/dL) and is expressed as mg/g. In certain embodiments, albumin/creatinine ratio may be calculated from a spot-urine sample and may be used as an estimate of albumin excretion over a 24-hour period.

"Glomerular filtration rate" or "GFR" means the flow rate of filtered fluid through the kidney and is used as an indicator of kidney function in a subject. In certain embodiments, a subject's GFR is determined by calculating an estimated glomerular filtration rate. In certain embodiments, a subject's GFR is directly measured in the subject, using the inulin method.

"Estimated glomerular filtration rate" or "eGFR" means a measurement of how well the kidneys are filtering creatinine, and is used to approximate glomerular filtration rate. As the direct measurement of GFR is complex, eGFR is frequently used in clinical practice. Normal results may range from 90-120 mL/min/1.73 $m^2$. Levels below 60 mL/min/1.73 $m^2$ for 3 or more months may be an indicator chronic kidney disease. Levels below 15 mL/min/1.73 $m^2$ may be an indicator of kidney failure.

"Proteinuria" means the presence of an excess of serum proteins in the urine. Proteinuria may be characterized by the excretion of >250 mg of protein into the urine per 24 hours and/or a urine protein to creatinine ratio of >0.20 mg/mg. Serum proteins elevated in association with proteinuria include, without limitation, albumin.

"Blood urea nitrogen level" or "BUN level" means a measure of the amount of nitrogen in the blood in the form of urea. The liver produces urea in the urea cycle as a waste product of the digestion of protein, and the urea is removed from the blood by the kidneys. Normal human adult blood may contain between 7 to 21 mg of urea nitrogen per 100 ml (7-21 mg/dL) of blood. Measurement of blood urea nitrogen level is used as an indicator of renal health. If the kidneys are not able to remove urea from the blood normally, a subject's BUN level rises.

"Elevated" means an increase in a medical parameter that is considered clinically relevant. A health professional may determine whether an increase is clinically significant.

"End stage renal disease (ESRD)" means the complete or almost complete failure of kidney function.

"Quality of life" means the extent to which a subject's physical, psychological, and social functioning are impaired by a disease and/or treatment of a disease. Quality of life may be reduced in subjects having polycystic kidney disease.

"Impaired kidney function" means reduced kidney function, relative to normal kidney function.

"Slow the worsening of" and "slow worsening" mean to reduce the rate at which a medical condition moves towards an advanced state.

"Delay time to dialysis" means to maintain sufficient kidney function such that the need for dialysis treatment is delayed.

"Delay time to renal transplant" means to maintain sufficient kidney function such that the need for a kidney transplant is delayed.

"Improves life expectancy" means to lengthen the life of a subject by treating one or more symptoms of a disease in the subject.

"Subject" means a human or non-human animal selected for treatment or therapy.

"Subject in need thereof" means a subject that is identified as in need of a therapy or treatment.

"Subject suspected of having" means a subject exhibiting one or more clinical indicators of a disease.

"Disease associated with miR-17" means a disease or condition that is modulated by the activity of one or more miR-17 family members.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, and intramuscular administration.

"Subcutaneous administration" means administration just below the skin.

"Intravenous administration" means administration into a vein.

"Administered concomitantly" refers to the co-administration of two or more agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period and need not be coextensive.

"Duration" means the period during which an activity or event continues. In certain embodiments, the duration of treatment is the period during which doses of a pharmaceutical agent or pharmaceutical composition are administered.

"Therapy" means a disease treatment method. In certain embodiments, therapy includes, but is not limited to, administration of one or more pharmaceutical agents to a subject having a disease.

"Treat" means to apply one or more specific procedures used for the amelioration of at least one indicator of a disease. In certain embodiments, the specific procedure is the administration of one or more pharmaceutical agents. In certain embodiments, treatment of PKD includes, but is not limited to, reducing total kidney volume, improving kidney function, reducing hypertension, and/or reducing kidney pain.

"Ameliorate" means to lessen the severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In certain embodiments, a dose is administered as a slow infusion.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Pharmaceutically acceptable salt" means a physiologically and pharmaceutically acceptable salt of a compound provided herein, i.e., a salt that retains the desired biological activity of the compound and does not have undesired toxicological effects when administered to a subject. Non-limiting exemplary pharmaceutically acceptable salts of compounds provided herein include sodium and potassium salt forms. The terms "compound," "oligonucleotide," and "modified oligonucleotide" as used herein include pharmaceutically acceptable salts thereof unless specifically indicated otherwise.

"Saline solution" means a solution of sodium chloride in water.

"Improved organ function" means a change in organ function toward normal limits. In certain embodiments, organ function is assessed by measuring molecules found in a subject's blood or urine. For example, in certain embodiments, improved kidney function is measured by a reduction in blood urea nitrogen level, a reduction in proteinuria, a reduction in albuminuria, etc.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, kidney function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

The term "blood" as used herein, encompasses whole blood and blood fractions, such as serum and plasma.

"Anti-miR" means an oligonucleotide having a nucleobase sequence complementary to a microRNA. In certain embodiments, an anti-miR is a modified oligonucleotide.

"Anti-miR-17" means a modified oligonucleotide having a nucleobase sequence complementary to one or more miR-17 family members. In certain embodiments, an anti-miR-17 is fully complementary (i.e., 100% complementary) to one or more miR-17 family members. In certain embodiments, an anti-miR-17 is at least 80%, at least 85%, at least 90%, or at least 95% complementary to one or more miR-17 family members.

"miR-17" means the mature miRNA having the nucleobase sequence 5'-CAAAGUGCUUACAGUGCAGGUAG-3' (SEQ ID NO: 1).

"miR-20a" means the mature miRNA having the nucleobase sequence 5'-UAAAGUGCUUAUAGUGCAGGUAG-3' (SEQ ID NO: 2).

"miR-20b" means the mature miRNA having the nucleobase sequence 5'-CAAAGUGCUCAUAGUGCAGGUAG-3' (SEQ ID NO: 3).

"miR-93" means the mature miRNA having the nucleobase sequence 5'-CAAAGUGCUGUUCGUGCAGGUAG-3' (SEQ ID NO: 4).

"miR-106a" means the mature miRNA having the nucleobase sequence 5'-AAAAGUGCUUACAGUGCAGGUAG-3' (SEQ ID NO: 5).

"miR-106b" means the mature miRNA having the nucleobase sequence 5'-UAAAGUGCUGACAGUGCAGAU-3' (SEQ ID NO: 6).

"miR-17 seed sequence" means the nucleobase sequence 5'-AAAGUG-3,' which is present in each of the miR-17 family members.

"miR-17 family member" means a mature miRNA having a nucleobase sequence comprising the miR-17 seed sequence, and which is selected from miR-17, miR-20a, miR-20b, miR-93, miR-106a, and miR-106b.

"miR-17 family" means the following group of miRNAs: miR-17, miR-20a, miR-20b, miR-93, miR-106a, and miR-106b, each having a nucleobase sequence comprising the miR-17 seed sequence.

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"Nucleobase sequence" means the order of contiguous nucleobases in an oligomeric compound or nucleic acid, typically listed in a 5' to 3' orientation, and independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybridizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary (also referred to as 100% complementary) to a microRNA, i.e. each nucleobase of the oligonucleotide is complementary to a nucleobase at a corresponding position in the microRNA. A modified oligonucleotide may be fully complementary to a microRNA, and have a number of linked nucleosides that is less than the length of the microRNA. For example, an oligonucleotide with 16 linked nucleosides, where each nucleobase of the oligonucleotide is complementary to a nucleobase at a corresponding position in a microRNA, is fully complementary to the microRNA. In certain embodiments, an oligonucleotide wherein each nucleobase has complementarity to a nucleobase within a region of a microRNA stem-loop sequence is fully complementary to the microRNA stem-loop sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in a first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of Watson-Crick pairing with a nucleobase at a corresponding position of a second nucleic acid.

"Identical" in the context of nucleobase sequences, means having the same nucleobase sequence, independent of sugar, linkage, and/or nucleobase modifications and independent of the methylation state of any pyrimidines present.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (microrna.sanger-.ac.uk/). In certain embodiments, microRNA is abbreviated as "miR."

"microRNA-regulated transcript" means a transcript that is regulated by a microRNA.

"Seed match sequence" means a nucleobase sequence that is complementary to a seed sequence, and is the same length as the seed sequence.

"Oligomeric compound" means a compound that comprises a plurality of linked monomeric subunits. Oligomeric compounds include oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the modified oligonucleotide is not hybridized to a complementary strand and the compound does not include any additional nucleosides beyond those of the modified oligonucleotide.

"Modified oligonucleotide" means a single-stranded oligonucleotide having one or more modifications relative to a naturally occurring terminus, sugar, nucleobase, and/or internucleoside linkage. A modified oligonucleotide may comprise unmodified nucleosides.

"Modified nucleoside" means a nucleoside having any change from a naturally occurring nucleoside. A modified nucleoside may have a modified sugar and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar moiety" means substitution and/or any change from a natural sugar.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Non-methylated cytosine" means a cytosine that does not have a methyl group attached to the 5 position.

"Modified nucleobase" means any nucleobase that is not an unmodified nucleobase.

"Sugar moiety" means a naturally occurring furanosyl or a modified sugar moiety.

"Modified sugar moiety" means a substituted sugar moiety or a sugar surrogate.

"2'-O-methyl sugar" or "2'-OMe sugar" means a sugar having an O-methyl modification at the 2' position.

"2'-O-methoxyethyl sugar" or "2'-MOE sugar" means a sugar having an O-methoxyethyl modification at the 2' position.

"2'-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments, the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a $(CH_2)$—O bridge between the 4' and 2' furanose ring atoms.

"ENA sugar moiety" means a substituted sugar moiety comprising a $(CH_2)_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $CH(CH_3)$—O is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methyl nucleoside" means a 2'-modified nucleoside having a 2'-O-methyl sugar modification.

"2'-O-methoxyethyl nucleoside" means a 2'-modified nucleoside having a 2'-O-methoxyethyl sugar modification. A 2'-O-methoxyethyl nucleoside may comprise a modified or unmodified nucleobase.

"2'-fluoro nucleoside" means a 2'-modified nucleoside having a 2'-fluoro sugar modification. A 2'-fluoro nucleoside may comprise a modified or unmodified nucleobase.

"Bicyclic nucleoside" means a 2'-modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

"Hydrogen bond acceptor" means the component of a hydrogen bond that does not supply the shared hydrogen atom.

"Hydrogen bond donor" means the bond or molecule that supplies the hydrogen atom of a hydrogen bond.

Overview

Polycystic kidney disease (PKD) is an inherited form of kidney disease in which fluid-filled cysts develop in the kidneys, leading to renal insufficiency, and often end-stage renal disease. Certain PKDs are also characterized by kidney enlargement. The excessive proliferation of cysts is a hallmark pathological feature of PKD. In the management of PKD, the primary goal for treatment is to manage symptoms such as hypertension and infections, maintain kidney function and prevent the onset of end-stage renal disease (ESRD), which in turn improves life expectancy of subjects with PKD.

miR-17 has been identified as a target for the treatment of PKD. The anti-miR-17 compound RGLS4326 was discovered by screening a chemically diverse and rationally designed library of anti-miR-17 oligonucleotides for optimal pharmaceutical properties. RGLS4326 preferentially distributes to kidney and collecting duct-derived cysts, displaces miR-17 from translationally active polysomes, and de-represses multiple miR-17 mRNA targets including Pkd1 and Pkd2. Importantly, RGLS4326 attenuates cyst growth in human in vitro ADPKD models and multiple PKD mouse models after subcutaneous administration. A phase 1b clinical trial of RGLS4326 for the treatment of patients with autosomal dominant polycystic kidney disease (ADPKD) was initiated in October 2020.

Subsequent to the initiation of the phase 1b clinical trial, nonclinical toxicology studies revealed CNS-related findings, including abnormal gait, reduced motor activity, and/or prostration, at high doses of RGLS4326 in mice. RGLS4326 was found to be an antagonist of the AMPA receptor (AMPA-R), a glutamate receptor and ion channel on excitatory synapses in the central nervous system (CNS) that mediates fast excitatory neurotransmission and, therefore, is a key component of all neuronal networks. Antagonism of the AMPA receptor could explain the CNS-mediated findings observed at high doses of RGLS4326 in nonclinical toxicology models. While no such CNS-related findings were observed in human subjects, it is nonetheless preferable to avoid antagonism of the AMPA receptor. Accordingly, a library of anti-miR-17 compounds was screened to identify compounds with physicochemical and pharmacological properties comparable to RGLS4326, that also have a more favorable safety profile. One such compound, RG-NG-1015, was identified and selected as a candidate therapeutic agent for the treatment of ADPKD.

Compounds

Provided herein is a compound comprising a modified oligonucleotide, wherein the modified oligonucleotide has the following structure in the 5' to 3' orientation:

$$(N'')_p\text{—}(N)_r\text{—}(N')_q$$

wherein each N'' is, independently, a modified or unmodified nucleoside; p is from 0 to 14; wherein if p is not 0, the nucleobase sequence of $(N'')_p$ is complementary to an equal-length portion of the nucleobase sequence of miR-17; each N of $(N)_r$ is, independently, a modified or unmodified nucleotide, and the nucleobase sequence of $(N)_r$ is 5'-AGCACUUU-3'; N' is a nucleoside comprising a modified sugar moiety; q is 0 or 1; wherein if q is 1, the nucleobase of N' is a uracil nucleobase, a cytosine nucleobase, or a purine nucleobase, provided that the purine nucleobase does not have a hydrogen bond acceptor at position 6; and each cytosine is independently selected from a non-methylated cytosine and a 5-methylcytosine; or a pharmaceutically acceptable salt thereof.

The atoms of purine nucleobases are numbered one through nine, according to standard numbering convention for nucleobases, as shown in the following structure:

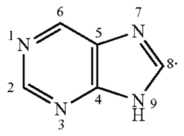

Atoms or groups bonded to the nucleobase ring atom have the same number as the ring atom to which they are bonded.

Certain nucleobases, for example guanosine and inosine, contain hydrogen-bond acceptors at position 6. The hydrogen-bond acceptor at position 6 of guanosine is the oxygen bonded to the position 6 carbon. The hydrogen-bond acceptor at position 6 of inosine is the oxygen bonded to the position 6 carbon.

Purine nucleobases that do not have a hydrogen-bond acceptor at position 6 include, without limitation, 2-aminopurine, 2,6-diaminopurine, isoguanosine, and adenosine. The $NH_2$ present at position 6 of each of 2,6-diaminopurine, isoguanosine, and adenosine functions as a hydrogen-bond donor. Position 6 of 2-aminopurine has no substituent and thus lacks a hydrogen bond acceptor or donor.

In certain embodiments, the structure of $(N)_r$ is: $A_SG_SC_MA_FC_FU_FU_MU_S$, wherein nucleosides followed by subscript "M" are 2'-O-methyl nucleosides; nucleosides followed by subscript "F" are 2'-fluoro nucleosides; and nucleosides followed by subscript "S" are S-cEt nucleosides.

In certain embodiments, at least one internucleoside linkage is a phosphorothioate internucleoside linkage. In certain embodiments, each internucleoside linkage is a phosphorothioate internucleoside linkage.

In certain embodiments, wherein q is 1. In certain embodiments, q is 0. In certain embodiments, p is 0. In certain embodiments, p is selected from 1, 2, 3, 4, 5, 6, 7, 8, 9, 10, 11, 12, 13, or 14.

In certain embodiments, the nucleobase sequence of $(N'')_p$ has no more than one mismatch to the nucleobase sequence of miR-17 (SEQ ID NO: 1). In certain embodiments, the nucleobase sequence of $(N'')_p$ has no mismatches to the nucleobase sequence of miR-17 (SEQ ID NO: 1). In certain embodiments, the nucleobase sequence of $(N'')_p$ is selected from CUACCUGCACUGUA (SEQ ID NO: 7), CUACCUGCACUGU (SEQ ID NO: 8), CUACCUGCACUG (SEQ ID NO: 9), CUACCUGCACU (SEQ ID NO: 10), CUACCUGCAC (SEQ ID NO: 11), CUACCUGCA, CUACCUGC, CUACCUG, CUACCU, CUACC, CUAC, CUA, CU, and C.

In certain embodiments, the nucleobase of N' is a purine nucleobase that does not have a hydrogen bond acceptor at position 6. In certain embodiments, the nucleobase of N' is selected from adenosine, 2-aminopurine, 2,6-diaminopurine, and isoguanosine.

In certain embodiments, the sugar moiety of N' is not a 2-O-methyl sugar. In certain embodiments, the sugar moiety of N' is a 2'-O-methoxyethyl sugar or an S-cEt sugar.

In certain embodiments, the structure of the modified oligonucleotide is 5'-$A_SG_SC_MA_FC_FU_FU_MU_SA_S$-3', wherein each cytosine is a non-methylated cytosine. In certain embodiments, the structure of the modified oligonucleotide is 5'-$A_SG_SC_MA_FC_FU_FU_MU_SU_S$-3', wherein each cytosine is a non-methylated cytosine. In certain embodiments, the structure of the modified oligonucleotide is 5'-$A_SG_SC_MA_FC_FU_FU_MU_SC_S$-3', wherein each cytosine is a non-methylated cytosine. The compound of claim 2, wherein the structure of the modified oligonucleotide is 5'-$A_SG_SC_MA_FC_FU_FU_MU_S$-3', wherein each cytosine a non-methylated cytosine.

In certain embodiments, the compound consists of the modified oligonucleotide.

In certain embodiments, the pharmaceutically acceptable salt is a sodium salt.

Provided herein is a modified oligonucleotide having the structure:

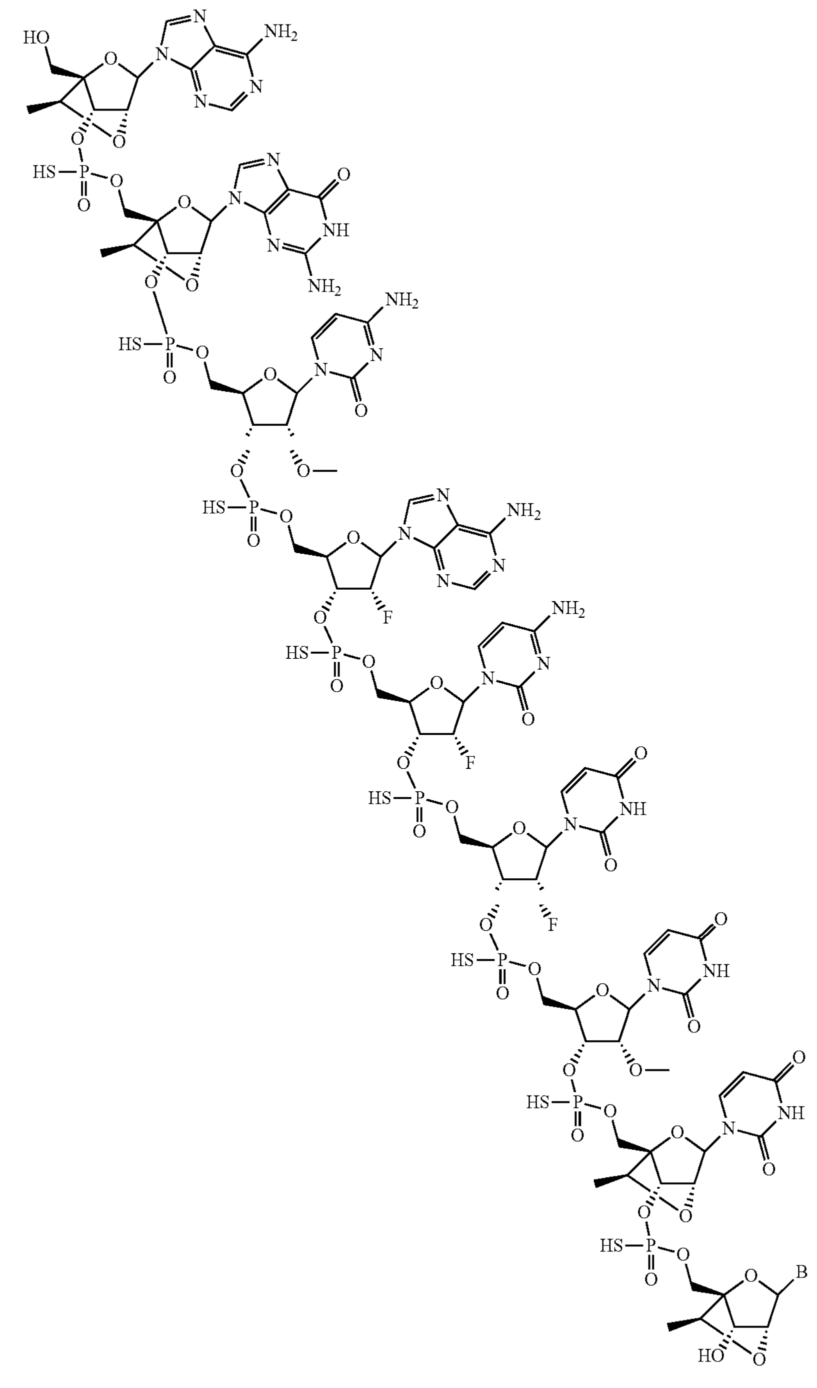

wherein B is a uridine nucleobase, a cytosine nucleobase, or a purine nucleobase, provided that the purine nucleobase does not have a hydrogen bond acceptor at position 6; or a pharmaceutically acceptable salt thereof. In certain embodiments, B is selected from adenosine, 2-aminopurine, 2,6-diaminopurine, and isoguanosine.

Provided herein is a modified oligonucleotide having the structure:

wherein B is a uridine nucleobase, a cytosine nucleobase, or a purine nucleobase, provided that the purine nucleobase does not have a hydrogen bond acceptor at position 6. In certain embodiments, B is selected from adenosine, 2-aminopurine, 2,6-diaminopurine, and isoguanosine.

Provided herein is a modified oligonucleotide named RG-NG-1015, wherein the structure of the modified oligonucleotide is:

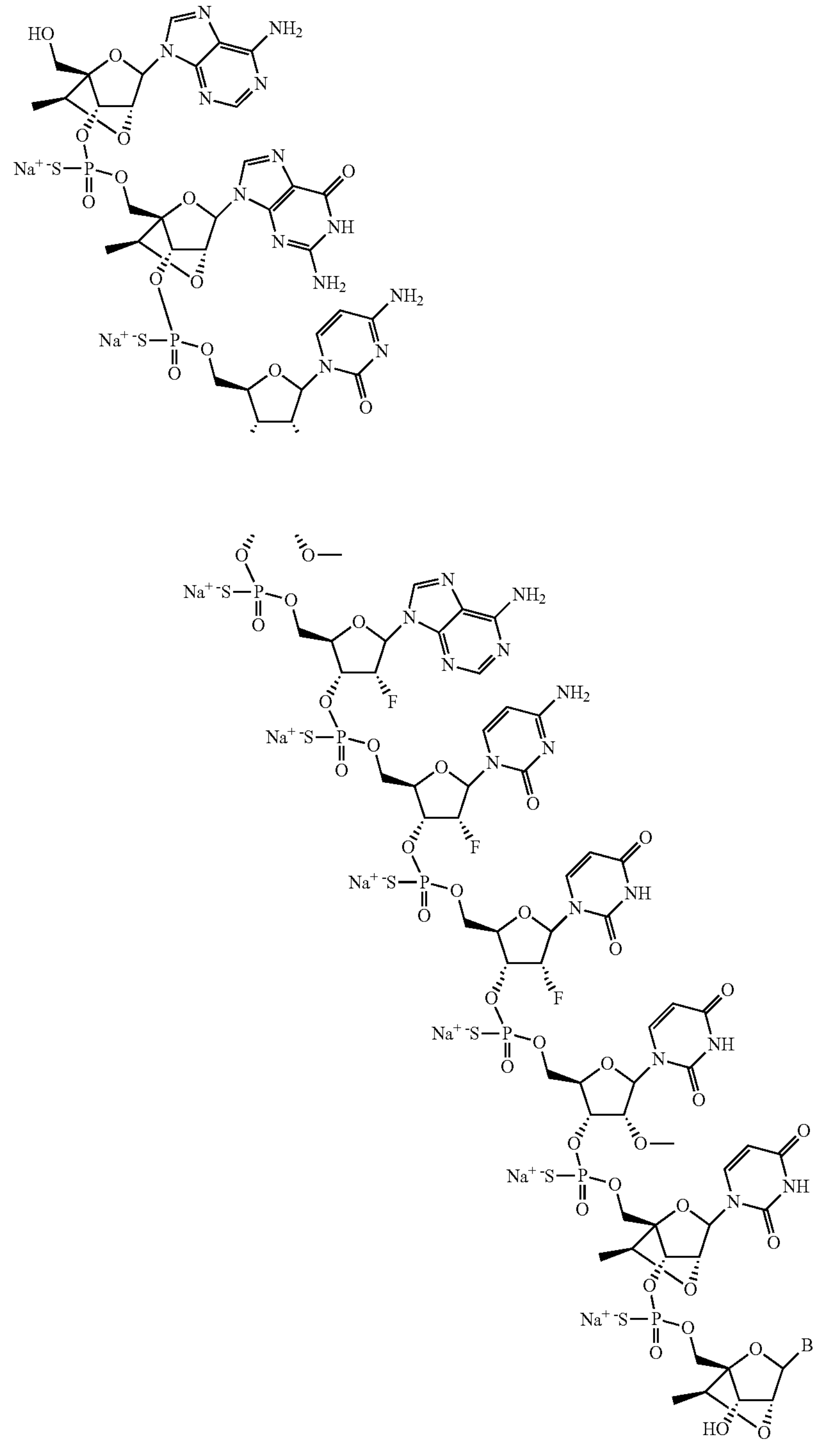

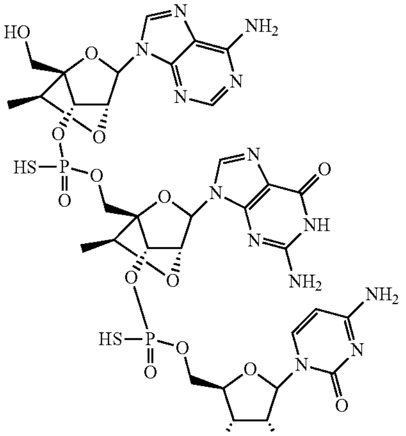
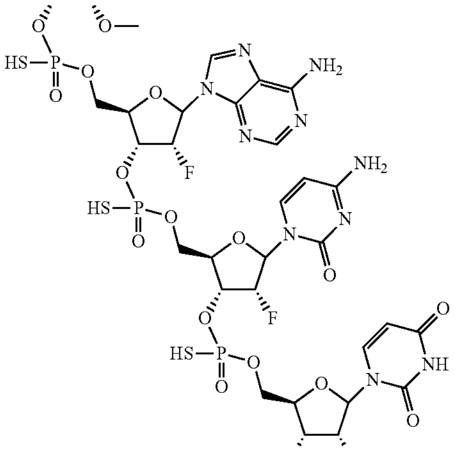
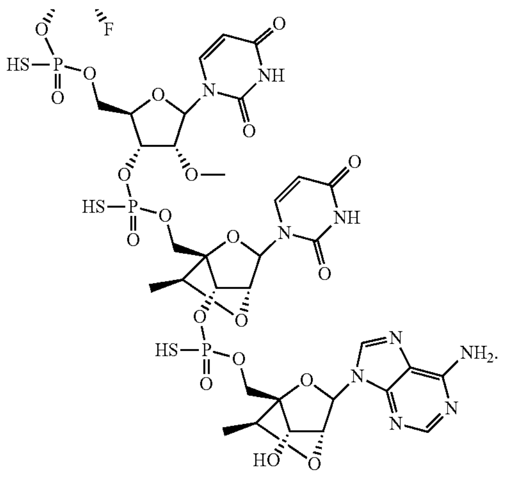

Provided herein are also pharmaceutically acceptable salts of modified oligonucleotide RG-NG-1015. Thus, in some embodiments, a modified oligonucleotide has the structure:
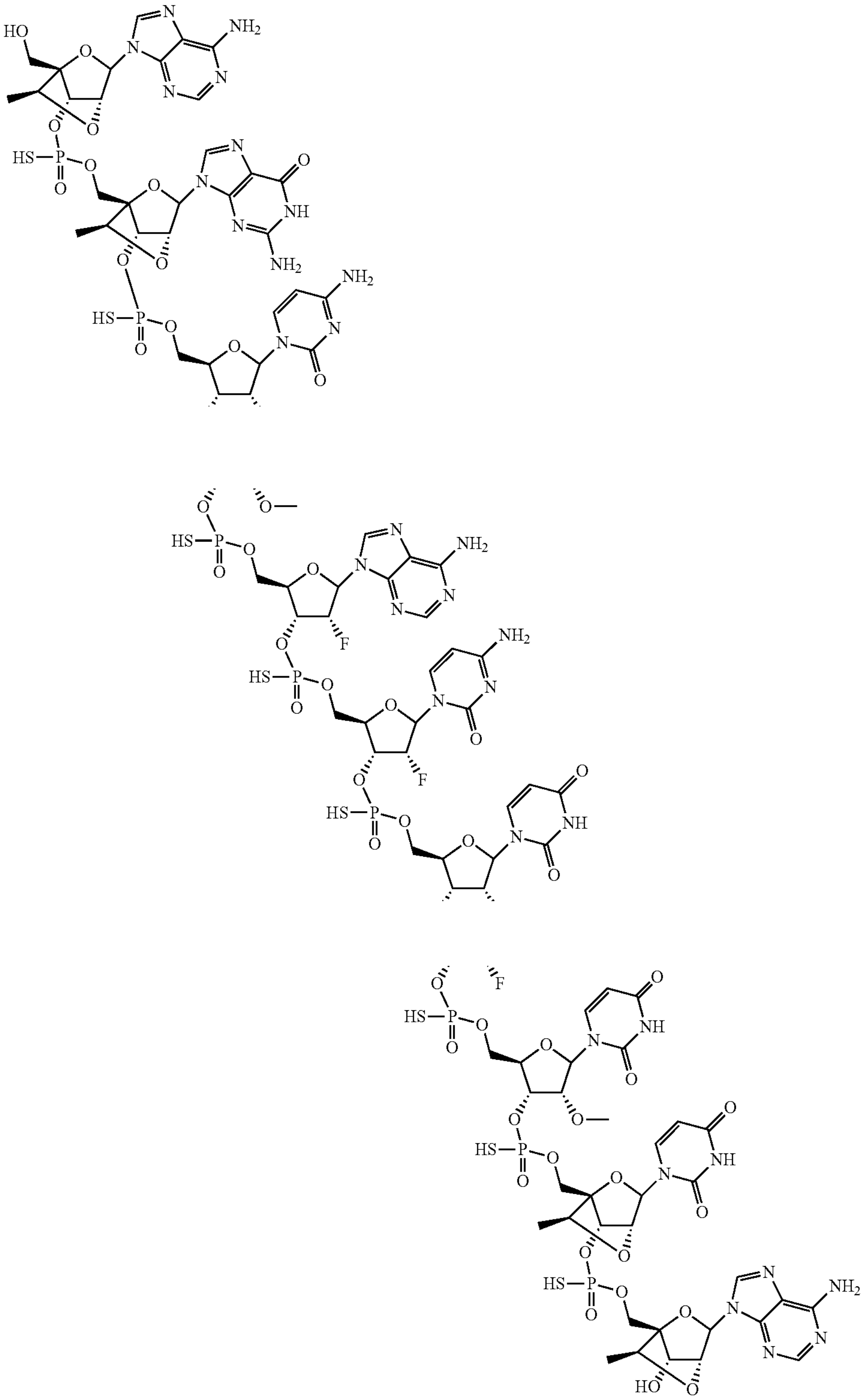
or a pharmaceutically acceptable salt thereof. A nonlimiting exemplary pharmaceutically acceptable salt of RG-NG-1015 has the structure:

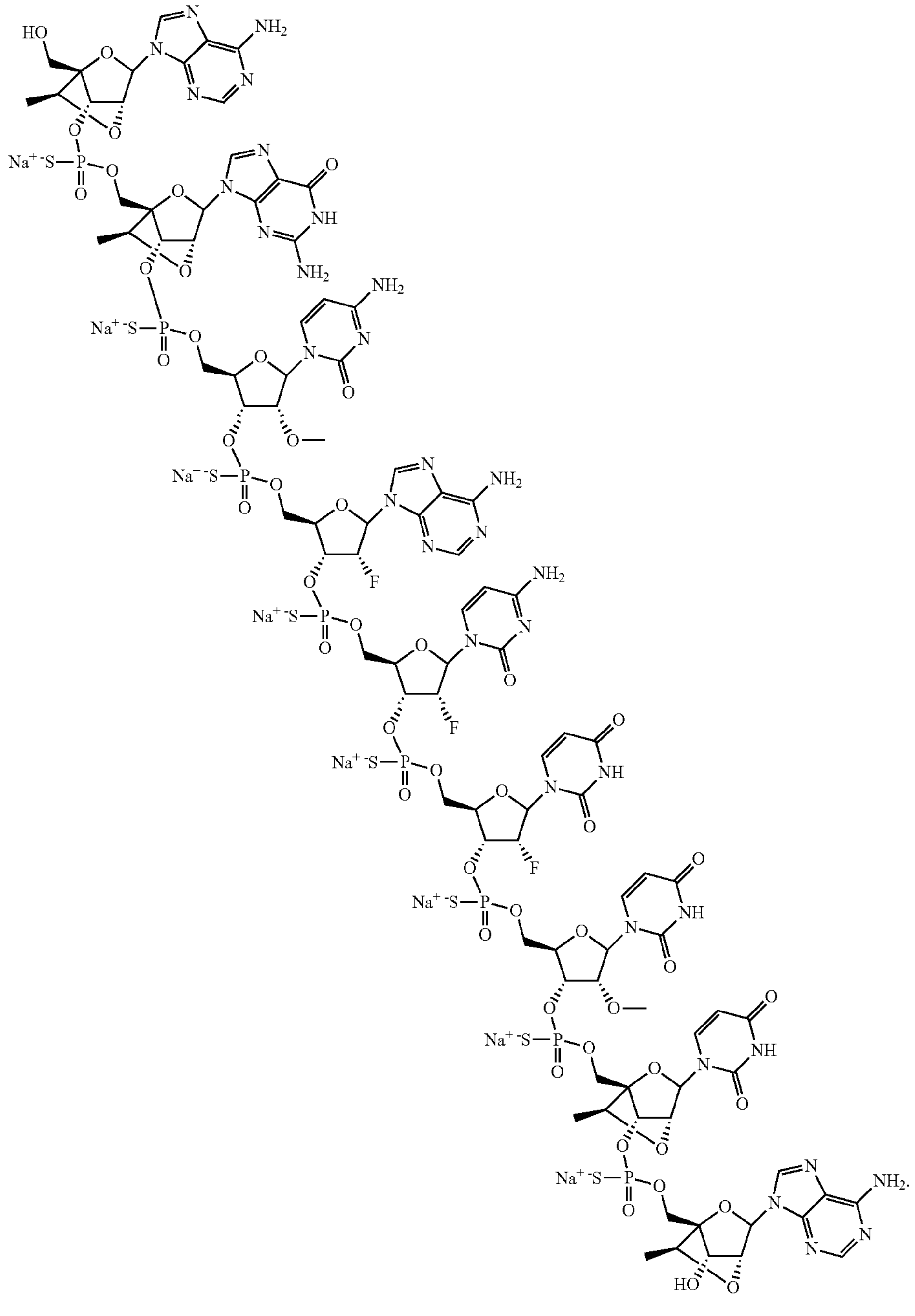

In some embodiments, a pharmaceutically acceptable salt of a modified oligonucleotide comprises fewer cationic counterions (such as $Na^+$) than there are phosphorothioate and/or phosphodiester linkages per molecule (i.e., some phosphorothioate and/or phosphodiester linkages are protonated). In some embodiments, a pharmaceutically acceptable salt of RG-NG-1015 comprises fewer than 8 cationic counterions (such as $Na^+$) per molecule of RG-NG-1015. That is, in some embodiments, a pharmaceutically acceptable salt of RG-NG-1015 may comprise, on average, 1, 2, 3, 4, 5, 6, or 7 cationic counterions per molecule of RG-NG-1015, with the remaining phosphorothioate groups being protonated.

Certain Uses

Provided herein are methods for inhibiting the activity of one or more members of the miR-17 family in a cell, comprising contacting a cell with a compound provided herein, which comprises a nucleobase sequence complementary to the miR-17 seed sequence.

Provided herein are methods for inhibiting the activity of one or more members of the miR-17 family in a subject, comprising administering to the subject a pharmaceutical composition provided herein. In certain embodiments, the subject has a disease associated with one or more members of the miR-17 family.

Provided herein are methods for the treatment of polycystic kidney disease (PKD), comprising administering to a subject in need thereof a compound provided herein, which comprises a nucleobase sequence complementary to the miR-17 seed sequence. In certain embodiments, the subject has a polycystic kidney disease. In certain embodiments, the polycystic kidney disease is selected from autosomal dominant polycystic kidney disease (ADPKD), autosomal recessive polycystic kidney disease (ARPKD), and nephronophthisis (NPHP). In certain embodiments, the polycystic kidney disease is selected from autosomal dominant polycystic kidney disease (ADPKD) and autosomal recessive polycystic kidney disease (ARPKD).

In certain embodiments, the subject has a disorder that is characterized by multiple non-renal indicators, and also by polycystic kidney disease. Such disorders include, for example, Joubert syndrome and related disorders (JSRD). Meckel syndrome (MKS), or Bardet-Biedl syndrome (BBS). Accordingly, provided herein are methods for the treatment of polycystic kidney disease (PKD), comprising administering to a subject a compound provided herein, which comprises a nucleobase sequence complementary to the miR-17 seed sequence, wherein the subject has Joubert syndrome and related disorders (JSRD), Meckel syndrome (MKS), or Bardet-Biedl syndrome (BBS). Provided herein are methods for the treatment of polycystic kidney disease (PKD), comprising administering a compound provided herein, which comprises a nucleobase sequence complementary to the miR-17 seed sequence, wherein the subject is suspected of having Joubert syndrome and related disorders (JSRD), Meckel syndrome (MKS), or Bardet-Biedl syndrome (BBS).

In certain embodiments, the polycystic kidney disease is autosomal dominant polycystic kidney disease (ADPKD). ADPKD is caused by mutations in the PKD1 or PKD2 gene. ADPKD is a progressive disease in which cyst formation and renal enlargement lead to renal insufficiency and eventually end-stage renal disease in 50% of patients by age 60. ADPKD patients may require lifelong dialysis and/or kidney transplant. ADPKD is the most frequent genetic cause of kidney failure. The excessive proliferation of cysts is a hallmark pathological feature of ADPKD. In the management of PKD, the primary goal for treatment is to maintain kidney function and prevent the onset of end-stage renal disease (ESRD), which in turn improves life expectancy of subjects with PKD. Total kidney volume generally increases steadily in ADPKD patients, with increases correlating with a decline in kidney function. Provided herein are methods for the treatment of ADPKD, comprising administering to a subject having or suspected of having ADPKD a compound provided herein, which comprises a nucleobase sequence complementary to the miR-17 seed sequence.

In certain embodiments, the polycystic kidney disease is autosomal recessive polycystic kidney disease (ARPKD). ARPKD is caused by mutations in the PKHD1 gene, and is a cause of chronic kidney disease in children. A typical renal phenotype of ARPKD is enlarged kidneys; however, ARPKD has notable effects on other organs, particularly the liver. Patients with ARPKD progress to end-stage renal disease and require a kidney transplant as young as 15 years of age. Provided herein are methods for the treatment of ARPKD, comprising administering to a subject having or suspected of having ARPKD a compound provided herein, which comprises a nucleobase sequence complementary to the miR-17 seed sequence.

In certain embodiments, the polycystic kidney disease is nephronophthisis (NPHP). Nephronophthisis is an autosomal recessive cystic kidney disease that is a frequent cause of ESRD in children. NPHP is characterized by kidneys of normal or reduced size, cysts concentrated at the corticomedullary junction, and tubulointerstitial fibrosis. Mutations in one of several NPHP genes, for example. NPHP1, have been identified in patients with NPHP. Provided herein are methods for the treatment of NPHP, comprising administering to a subject having or suspected of having NPHP a compound provided herein, which comprises a nucleobase sequence complementary to the miR-17 seed sequence.

In certain embodiments, a subject having polycystic kidney disease has Joubert syndrome and related disorders (JSRD). JSRD includes a broad range of hallmark features, including brain, retinal, and skeletal abnormalities. Certain subjects with JSRD have polycystic kidney disease, in addition to hallmark features of JSRD. Accordingly, provided herein are methods for the treatment of polycystic kidney disease in a subject having JSRD, comprising administering to a subject having JSRD a compound provided herein, which comprises a nucleobase sequence complementary to the miR-17 seed sequence. In certain embodiments, a subject is suspected of having JSRD.

In certain embodiments, a subject having polycystic kidney disease has Meckel syndrome (MKS). MKS is a disorder with severe signs and symptoms in many parts of the body, including the central nervous system, skeletal system, liver, kidney, and heart. Common features of MKS is the presence of numerous fluid-filled cysts in the kidney, and kidney enlargement. Accordingly, provided herein are methods for the treatment of MKS, comprising administering to a subject having MKS a compound provided herein, which comprises a nucleobase sequence complementary to the miR-17 seed sequence. In certain embodiments, the subject is suspected of having MKS.

In certain embodiments, a subject having polycystic kidney disease has Bardet-Biedl syndrome (BBS). BBS is disorder affecting many parts of the body, including the eye, heart, kidney, liver and digestive system. A hallmark feature of BBS is the presence of renal cysts. Accordingly, provided herein are methods for the treatment of polycystic kidney disease in a subject having BBS, comprising administering to a subject having BBS a compound provided herein, which comprises a nucleobase sequence complementary to the miR-17 seed sequence. In certain embodiments, the subject is suspected of having BBS.

In certain embodiments, the subject has been diagnosed as having PKD prior to administration of the compound comprising the modified oligonucleotide. Diagnosis of PKD may be achieved through evaluation of parameters including, without limitation, a subject's family history, clinical features (including without limitation hypertension, albuminuria, hematuria, and impaired GFR), kidney imaging studies (including without limitation MRI, ultrasound, and CT scan), and/or histological analysis.

In certain embodiments, diagnosis of PKD includes screening for mutations in one or more of the PKD1 or PKD2 genes. In certain embodiments, diagnosis of ARPKD includes screening for mutations in the PKHP1 gene. In certain embodiments, diagnosis of NPHP includes screening for one or more mutations in one or more of the NPHP1, NPHP2, NPHP3, NPHP4, NPHP5, NPHP6, NPHP7, NPHP8, or NPHP9 genes. In certain embodiments, diagnosis of JSRD includes screening for mutations in the NPHP1, NPHP6, AHI1, MKS3, or RPGRIP1L genes. In certain embodiments, diagnosis of MKS includes screening for mutations in the NPHP6, MKS3, RPGRIP1L, NPHP3, CC2D2A, BBS2, BBS4, BBS6, or MKS1 genes. In certain embodiments, diagnosis of BBS includes screening for mutations in BBS2, BBS4, BBS6, MKS1, BBS1, BBS3, BBS5, BBS7, BBS7, BBS8, BBS9, BBS10, BBS11, or BBS12 genes.

In certain embodiments, the subject has an increased total kidney volume. In certain embodiments, the total kidney volume is height-adjusted total kidney volume (HtTKV). In certain embodiments, the subject has hypertension. In certain embodiments, the subject has impaired kidney function. In certain embodiments, the subject is in need of improved kidney function. In certain embodiments, the subject is identified as having impaired kidney function.

In certain embodiments, levels of one or more miR-17 family members are increased in the kidney of a subject having PKD. In certain embodiments, prior to administration, a subject is determined to have an increased level of one or more miR-17 family members in the kidney. The level of a miR-17 family member may be measured from kidney biopsy material. In certain embodiments, prior to administration, a subject is determined to have an increased level of one or more miR-17 family members in the urine or blood of the subject. In certain embodiments, prior to administration, a subject is determined to have a decreased level of polycystin-1 (PC1) or polycystin-2 (PC2) in the urine of the subject. In certain embodiments, prior to administration, a subject is determined to have a decreased level of polycystin-1 (PCI) or polycystin-2 (PC2) in the urine of the subject. In certain embodiments, prior to administration, a subject is determined to have a decreased level of polycystin-1 (PC1) and/or polycystin-2 (PC2) in the urine of the subject.

In any of the embodiments provided herein, a subject may undergo certain tests to diagnose polycystic kidney disease in the subject, for example, to determine the cause of the polycystic kidney disease, to evaluate the extent of polycystic kidney disease in the subject, and/or to determine the subject's response to treatment. Such tests may assess markers of polycystic kidney disease. Certain of these tests, such as glomerular filtration rate and blood urea nitrogen level, are also indicators of kidney function. Markers of polycystic disease include, without limitation: measurement of total kidney volume in the subject; measurement of hypertension in the subject; assessment of kidney pain the in the subject; measurement of fibrosis in the subject; measurement of polycystin-1 (PC1) in the urine of the subject; measurement of polycystin-2 (PC2) in the urine of the subject; measurement of blood urea nitrogen level in the subject; measurement of serum creatinine level in the subject; measuring creatinine clearance in the subject; measuring albuminuria in the subject; measuring albumin:creatinine ratio in the subject; measuring glomerular filtration rate in the subject; measuring hematuria in the subject; measurement of NGAL protein in the urine of the subject; and/or measurement of KIM-1 protein in the urine of the subject. Unless indicated otherwise herein, blood urea nitrogen level, serum creatinine level, creatinine clearance, albuminuria, albumin:creatinine ratio, glomerular filtration rate, and hematuria refer to a measurement in the blood (such as whole blood or serum) of a subject.

Markers of polycystic kidney disease are determined by laboratory testing. The reference ranges for individual markers may vary from laboratory to laboratory. The variation may be due to, for example, differences in the specific assays used. Thus, the upper and lower limits of the normal distribution of the marker within a population, also known as the upper limit of normal (ULN) and lower limit of normal (LLN), respectively, may vary from laboratory to laboratory. For any particular marker, a health professional may determine which levels outside of the normal distribution are clinically relevant and/or indicative of disease. For example, a health professional may determine the glomerular filtration rate that may be indicative of a decline in the rate of kidney function in a subject with polycystic kidney disease.

In certain embodiments, administration of a compound provided herein results in one or more clinically beneficial outcomes. In certain embodiments, the administration improves kidney function in the subject. In certain embodiments, the administration slows the rate of decline of kidney function in the subject. In certain embodiments, the administration reduces total kidney volume in the subject. In certain embodiments, the administration slows the rate of increase in total kidney volume in the subject. In certain embodiments, the administration reduces height-adjusted total kidney volume (HtTKV). In certain embodiments, the administration slows the rate of increase in HtTKV.

In certain embodiments, the administration increases polycystin-1 (PC1) in the urine of the subject. In certain embodiments, the administration increases polycystin-2 (PC2) in the urine of the subject. In certain embodiments, the administration increases polycystin-1 (PC1) and polycystin-2 (PC2) in the urine of the subject.

In certain embodiments, the administration inhibits cyst growth in the subject. In certain embodiments, the administration slows rate of increase in cyst growth in the subject. In some embodiments, a cyst is present in the kidney of a subject. In some embodiments, a cyst is present in an organ other than the kidney, for example, the liver.

In certain embodiments, the administration alleviates kidney pain in the subject. In certain embodiments, the administration slows the increase in kidney pain in the subject. In certain embodiments, the administration delays the onset of kidney pain in the subject.

In certain embodiments, the administration reduces hypertension in the subject. In certain embodiments, the administration slows the worsening of hypertension in the subject. In certain embodiments, the administration delays the onset of hypertension in the subject.

In certain embodiments, the administration reduces fibrosis in kidney of the subject. In certain embodiments, the administration slows the worsening of fibrosis in the kidney of the subject.

In certain embodiments, the administration delays the onset of end stage renal disease in the subject. In certain embodiments, the administration delays time to dialysis for the subject. In certain embodiments, the administration delays time to renal transplant for the subject. In certain embodiments, the administration improves life expectancy of the subject.

In certain embodiments, the administration reduces albuminuria in the subject. In certain embodiments, the administration slows the worsening of albuminuria in the subject. In certain embodiments, the administration delays the onset of albuminuria in the subject. In certain embodiments, the administration reduces hematuria in the subject. In certain embodiments, the administration slows the worsening of hematuria in the subject. In certain embodiments, the administration delays the onset of hematuria in the subject. In certain embodiments, the administration reduces blood urea nitrogen level in the subject. In certain embodiments, the administration reduces serum creatinine level in the subject. In certain embodiments, the administration improves creatinine clearance in the subject. In certain embodiments, the administration reduces albumin:creatinine ratio in the subject.

In certain embodiments, the administration improves glomerular filtration rate in the subject. In certain embodiments, the administration slows the rate of decline of glomerular filtration rate in the subject. In certain embodiments, the glomerular filtration rate is an estimated glomerular filtration rate (eGFR). In certain embodiments, the glomerular filtration rate is a measured glomerular filtration rate (mGFR).

In certain embodiments, the administration reduces neutrophil gelatinase-associated lipocalin (NGAL) protein in the urine of the subject. In certain embodiments, the administration reduces kidney injury molecule-1 (KIM-1) protein in the urine of the subject.

In any of the embodiments, provided herein, a subject may be subjected to certain tests to evaluate the extent of disease in the subject. Such tests include, without limitation, measurement of total kidney volume in the subject; measurement of hypertension in the subject; measurement of kidney pain in the subject; measurement of fibrosis in the kidney of the subject; measurement of blood urea nitrogen level in the subject; measuring serum creatinine level in the subject; measuring creatinine clearance in the blood of the subject; measuring albuminuria in the subject; measuring albumin:creatinine ratio in the subject; measuring glomerular filtration rate in the subject, wherein the glomerular filtration rate is estimated or measured; measurement of neutrophil gelatinase-associated lipocalin (NGAL) protein in the urine of the subject; and/or measurement of kidney injury molecule-1 (KIM-1) protein in the urine of the subject.

In certain embodiments, a subject having polycystic kidney disease experiences a reduced quality of life. For example, a subject having polycystic kidney disease may experience kidney pain, which may reduce the subject's quality of life. In certain embodiments, the administration improves the subject's quality of life.

In any of the embodiments provided herein, the subject is a human subject. In certain embodiments, the human subject is an adult. In certain embodiments, an adult is at least 21 years of age. In certain embodiments, the human subject is a pediatric subject, i.e, the subject is less than 21 years of age. Pediatric populations may be defined by regulatory agencies. In certain embodiments, the human subject is an adolescent. In certain embodiments, an adolescent is at least 12 years of age and less than 21 years of age. In certain embodiments, the human subject is a child. In certain embodiments, a child is at least two years of age and less than 12 years of age. In certain embodiments, the human subject is an infant. In certain embodiments, and infant is at least one month of age and less than two years of age. In certain embodiments, the subject is a newborn. In certain embodiments, a newborn is less than one month of age.

Any of the compounds described herein may be for use in therapy. Any of the compounds provided herein may be for use in the treatment of polycystic kidney disease. In certain embodiments, the polycystic kidney disease is autosomal dominant polycystic kidney disease. In certain embodiments, the polycystic kidney disease is autosomal recessive polycystic kidney disease. In certain embodiment, the polycystic kidney disease is nephronophthisis. In certain embodiments, the subject has Joubert syndrome and related disorders (JSRD), Meckel syndrome (MKS), or Bardet-Biedl syndrome (BBS).

Any of the modified oligonucleotides described herein may be for use in therapy. Any of the modified oligonucleotides provided herein may be for use in the treatment of polycystic kidney disease.

Any of the compounds provided herein may be for use in the preparation of a medicament. Any of the compounds provided herein may be for use in the preparation of a medicament for the treatment of a polycystic kidney disease.

Any of the modified oligonucleotides provided herein may be for use in the preparation of a medicament. Any of the modified oligonucleotides provided herein may be for use in the preparation of a medicament for the treatment of polycystic kidney disease.

Any of the pharmaceutical compositions provided herein may be for use in the treatment of polycystic kidney disease.

Certain Additional Therapies

Treatments for polycystic kidney disease or any of the conditions listed herein may comprise more than one therapy. As such, in certain embodiments, provided herein are methods for treating a subject having or suspected of having polycystic kidney disease comprising administering at least one therapy in addition to administering compound provided herein, which comprises a nucleobase sequence complementary to the miR-17 seed sequence.

In certain embodiments, the at least one additional therapy comprises a pharmaceutical agent. In certain embodiments, a pharmaceutical agent is an anti-hypertensive agent. Anti-hypertensive agents are used to control blood pressure of the subject.

In certain embodiments, a pharmaceutical agent is a vasopressin receptor 2 antagonist. In certain embodiments, a vasopressin receptor 2 antagonist is tolvaptan.

In certain embodiments, pharmaceutical agents include angiotensin II receptor blockers (ARB). In certain embodiments, an angiotensin II receptor blocker is candesartan, irbesartan, olmesartan, losartan, valsartan, telmisartan, or eprosartan.

In certain embodiments, pharmaceutical agents include angiotensin II converting enzyme (ACE) inhibitors. In certain embodiments, an ACE inhibitor is captopril, enalapril, lisinopril, benazepril, quinapril, fosinopril, or ramipril.

In certain embodiments, a pharmaceutical agent is a diuretic. In certain embodiments, a pharmaceutical agent is a calcium channel blocker.

In certain embodiments, a pharmaceutical agent is a glucosylceramide synthase inhibitor. In certain embodiments, a glucosylceramide synthase inhibitor is venglustat.

In certain embodiments, a pharmaceutical agent is an antihyperglycemic agent. In certain embodiments, an antihyperglycemic agent is a biguanide. In certain embodiments, a biguanide is metformin.

In certain embodiments, a pharmaceutical agent is a kinase inhibitor. In certain embodiments, a kinase inhibitor is bosutinib or KD019.

In certain embodiments, a pharmaceutical agent is an adrenergic receptor antagonist.

In certain embodiments, a pharmaceutical agent is an aldosterone receptor antagonist. In certain embodiments, an aldosterone receptor antagonist is spironolactone. In certain embodiments, spironolactone is administered at a dose ranging from 10 to 35 mg daily. In certain embodiments, spironolactone is administered at a dose of 25 mg daily.

In certain embodiments, a pharmaceutical agent is a mammalian target of rapamycin (mTOR) inhibitor. In certain embodiments, an mTOR inhibitor is everolimus, rapamycin, or sirolimus.

In certain embodiments, a pharmaceutical agent is a hormone analogue. In certain embodiments, a hormone analogue is somatostatin or adrenocorticotrophic hormone.

In certain embodiments, a pharmaceutical agent is an anti-fibrotic agent. In certain embodiments, an anti-fibrotic agent is a modified oligonucleotide complementary to miR-21.

In certain embodiments, an additional therapy is dialysis. In certain embodiments, an additional therapy is kidney transplant.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid is prednisone. In certain embodiments, an anti-inflammatory agent is a non-steroidal anti-inflammatory drug. In certain embodiments, a non-steroidal anti-inflammatory agent is ibuprofen, a COX-I inhibitor, or a COX-2 inhibitor.

In certain embodiments, a pharmaceutical agent is a pharmaceutical agent that blocks one or more responses to fibrogenic signals.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain embodiments, the additional therapy is selected to treat or ameliorate a side effect of one or more pharmaceutical compositions provided herein. Such side effects include, without limitation, injection site reactions, liver function test abnormalities, kidney function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Certain MicroRNA Nucleobase Sequences

The miR-17 family includes miR-17, miR-20a, miR-20b, miR-93, miR-106a, and miR-106b. Each member of the miR-17 family has a nucleobase sequence comprising the nucleobase sequence 5'-AAAGUG-3, or the miR-17 seed sequence, which is the nucleobase sequence at positions 2 through 7 of SEQ ID NO: 1. Additionally, each member of the miR-17 family shares some nucleobase sequence identity outside the seed region. Accordingly, a modified oligonucleotide comprising a nucleobase sequence complementary to the miR-17 seed sequence may target other microRNAs of the miR-17 family, in addition to miR-17. In certain embodiments, a modified oligonucleotide targets two or more microRNAs of the miR-17 family. In certain embodiments, a modified oligonucleotide targets three or more microRNAs of the miR-17 family. In certain embodiments, a modified oligonucleotide targets four or more microRNAs of the miR-17 family. In certain embodiments, a modified oligonucleotide targets five or more microRNAs of the miR-17 family. In certain embodiments, a modified oligonucleotide targets six of the microRNAs of the miR-17 family. For example, a modified oligonucleotide which has the nucleobase sequence 5'-AGCACUUU-3' targets all members of the miR-17 family.

In certain embodiments, a modified oligonucleotide comprises the nucleobase sequence 5'-CACUUU-3'. In certain embodiments, a modified oligonucleotide comprises the nucleobase sequence 5-AGCACUUU-3'.

In certain embodiments, a modified oligonucleotide comprises the nucleobase sequence 5'-CACUUUX-3', wherein X is a uracil nucleobase, a cytosine nucleobase, or a purine nucleobase, provided that the purine nucleobase does not have a hydrogen bond acceptor at position 6. In certain embodiments, a modified oligonucleotide comprises the nucleobase sequence 5'-GCACUUUX-3', wherein X is a uracil nucleobase, a cytosine nucleobase, or a purine nucleobase, provided that the purine nucleobase does not have a hydrogen bond acceptor at position 6. In certain embodiments, a modified oligonucleotide comprises the nucleobase sequence 5'-AGCACUUUX-3', wherein X is a uracil nucleobase, a cytosine nucleobase, or a purine nucleobase, provided that the purine nucleobase does not have a hydrogen bond acceptor at position 6. In certain embodiments, a modified oligonucleotide is the nucleobase sequence 5'-AGCACUUUX-3', wherein X is a uracil nucleobase, a cytosine nucleobase, or a purine nucleobase, provided that the purine nucleobase does not have a hydrogen bond acceptor at position 6.

In certain embodiments, a modified oligonucleotide comprises the nucleobase sequence 5'-AGCACUUUA-3'. In certain embodiments, a modified oligonucleotide comprises the nucleobase sequence 5'-AGCACUUU-3'. In certain embodiments, a modified oligonucleotide comprises the nucleobase sequence 5'-AGCACUU-3'. In certain embodiments, a modified oligonucleotide comprises the nucleobase sequence 5'-AGCACU-3'. In certain embodiments, a modified oligonucleotide comprises the nucleobase sequence 5'-AGCAC-3'. In certain embodiments, a modified oligonucleotide comprises the nucleobase sequence 5'-AGCA-3'. In certain embodiments, a modified oligonucleotide comprises the nucleobase sequence 5'-GCACUUUA-3'. In certain embodiments, a modified oligonucleotide comprises the nucleobase sequence 5'-CACUUUA-3'. In certain embodiments, a modified oligonucleotide comprises the nucleobase sequence 5'-ACUUUA-3'. In certain embodiments, a modified oligonucleotide comprises the nucleobase sequence 5'-CUUUA-3'. In certain embodiments, a modified oligonucleotide comprises the nucleobase sequence 5'-AAGCACUUUA-3'.

In certain embodiments, a modified oligonucleotide comprises the nucleobase sequence 5'-CACTTT-3'. In certain embodiments, a modified oligonucleotide comprises the nucleobase sequence 5'-CACUTT-3'. In certain embodiments, a modified oligonucleotide comprises the nucleobase sequence 5'-CACUUT-3'. In certain embodiments, a modified oligonucleotide comprises the nucleobase sequence 5'-CACTUT-3'. In certain embodiments, a modified oligonucleotide comprises the nucleobase sequence 5'-CACUTT-3'. In certain embodiments, a modified oligonucleotide comprises the nucleobase sequence 5'-CACTTU-3'.

In certain embodiments, each cytosine is independently selected from a non-methylated cytosine and a 5-methylcytosine. In certain embodiments, at least one cytosine is a non-methylated cytosine. In certain embodiments, each cytosine is a non-methylated cytosine. In certain embodiments, at least one cytosine is a 5-methylcytosine. In certain embodiments, each cytosine is a 5-methyl cytosine.

In certain embodiments, the number of linked nucleosides of a modified oligonucleotide is less than the length of its target microRNA. A modified oligonucleotide having a number of linked nucleosides that is less than the length of the target microRNA, wherein each nucleobase of the modified oligonucleotide is complementary to a nucleobase at a corresponding position of the target microRNA, is considered to be a modified oligonucleotide having a nucleobase sequence that is fully complementary (also referred to as 100% complementary) to a region of the target microRNA sequence. For example, a modified oligonucleotide consisting of 9 linked nucleosides, where each nucleobase is complementary to a corresponding position of miR-17, is fully complementary to miR-17.

In certain embodiments, a modified oligonucleotide has a nucleobase sequence having one mismatch with respect to the nucleobase sequence of a target microRNA. In certain embodiments, a modified oligonucleotide has a nucleobase sequence having two mismatches with respect to the nucleobase sequence of a target microRNA. In certain such embodiments, a modified oligonucleotide has a nucleobase sequence having no more than two mismatches with respect to the nucleobase sequence of a target microRNA. In certain such embodiments, the mismatched nucleobases are contiguous. In certain such embodiments, the mismatched nucleobases are not contiguous.

Although the sequence listing accompanying this filing identifies each nucleobase sequence as either "RNA" or "DNA" as required, in practice, those sequences may be modified with a combination of chemical modifications specified herein. One of skill in the art will readily appreciate that in the sequence listing, such designation as "RNA" or "DNA" to describe modified oligonucleotides is somewhat arbitrary. For example, a modified oligonucleotide comprising a nucleoside comprising a 2'-O-methoxyethyl sugar moiety and a thymine base may described as a DNA residue in the sequence listing, even though the nucleoside is modified and is not a natural DNA nucleoside.

Accordingly, nucleic acid sequences provided in the sequence listing are intended to encompass nucleic acids containing any combination of natural or modified RNA and/or DNA, including, but not limited to such nucleic acids having modified nucleobases. By way of further example and without limitation, a modified oligonucleotide having the nucleobase sequence "ATCGATCG" in the sequence listing encompasses any oligonucleotide having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a 5-methylcytosine.

Certain Modifications

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides.

In certain embodiments, a modified nucleoside is a sugar-modified nucleoside. In certain such embodiments, the sugar-modified nucleosides may further comprise a natural or modified heterocyclic base moiety and/or may be connected to another nucleoside through a natural or modified internucleoside linkage and/or may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

Nucleosides comprising such bicyclic sugar moieties are referred to as bicyclic nucleosides or BNAs. In certain embodiments, bicyclic nucleosides include, but are not limited to, (A) α-L-methyleneoxy ($4'-CH_2—O-2'$) BNA; (B) β-D-methyleneoxy ($4'-CH_2—O-2'$) BNA; (C) ethyleneoxy ($4'-(CH_2)_2—O-2'$) BNA; (D) aminooxy ($4'-CH_2—O—N(R)-2'$) BNA; (E) oxyamino ($4'-CH_2—N(R)—O-2'$) BNA; (F) methyl(methyleneoxy) ($4'-CH(CH_3)—O-2'$) BNA (also referred to as constrained ethyl or cEt); (G) methylene-thio ($4'-CH_2—S-2'$) BNA; (H) methylene-amino (4'-CH2-N(R)-2') BNA; (I) methyl carbocyclic ($4'-CH_2—CH(CH_3)-2'$) BNA; (J) c-MOE ($4'-CH(CH_2—OMe)-O-2'$) BNA and (K) propylene carbocyclic ($4'-(CH_2)_3-2'$) BNA as depicted below.

(A)

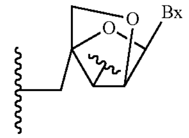

(B)

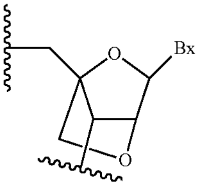

(C)

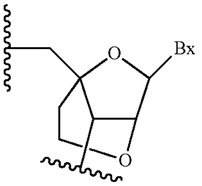

(D)

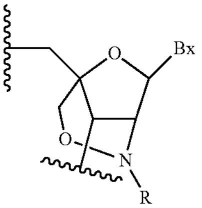

(E)

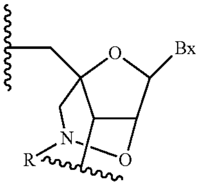

-continued (F)

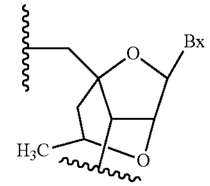

(G)

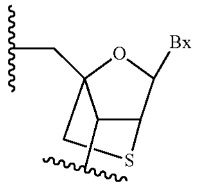

(H)

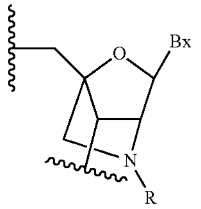

(I)

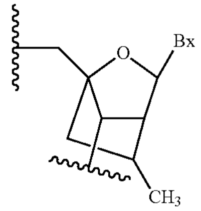

(J)

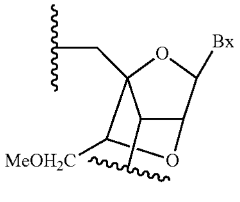

(K)

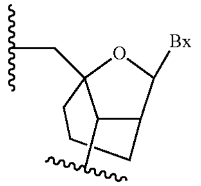

wherein Bx is a nucleobase moiety and R is, independently, H, a protecting group, or $C_1$-$C_{12}$ alkyl.

In certain embodiments, a 2'-modified nucleoside comprises a 2'-substituent group selected from F, $OCF_3$, O—$CH_3$ (also referred to as "2'-OMe"), $OCH_2CH_2OCH_3$ (also referred to as "2'-O-methoxyethyl" or "2'-MOE"), 2'-$O(CH_2)_2SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-$OCH_2CH_2OCH_3$, and 2'-F.

In certain embodiments, a modified oligonucleotide comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified oligonucleotide comprises one or more modified nucleobases. In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

In certain embodiments, a modified oligonucleotide is conjugated to one or more moieties which enhance the activity, cellular distribution or cellular uptake of the resulting antisense oligonucleotides. In certain such embodiments, the moiety is a cholesterol moiety. In certain embodiments, the moiety is a lipid moiety. Additional moieties for conjugation include carbohydrates, peptides, antibodies or antibody fragments, phospholipids, biotin, phenazine, folate, phenanthridine, anthraquinone, acridine, fluoresceins, rhodamines, coumarins, and dyes. In certain embodiments, the carbohydrate moiety is N-acetyl-D-galactosamine (GalNac). In certain embodiments, a conjugate group is attached directly to an oligonucleotide. In certain embodiments, a conjugate group is attached to a modified oligonucleotide by a linking moiety selected from amino, azido, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, azido, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Certain Pharmaceutical Compositions

Provided herein are pharmaceutical compositions comprising a compound or modified oligonucleotide provided herein, and a pharmaceutically acceptable diluent. In certain embodiments, the pharmaceutically acceptable diluent is an aqueous solution. In certain embodiments, the aqueous solution is a saline solution. As used herein, pharmaceutically acceptable diluents are understood to be sterile diluents. Suitable administration routes include, without limitation, intravenous and subcutaneous administration. In certain embodiments, administration is intravenous administration. In certain embodiments, administration is subcutaneous administration. In certain embodiments, administration is oral administration.

In certain embodiments, a pharmaceutical composition is administered in the form of a dosage unit. For example, in certain embodiments, a dosage unit is in the form of a tablet, capsule, or a bolus injection.

In certain embodiments, a pharmaceutical agent is a modified oligonucleotide which has been prepared in a suitable diluent, adjusted to pH 7.0-9.0 with acid or base during preparation, and then lyophilized under sterile conditions. The lyophilized modified oligonucleotide is subsequently reconstituted with a suitable diluent, e.g., aqueous solution, such as water or physiologically compatible buffers such as saline solution. Hanks's solution, or Ringer's solution. The reconstituted product is administered as a subcutaneous injection or as an intravenous infusion. The lyophilized drug product may be packaged in a 2 mL Type I, clear glass vial (ammonium sulfate-treated), stoppered with a bromobutyl rubber closure and sealed with an aluminum overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents.

In some embodiments, the pharmaceutical compositions provided herein may contain additional materials useful in physically formulating various dosage forms of the compositions provided herein, such as dyes, flavoring agents, preservatives, antioxidants, opacifiers, thickening agents and stabilizers; such additional materials also include, but are not limited to, excipients such as alcohol, polyethylene glycols, gelatin, lactose, amylase, magnesium stearate, talc, silicic acid, viscous paraffin, hydroxymethylcellulose and polyvinylpyrrolidone. In various embodiments, such materials, when added, should not unduly interfere with the biological activities of the components of the compositions provided herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

Lipid moieties have been used in nucleic acid therapies in a variety of methods. In one method, the nucleic acid is introduced into preformed liposomes or lipoplexes made of mixtures of cationic lipids and neutral lipids. In another method. DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, a pharmaceutical composition provided herein comprise a polyamine compound or a lipid moiety complexed with a nucleic acid. In certain embodiments, such preparations comprise one or more compounds each individually having a structure defined by formula (Z) or a pharmaceutically acceptable salt thereof,

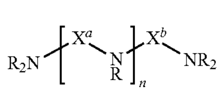

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (Z) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents provided herein to specific tissues or cell types. For example, in certain embodiments, pharmaceutical compositions include liposomes coated with a tissue-specific antibody.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Certain pharmaceutical compositions for injection are presented in unit dosage form, e.g., in ampoules or in multi-dose containers.

In certain embodiments, a pharmaceutical composition provided herein comprises a modified oligonucleotide in a therapeutically effective amount. In certain embodiments, the therapeutically effective amount is sufficient to prevent, alleviate or ameliorate symptoms of a disease or to prolong the survival of the subject being treated.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Additional administration routes include, but are not limited to, oral, rectal, transmucosal, intestinal, enteral, topical, suppository, through inhalation, intrathecal, intracardiac, intraventricular, intraperitoneal, intranasal, intraocular, intratumoral, intramuscular, and intramedullary administration. In certain embodiments, pharmaceutical intrathecals are administered to achieve local rather than systemic exposures. For example, pharmaceutical compositions may be injected directly in the area of desired effect (e.g., into the kidney).

Certain Kits

Kits are also provided. In some embodiments, the kits comprise one or more compounds comprising a modified oligonucleotide disclosed herein. In some embodiments, the kits may be used for administration of the compound to a subject.

In certain embodiments, the kit comprises a pharmaceutical composition ready for administration. In certain embodiments, the pharmaceutical composition is present within a vial. A plurality of vials, such as 10, can be present in, for example, dispensing packs. In some embodiments, the vial is manufactured so as to be accessible with a syringe. The kit can also contain instructions for using the compounds.

In some embodiments, the kit comprises a pharmaceutical composition present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds comprising a modified oligonucleotide disclosed herein.

In some embodiments, the kit comprised a modified oligonucleotide provided herein as a lyophilized drug product, and a pharmaceutically acceptable diluent. In preparation for administration to a subject, the lyophilized drug product is reconstituted in the pharmaceutically acceptable diluent.

In some embodiments, in addition to compounds comprising a modified oligonucleotide disclosed herein, the kit can further comprise one or more of the following: syringe, alcohol swab, cotton ball, and/or gauze pad.

Certain Experimental Models

In certain embodiments, methods are provided of using and/or testing modified oligonucleotides provided herein in an experimental model. Those having skill in the art are able to select and modify the protocols for such experimental models to evaluate a pharmaceutical agent provided herein.

Generally, modified oligonucleotides are first tested in cultured cells. Suitable cell types include those that are related to the cell type to which delivery of a modified oligonucleotide is desired in vivo. For example, suitable cell types for the study of the methods described herein include primary or cultured cells.

In certain embodiments, the extent to which a modified oligonucleotide interferes with the activity of one or more miR-17 family members is assessed in cultured cells. In certain embodiments, inhibition of microRNA activity may be assessed by measuring the level of one or more of a predicted or validated microRNA-regulated transcript. An inhibition of microRNA activity may result in the increase in the miR-17 family member-regulated transcript, and/or the protein encoded by miR-17 family member-regulated transcript (i.e., the miR-17 family member-regulated transcript is de-repressed). Further, in certain embodiments, certain phenotypic outcomes may be measured.

Several animal models are available to the skilled artisan for the study of one or more miR-17 family members in models of human disease. Models of polycystic kidney disease include, but are not limited to, models with mutations and/or deletions in Pkd1 and/or Pkd2; and models comprising mutations in other genes. Nonlimiting exemplary models of PKD comprising mutations and/or deletions in Pkd1 and/or Pkd2 include hypomorphic models, such as models comprising missense mutations in Pkd1 and models with reduced or unstable expression of Pkd2; inducible conditional knockout models; and conditional knockout models. Nonlimiting exemplary PKD models comprising mutations in genes other than Pkd1 and Pkd2 include models with mutations in Pkhd1, Nek8, Kif3a, and/or Nphp3. PKD models are reviewed, e.g., in Shibazaki et al., *Human Mol. Genet.,* 2008; 17(11): 1505-1516; Happe and Peters, *Nat Rev Nephrol.,* 2014; 10(10): 587-601; and Patel et al., *PNAS,* 2013; 110(26): 10765-10770.

Certain Quantitation Assays

In certain embodiments, microRNA levels are quantitated in cells or tissues in vitro or in vivo. In certain embodiments, changes in microRNA levels are measured by microarray analysis. In certain embodiments, changes in microRNA levels are measured by one of several commercially available PCR assays, such as the TaqMan® MicroRNA Assay (Applied Biosystems).

Modulation of microRNA activity with an anti-miR or microRNA mimic may be assessed by microarray profiling of mRNAs. The sequences of the mRNAs that are modulated (either increased or decreased) by the anti-miR or microRNA mimic are searched for microRNA seed sequences, to compare modulation of mRNAs that are targets of the microRNA to modulation of mRNAs that are not targets of the microRNA. In this manner, the interaction of the anti-miR with its target microRNA, or a microRNA mimic with its targets, can be evaluated. In the case of an anti-miR, mRNAs whose expression levels are increased are screened for the mRNA sequences that comprise a seed match to the microRNA to which the anti-miR is complementary.

Modulation of microRNA activity with an anti-miR compound may be assessed by measuring the level of a messenger RNA target of the microRNA, either by measuring the level of the messenger RNA itself, or the protein transcribed therefrom. Antisense inhibition of a microRNA generally results in the increase in the level of messenger RNA and/or protein of the messenger RNA target of the microRNA, i.e., anti-miR treatment results in de-repression of one or more target messenger RNAs.

EXAMPLES

The following examples are presented in order to more fully illustrate some embodiments of the invention. They should in no way be construed, however, as limiting the broad scope of the invention.

Those of ordinary skill in the art will readily adopt the underlying principles of this discovery to design various compounds without departing from the spirit of the current invention.

Example 1: The Role of miR-17 in PKD miR-17 family members of the miR-17~92 cluster of microRNAs are upregulated in mouse models of PKD. Genetic deletion of the miR-17~92 cluster in a mouse model of PKD reduces kidney cyst growth, improves renal function, and prolongs survival (Patel et al., *PNAS,* 2013; 110 (26): 10765-10770). The miR-17~92 cluster contains 6 different microRNAs, each with a distinct sequence: miR-17, miR-18a, miR-19a, miR-19-b-1 and miR-92a-1.

The miR-17~92 cluster includes two microRNAs, miR-17 and miR-20a, that are members of the miR-17 family of microRNAs. Each member of this family shares seed sequence identity, and varying degrees of sequence identity outside the seed region. The other members of the miR-17 family are miR-20b, miR-93, miR-106a, and miR-106b, miR-20b and miR-106a reside within the miR-106a~363 cluster on the human X chromosome, and miR-93 and miR-106b reside within the miR-106b~25 cluster on human chromosome 7. The sequences of the miR-17 family members are shown in Table 1.

TABLE 1 miR-17 family of microRNAs

| microRNA | SEQUENCE (5' TO 3') seed region in bold | SEQ ID NO: |
|---|---|---|
| miR-17 | C**AAAGUG**CUUACAGUGCAGGUAG | 1 |
| miR-20a | U**AAAGUG**CUUAUAGUGCAGGUAG | 2 |
| miR-20b | C**AAAGUG**CUCAUAGUGCAGGUAG | 3 |
| miR-93 | C**AAAGUG**CUGUUCGUGCAGGUAG | 4 |
| miR-106a | A**AAAGUG**CUUACAGUGCAGGUAG | 5 |
| miR-106b | U**AAAGUG**CUGACAGUGCAGAU | 6 |

The anti-miR-17 compound RGLS4326 was discovered by screening a chemically diverse and rationally designed library of anti-miR-17 oligonucleotides for optimal pharmaceutical properties. RGLS4326 preferentially distributes to kidney and collecting duct-derived cysts, displaces miR-17 from translationally active polysomes, and de-represses multiple miR-17 mRNA targets including Pkd1 and Pkd2. Importantly, RGLS4326 attenuates cyst growth in human in vitro ADPKD models and multiple PKD mouse models after subcutaneous administration. A phase 1 single ascending dose (SAD) clinical trial of RGLS4326 in healthy volunteers was initiated in December 2017, followed by a phase 1 multiple ascending dose (MAD) clinical trial in healthy volunteers that was initiated in May 2018. A phase 1b clinical trial of RGLS4326 for the treatment of patients with autosomal dominant polycystic kidney disease (ADPKD) was initiated in October 2020.

Subsequent to the initiation of the phase 1 MAD clinical trial, nonclinical toxicology studies revealed central nervous system (CNS)-related findings, including abnormal gait, reduced motor activity, and/or prostration, at high doses of RGLS4326. To identify potential candidates for off-target pharmacology, a panel of 174 targets including G-protein coupled receptors, transporters, ion channels, nuclear receptors, and cytokine receptors was evaluated in vitro for possible interactions with RGLS4326. RGLS4326 was found to be an antagonist of the AMPA glutamate receptor, with a 50% inhibitory concentration (IC50) of 4.6 uM (14.2 μg/mL) based on ligand binding and a functional IC50 of 300-600 nM (0.9-1.8 μg/mL) based on patch clamp activity. AMPA receptors are ion channels on excitatory synapses in the CNS that mediate fast excitatory neurotransmission and, therefore, are key components of all neuronal networks. Such an interaction with the AMPA receptor could explain the CNS-mediated findings observed at high doses of RGLS4326 in nonclinical toxicology models.

Example 2: Screen for Anti-miR-17 Compounds With Reduced AMPA Receptor Binding RGLS4326 has the following sequence and chemical modification pattern: $A_SG_SC_MA_FC_FU_FU_MU_SG_S$ where nucleosides followed by subscript "M" are 2'-O-methyl nucleosides, nucleosides followed by subscript "F" are 2'-fluoro nucleosides, nucleosides followed by subscript "S" are S-cEt nucleosides, each cytosine is a non-methylated cytosine, and all linkages are phosphorothioate linkages. Chemical modification and length variants of RGLS4326 were designed and screened to identify a compound that retains the potency and pharmacokinetic profile of RGLS4326 and exhibits reduced binding to the AMPA receptor (AMPA-R).

A library of compounds was designed with varying chemical modifications, nucleobase sequence, and length, relative to RGLS4326.

TABLE 2 anti-miR-17 Library

| Compound # | Chemical Notation | Nucleobase Sequence | SEQ ID NO | Length |
|---|---|---|---|---|
| RG-NG-1001 | $A_SG_SC_SA_SC_SU_SU_SU_SG_S$ | AGCACUUUG | | 9 |
| RG-NG-1002 | $A_SG_SC_SA_SC_SU_SU_SU_S$ | AGCACUUU- | | 8 |
| RG-NG-1003 | $A_SG_SC_MA_SC_MU_SU_MU_SG_S$ | AGCACUUUG | | 9 |
| RG-NG-1004 | $U_SA_SA_SG_SC_SA_SC_SU_SU_SU_SG_S$ | UAAGCACUUUG | 12 | 11 |
| RG-NG-1005 | $U_SA_SA_MG\underline{\underline{C}}_SA_SC_SU_MU_MU_SG_S$ | UAAGCACUUUG | 13 | 11 |
| RG-NG-1006 | $A_LG_L\underline{\underline{C}}_LA_L\underline{\underline{C}}_LT_LT_LT_LG_L$ | AGCACTTTG | | 9 |
| RG-NG-1007 | $A_SG_SC_FA_FC_FU_FU_FU_SG_S$ | AGCACUUUG | | 9 |
| RG-NG-1008 | $A_SG_EC_MA_FC_FU_FU_MT_EG_S$ | AGCACUUTG | | 9 |
| RG-NG-1009 | $A_EG_EC_MA_FC_FU_FU_MT_EG_E$ | AGCACUUTG | | 9 |
| RG-NG-1010 | $A_EG_EC_MA_FC_FU_FU_MU_SG_S$ | AGCACUUUG | | 9 |
| RG-NG-1011 | $A_LG_LC_MA_FC_FU_FU_MU_SG_S$ | AGCACUUUG | | 9 |
| RG-NG-1012 | $A_SG_LC_MA_FC_FU_FU_MT_LG_S$ | AGCACUUTG | | 9 |
| RG-NG-1013 | $A_SA_SG_SC_MA_FC_FU_FU_MU_S$ | AAGCACUUU- | | 9 |
| RG-NG-1014 | $A_SG_SC_MA_FC_FU_FU_MU_S$ | AGCACUUU- | | 8 |
| RG-NG-1015 | $A_SG_SC_MA_FC_FU_FU_MU_SA_S$ | AGCACUUUA | | 9 |
| RG-NG-1016 | $A_SG_SC_MA_FC_FU_FU_MU_SC_S$ | AGCACUUUC | | 9 |
| RG-NG-1017 | $A_SG_SC_MA_FC_FU_FU_MU_SU_S$ | AGCACUUUU | | 9 |
| RG-NG-1018 | $A_E\underline{\underline{C}}_ET_EG_ST_EAA_SG_SC_MA_FC_FU_FU_MU_SC_S$ | ACTGTAAGCACUUUC | 14 | 15 |
| RG-NG-1019 | $A_SC_STG_SU_SAA_SG_SC_MA_FC_FU_FU_MU_SC_S$ | ACTGUAAGCACUUUC | 15 | 15 |
| RG-NG-1020 | $T_EG_ST_EAA_SG_SC_MA_FC_FU_FU_MU_SC_S$ | TGTAAGCACUUUC | 16 | 13 |
| RG-NG-1021 | $T_EAA_SG_SC_MA_FC_FU_FU_MU_SC_S$ | TAAGCACUUUC | 17 | 11 |
| RG-NG-1022 | $T_EA_FA_SG_SC_MA_FC_FU_FU_MU_SC_S$ | TAAGCACUUUC | 18 | 11 |
| RG-NG-1023 | $A_FG_SC_MA_FC_FU_FU_MU_SG_E$ | AGCACUUUG | | 9 |
| RG-NG-1024 | $A_SG_SC_MA_FC_FU_FU_MT_EG_E$ | AGCACUUTG | | 9 |
| RG-NG-1025 | $A_SG_SC_MA_FC_FU_FU_MU_SG_E$ | AGCACUUUG | | 9 |
| RG-NG-1026 | $A_SG_SC_MA_LC_FU_FU_MU_SC_S$ | AGCACUUUC | | 9 |
| RG-NG-1027 | $A_SG_SC_SA_FC_FU_FU_MU_SC_S$ | AGCACUUUC | | 9 |

TABLE 2-continued

| anti-miR-17 Library | | | | |
|---|---|---|---|---|
| Compound # | Chemical Notation | Nucleobase Sequence | SEQ ID NO | Length |
| RG-NG-1028 | $A_SG_SC_SA_LC_FU_FU_MU_SC_S$ | AGCACUUUC | | 9 |
| RG-NG-1029 | $A_MG_L\underline{\underline{C}}_LA_L\underline{\underline{C}}_LU_MT_LU\underline{\underline{C}}_M$ | AGCACUTUC | | 9 |
| RG-NG-1030 | $A_MA_MG_L\underline{\underline{C}}_LA_L\underline{\underline{C}}_LU_MT_LU\underline{\underline{C}}_M$ | AAGCACUTUC | 19 | 10 |
| RG-NG-1031 | $A_MA_MG_L\underline{\underline{C}}_LA_L\underline{\underline{C}}_LU_MT_LU_M$ | AAGCACUTU- | | 9 |

Nucleosides followed by subscript "M" are 2'-O-methyl nucleosides;
nucleosides followed by subscript "F" are 2'-fluoro nucleosides;
nucleosides followed by subscript "S" are S-cEt nucleosides;
nucleosides followed by subscript "E" are 2'-O-methoxyethyl (2'-MOE) nucleosides; and
nucleosides followed by subscript "L" are LNA nucleosides.

The activity of anti-miR-17 compounds was evaluated in a radioligand binding assay which measured the binding of the [$^3$H] AMPA ligand to the AMPA-R present on rat brain synaptic membranes, in the presence of increasing concentrations of anti-miR-17 compound, anti-miR-17 compounds with affinity for the AMPA-R will bind to and compete with the binding of the [$^3$H] AMPA ligand.

The assay was performed according to previously published methods (Honore et al., *J Neurochem.,* 1982, 38(1): 173-178; Olsen et al., *Brain Res.,* 1987, 402(2):243-254). 5.0 nM of the ligand [$^3$H] AMPA, 1.0 mM of the non-specific ligand L-Glutamic acid, and anti-miR compound at uM concentrations were incubated with synaptic membranes prepared from Wistar rat cerebral cortex for 90 minutes. The compounds shown in Table 2 were tested in three experiments. Anti-miRs targeted to microRNAs other than miR-17 were used as control compounds (RG5124 targeted to miR-33a; RG5365 targeted to let-7a; RG8093 targeted to miR-214). RGLS4326 and RG-NG-1001 were also tested in each experiment, as it was demonstrated to bind to and inhibit the activity of the AMPA-R. The amount of the [$^3$H] AMPA ligand was quantitated by radioligand binding, and is shown in Tables 3, 4, and 5. As illustrated by the data, the compounds vary in their ability to inhibit binding of the radiolabeled ligand to the AMPA-R.

TABLE 3

| Inhibition of Ligand Binding to AMPA-R Experiment #1 | | | | | | | |
|---|---|---|---|---|---|---|---|
| | SEQ | Nucleobase Sequence & Chemistry | % Inhibition @ uM | | | | |
| Compound # | ID NO | (5' to 3') | 100 | 10 | 1 | 0.1 | $IC_{50}$ (uM) |
| RG-NG-1001 | | $A_SG_SC_SA_SC_SU_SU_SU_SG_S$ | 91.3 | 89.1 | 76.2 | 41.1 | 0.17 |
| RGLS4326 | | $A_SG_SC_MA_FC_FU_FU_MU_SG_S$ | 104.1 | 93 | 55.5 | 17.6 | 0.70 |
| RG-NG-1002 | | $A_SG_SC_SA_SCs_SU_SU_SU_S$ | 24.0 | −16.9 | −2.0 | 0 | >100 |
| RG-NG-1003 | | $A_SG_SC_MA_SC_MU_SU_MU_SG_S$ | 77.8 | 56.9 | 13.9 | 5.7 | 9.26 |
| RG-NG-1004 | 20 | $U_SA_SA_SG_SC_SA_SC_SU_SU_SU_SG_S$ | 76.1 | 44.2 | 4.7 | −4.7 | 17.28 |
| RG-NG-1005 | 21 | $U_SA_SA_MG\underline{\underline{C}}_SA_SC_SU_MU_MU_SG_S$ | 28.3 | 0.8 | −1.3 | 10.8 | >100 |
| RG-NG-1006 | | $A_LG_L\underline{\underline{C}}_LA_L\underline{\underline{C}}_LT_LT_LT_LG_L$ | 93.9 | 68.9 | 35.3 | 6.7 | 2.77 |
| RG5124 | | $A_SC_SA_MA_FU_FG_FC_MA_SC_S$ (anti-miR-33a) | −5.1 | −3.7 | 12.9 | 0.4 | >100 |
| RG5365 | | anti-let7a | −4 | 6.5 | −6.3 | 2.4 | >100 |
| RG8093 | | anti-miR-214 | −9.8 | −2 | −11.5 | −6.9 | >100 |

TABLE 4

| Inhibition of Ligand Binding to AMPA-R Experiment #2 | | | | | | | |
|---|---|---|---|---|---|---|---|
| | SEQ | | % Inhibition @ uM | | | | |
| Compound # | ID NO | Chemical Notation | 100 | 10 | 1 | 0.1 | $IC_{50}$ (uM) |
| RG-NG-1001 | | $A_SG_SC_SA_SC_SU_SU_SU_SG_S$ | 93.5 | 90.1 | 68.3 | 42.2 | 0.19 |
| RGLS4326 | | $A_SG_SC_MA_FC_FU_FU_MU_SG_S$ | 96.8 | 93.6 | 73.1 | 31.5 | 0.27 |

TABLE 4-continued

Inhibition of Ligand Binding to AMPA-R Experiment #2

| Compound # | SEQ ID NO | Chemical Notation | % Inhibition @ uM 100 | 10 | 1 | 0.1 | $IC_{50}$ (uM) |
|---|---|---|---|---|---|---|---|
| RG-NG-1002 | | $A_SG_SC_SA_SC_SU_SU_SU_S$ | 24.6 | -2.1 | 4.6 | -5.5 | >100 |
| RG-NG-1007 | | $A_SG_SC_FA_FC_FU_FU_FU_SG_S$ | 94.3 | 83.2 | 39.7 | 3.1 | 1.69 |
| RG-NG-1008 | | $A_SG_EC_MA_FC_FU_FU_MT_EG_S$ | 59.6 | 22.1 | 13.6 | -22.4 | 56.58 |
| RG-NG-1009 | | $A_EG_EC_MA_FC_FU_FU_MT_EG_E$ | 32.6 | 13 | 2.7 | -11.8 | >100 |
| RG-NG-1010 | | $A_EG_EC_MA_FC_FU_FU_MU_SG_S$ | 86.4 | 70.1 | 31.3 | 0.7 | 3.44 |
| RG-NG-1011 | | $A_LG_LC_MA_FC_FU_FU_MU_SG_S$ | 94 | 78.5 | 30.6 | -2.2 | 2.56 |
| RG-NG-1012 | | $A_SG_LC_MA_FC_FU_FU_MT_LG_S$ | 88.3 | 69 | 38.5 | 9.9 | 2.56 |
| RG-NG-1013 | | $A_SA_SG_SC_MA_FC_FU_FU_MU_S$ | 37.2 | 3.7 | -5.6 | -3.8 | >100 |
| RG-NG-1014 | | $A_SG_SC_MA_FC_FU_FU_MU_S$ | 20.4 | 8.6 | -5.5 | 14.9 | >100 |
| RG-NG-1015 | | $A_SG_SC_MA_FC_FU_FU_MU_SA_S$ | 19.9 | 6.5 | 11 | 2.3 | >100 |
| RG-NG-1016 | | $A_SG_SC_MA_FC_FU_FU_MU_SC_S$ | 5.9 | 12.3 | 10.4 | 4.7 | >100 |
| RG-NG-1017 | | $A_SG_SC_MA_FC_FU_FU_MU_SU_S$ | 8.1 | 4.3 | -1.3 | 0.2 | >100 |
| RG-NG-1026 | | $A_SG_SC_MA_LC_FU_FU_MU_SC_S$ | 2.3 | -3.5 | -1.1 | -3.3 | >100 |
| RG-NG-1027 | | $A_SG_SC_SA_FC_FU_FU_MU_SC_S$ | 3 | -2.2 | 2.3 | -2.2 | >100 |
| RG-NG-1028 | | $A_SG_SC_SA_LC_FU_FU_MU_SC_S$ | 2.7 | 2 | 2.1 | 15.7 | >100 |
| RG-NG-1029 | | $A_MG_L\underline{C}_LA_L\underline{C}_LGU_MT_LU\underline{C}_M$ | 38.4 | 7 | 15.9 | 0.9 | >100 |
| RG-NG-1030 | 19 | $A_MA_MG_L\underline{C}_LA_L\underline{C}_LU_MT_LU\underline{C}_M$ | 1.9 | 15 | 6.5 | 2.9 | >100 |
| RG-NG-1031 | | $A_MA_MG_L\underline{C}_LA_L\underline{C}_LU_MT_LU_M$ | 16.7 | 2.7 | 1 | -4.3 | >100 |
| RG5124 | | $A_SC_SA_MA_FU_FG_FC_MA_SC_S$ (anti-miR-33a) | 7.2 | -4.2 | 1.6 | -1.2 | >100 |

TABLE 5

Inhibition of Ligand Binding to AMPA-R Experiment #3

| Compound # | SEQ ID NO | Chemical Notation | % Inhibition @ uM 100 | 10 | 1 | 0.1 | $IC_{50}$ (uM) |
|---|---|---|---|---|---|---|---|
| RG-NG-1001 | | $A_SG_SC_SA_SC_SU_SU_SU_SG_S$ | 96.6 | 94.6 | 84.8 | 59.4 | 0.10 |
| RGLS4326 | | $A_SG_SC_MA_FC_FU_FU_MU_SG_S$ | 97.2 | 89 | 55.8 | 14.6 | 0.78 |
| RG-NG-1018 | 22 | $A_E\underline{C}_ET_EG_ST_EAA_SG_SC_MA_FC_FU_FU_MU_SC_S$ | 12.3 | 1 | 8.1 | 3 | >100 |
| RG-NG-1019 | 23 | $A_SC_STG_SU_SAA_SG_SC_MA_FC_FU_FU_MU_SC_S$ | 21 | 15.6 | 17.2 | 12.9 | >100 |
| RG-NG-1020 | 24 | $T_EG_ST_EAA_SG_SC_MA_FC_FU_FUMU_SC_S$ | -7.9 | -23.3 | 6.6 | 17 | >100 |
| RG-NG-1021 | 25 | $T_EAA_SG_SC_MA_FC_FU_FU_MU_SC_S$ | -1.5 | -11.5 | -10.9 | -2 | >100 |
| RG-NG-1022 | 26 | $T_EA_EA_SG_SC_MA_FC_FU_FU_MU_SC_S$ | -10.9 | -7 | -5.4 | -23.5 | >100 |
| RG-NG-1023 | | $A_EG_SC_MA_FC_FU_FU_MU_SG_E$ | 95.3 | 75.2 | 25.6 | 3.1 | 3.12 |
| RG-NG-1024 | | $A_SG_SC_MA_FC_FU_FU_MT_EG_E$ | 35.2 | 6.5 | -4.7 | -17 | >100 |
| RG-NG-1025 | | $A_SG_SC_MA_FC_FU_FU_MU_SG_E$ | 96.4 | 84.1 | 36.5 | -3.8 | 1.85 |
| RG5124 | | $A_SC_SA_MA_FU_FG_FC_MA_SC_S$ (anti-miR-33a) | 23 | 16.1 | 9.3 | 5.1 | >100 |

To evaluate functional antagonism of anti-miR-17 oligonucleotides towards the AMPA-R, certain oligonucleotides were tested using the manual whole-cell patch clamp technique, which records membrane currents as a measure of AMPA-R activity.

Manual whole-cell patch clamp studies were performed by Metrion Biosciences (Cambridge, UK). Whole-cell voltage clamp experiments were performed at room temperature (18-21° C.) using an EPC10 patch clamp amplifier using Patchmaster software (HEKA Elektronik). Glass patch pipettes were fabricated from borosilicate glass capillaries (Harvard Apparatus) to resistances between 1.4 and 2.5 MΩ. Membrane currents were recorded using the whole-cell patch clamp technique. ChanTest® GluA1/GluA4 EZCells were clamped at a holding potential of −80 mV and membrane currents elicited by 10 μM(S)-AMPA delivered using a VC38 perfusion system (ALA Scientific Instruments). The minimal current amplitude values were measured with each application of 10 μM(S)-AMPA. The fractional change of current amplitude produced by each concentration of compound was calculated relative to the control current (pre-compound) and expressed as percentage change (% inhibition) for each cell. The compounds tested are shown in Table 6. RGLS4326 was tested in a separate study from all other compounds in Table 6.

As shown in Table 6, relative to RGLS4326, compounds RG-NG-1015, RG-NG-1016, and RG-NG-1017 exhibited reduced functional antagonism towards AMPA-R based on the manual whole-cell patch clamp studies in human Chan Test® GluA1/GluA4 EZ-Cells.

TABLE 6

Functional Antagonism of AMPA-R in Whole-Cell Patch Clamp Studies

| Compound ID | Sequence & Chemistry (5'-3') | Target | % Inhibition on membrane currents evoked with 10 uM (s)-AMPA (Mean ± SD) 0.3 uM | 3 uM |
|---|---|---|---|---|
| RG-NG-1001 | $A_SG_SC_SA_SC_SU_SU_SU_SG_S$ | miR-17 | 80.5 ± 6.3 | 88.8 ± 4.5 |
| RGLS4326 | $A_SG_SC_MA_FC_FU_FU_MU_SG_S$ | miR-17 | 46.9 ± 9.8 | 87.4 ± 7.9 |
| RG-NG-1015 | $A_SG_SC_MA_FC_FU_FU_MU_SA_S$ | miR-17 | 16.0 ± 5.0 | 39.5 ± 5.4 |
| RG-NG-1016 | $A_SG_SC_MA_FC_FU_FU_MU_SC_S$ | miR-17 | 16.0 ± 6.2 | 27.1 ± 9.8 |
| RG-NG-1017 | $A_SG_SC_MA_FC_FU_FU_MU_SU_S$ | miR-17 | 20.0 ± 6.3 | 28.2 ± 5.5 |
| RG5124 | $A_SC_SA_MA_FU_FG_EC_MA_SC_S$ | miR-33a | 14.1 ± 7.2 | 42.1 ± 9.4 |

Example 3: Relationship Between Nucleobase Properties and AMPA-R Binding

As illustrated by the AMPA-R binding and whole-cell patch clamp studies, the presence of guanosine at the 3'-terminus of an anti-miR-17 oligonucleotide, at the position complementary to the first nucleotide of miR-17, influences the functional antagonism of the AMPA-R. Like guanosine, adenosine is a purine, however adenosine did not inhibit the AMPA-R. Guanosine and adenosine are similar with regard to several properties except for hydrogen bonding, thus the differences in hydrogen bonding at positions 1, 2, and 6 of the purine base were evaluated. The purine nucleobases tested are shown in FIG. 1 and Table 7. In the "Purine Position" column of Table 7, "A" indicates a position of the purine that is hydrogen acceptor and "D" indicates a position of the purine that is a hydrogen donor. In the "Purine Position" column of Table 7, "N" indicates a neutral position that is neither a hydrogen acceptor or donor. Also tested were varying 2'-sugar moieties on the purine nucleobase, to evaluate the influence of 2'-sugar moiety chemistry on the ability of the purine nucleobase to inhibit the AMPA-R.

TABLE 7

| Anti-miR-17 Compounds With Varying Nucleobase and Sugar Moiety Chemistry | | | | | | | |
|---|---|---|---|---|---|---|---|
| | Nucleobase at 3-terminus (single | 2'-Sugar Moiety at | SEQ | Sequence & Chemistry | Purine Position | | |
| Compound ID | letter notation) | 3'-terminus | ID NO | (5'-3') | # 6 | # 1 | # 2 |
| RG-NG-1001 | guanosine (G) | S-cEt | | $A_SG_SC_SA_SC_SU_SU_SU_SG_S$ | A | D | D |
| RG-NG-1040 | guanosine (G) | S-cEt | 27 | $\underline{\underline{C}}_ET_EG_S\underline{\underline{C}}_EA_E\underline{\underline{C}}_ET_EG_ST_EA_D$ $A_SG_SC_MA_FC_FU_FU_MU_SG_S$ | A | D | D |
| RG-NG-1032 | guanosine (G) | S-cEt | 28 | $G_S\underline{\underline{C}}_EA_E\underline{\underline{C}}_ET_EG_ST_EA_D$ $A_SG_SC_MA_FC_FU_FU_MU_SG_S$ | A | D | D |
| RG4326 | guanosine (G) | S-cEt | | $A_SG_SC_MA_FC_FU_FU_MU_SG_S$ | A | D | D |
| RG-NG-1033 | guanosine (G) | DNA | | $A_SG_SC_MA_FC_FU_FU_MU_SG_D$ | A | D | D |
| RG-NG-1034 | guanosine (G) | 2'-O-methyl | | $A_SG_SC_MA_FC_FU_FU_MU_SG_M$ | A | D | D |
| RG-NG-1035 | inosine (I) | S-cEt | | $A_SG_SC_MA_FC_FU_FU_MU_SI_M$ | A | D | N |
| RG-NG-1036 | 2-aminopurine (N) | 2'-O-methyl | | $A_SG_SC_MA_FC_FU_FU_MU_SN_M$ | N | A | D |
| RG-NG-1037 | 2,6-diaminopurine (D) | 2'-O-methyl | | $A_SG_SC_MA_FC_FU_FU_MU_SD_M$ | D | A | D |
| RG-NG-1039 | isoguanine (F) | DNA | | $A_SG_SC_MA_FC_FU_FU_MU_SE_D$ | D | D | A |
| RG-NG-1038 | adenosine (A) | 2'-O-methyl | | $A_SG_SC_MA_FC_FU_FU_MU_SA_M$ | D | A | N |
| RG-NG-1015 | adenosine (A) | S-cEt | | $A_SG_SC_MA_FC_FU_FU_MU_SA_S$ | D | A | N |
| RG5124 | cytidine (C) | S-cEt | | $A_SC_SA_MA_FU_FG_EC_MA_SC_S$ | | | |

The compounds were tested in the radioligand binding assay described herein, to determine the ability of the anti-miR-17 compounds to and compete with the binding of the [3H] AMPA ligand. As shown in Table 8, a correlation was observed between inhibition of ligand binding to the +AMPA-R and the presence of a hydrogen bond acceptor at purine position #6 of the nucleobase at the 3'-terminus of the oligonucleotide. For example, compounds having guanosine or inosine at the 3'-terminus resulted in inhibition of ligand binding to the AMPA-R. Compounds with a 3'-terminal nucleobase having a hydrogen bond acceptor at purine position #6, for example RG-NG-1037 and RG-NG-1039, were less likely to inhibit ligand binding to the AMPA-R.

TABLE 8

| Inhibition of Ligand Binding to AMPA-R | | | | | | | | | | |
|---|---|---|---|---|---|---|---|---|---|---|
| | Nucleobase | 2'-Sugar Moiety | Purine | | | % Inhibition @ Concentration | | | | |
| | at | at | Position | | | 100 | 10 | 1 | 0.1 | IC50 |
| ID | 3-terminus | 3'-terminus | #6 | #1 | #2 | uM | uM | uM | uM | (uM) |
| RG-NG-1001 | guanosine | S-cEt | A | D | D | 102.9 | 99.3 | 81.3 | 41.9 | 0.15 |
| RG-NG-1040 | guanosine | S-cEt | A | D | D | 64.1 | 38.9 | 14.4 | 10.4 | 28.61 |
| RG-NG-1032 | guanosine | S-cEt | A | D | D | 92 | 78.3 | 43.8 | 24.3 | 1.17 |
| RG-NG-4326 | guanosine | S-cEt | A | D | D | 99.7 | 83.5 | 40.8 | −0.1 | 1.61 |
| RG-NG-1033 | guanosine | DNA | A | D | D | 97.3 | 96.5 | 80.9 | 44.9 | 0.13 |
| RG-NG-1034 | guanosine | 2'-O-methyl | A | D | D | 99.7 | 85.2 | 44.8 | 14.3 | 1.20 |
| RG-NG-1035 | inosine | S-cEt | A | D | N | 98.5 | 91.3 | 46.3 | 27.2 | 0.76 |
| RG-NG-1036 | 2-aminopurine | 2'-O-methyl | N | A | D | 78.1 | 36.2 | 11.3 | 19.2 | 18.61 |
| RG-NG-1037 | 2,6-diaminopurine | 2'-O-methyl | D | A | D | 10.7 | 2.4 | 9.2 | 11.1 | 100.00 |
| RG-NG-1039 | isoguanine | DNA | D | D | A | 30.2 | 35.8 | 27 | 27.3 | 100.00 |
| RG-NG-1038 | adenosine | 2'-O-methyl | D | A | N | 81.3 | 47.4 | 25.4 | 17.9 | 8.23 |
| RG-NG-1015 | adenosine | S-cEt | D | A | N | 5.6 | −7 | −10.3 | −0.8 | 100.00 |
| RG5124 | cytidine | S-cEt | | | | 10.1 | 4.4 | −0.6 | −8.6 | 100.00 |

Example 4: Anti-miR-17 Compounds With Reduced Binding and Inhibition of AMPA-R Showed No CNS Toxicity in High Dose Studies RG-NG-1015, RG-NG-1016, and RG-NG-1017 were tested in high-dose mouse toxicity studies. Each compound was tested in a single dose at 2000 mg/kg, and at escalating doses (100, 450, and 2000 mg/kg). As shown in Table 9, while escalating doses of RG-NG-1001 and RGLS4326 resulted in ataxia, lethargy, and in the case of RGLS4326, unconsciousness at the highest dose, no CNS-toxicity were observed for RG-NG-1015, RG-NG-1016, or RG-NG-1017.

TABLE 9

| Anti-miR-17 Compounds and CNS-related findings | | | | |
|---|---|---|---|---|
| | Mice/ group | SC Dose (mg/kg/dose) | Schedule | CNS-related findings noted: |
| RG-NG-1001 | 8 | 100, 450, 2000 | QDx3 | Mild Body Scratching and Ataxia observed at 100 and increase at 450 mg/kg; Lethargy observed at 2000 mg/kg |
| RGLS4326 | 10 | 100, 450, 2000 | QDx4 | Ataxia and/or lethargy observed at 450 mg/kg; Ataxia, lethargy and/or unconsciousness observed at 2000 mg/kg |
| RG-NG-1015 | 7 | 2000 | Single | No |
| | 6 | 100, 450, 2000 | QDx4 | No |
| RG-NG-1016 | 10 | 2000 | Single | No |
| | 6 | 100, 450, 2000 | QDx4 | No |
| RG-NG-1017 | 10 | 2000 | Single | No |
| | 6 | 100, 450, 2000 | QDx4 | No |
| RG5124 | 7-10 | 100, 450, 2000 | QDx3 | Mild ataxia observed at 2000 mg/kg |

Example 5: Maximum Tolerated Dose (MTD) Study and Comparative Dose Assessment of Different Compounds Data from below studies further support that AMPA-R antagonism is responsible for CNS toxicity and mortality observed in previous toxicity studies of RGLS4326.

Study 1: Maximum Tolerated Dose (MTD) Study and Comparative Dose Assessment of RG-NG-1017, RGLS4326 and RG-NG-1001

Compounds (RG-NG-1017, RGLS4326, RG-NG-1001) were evaluated in a pilot maximum tolerated dose (MTD) study (discussed below). RG-NG-1017, RGLS4326 and RG-NG-1001 were initially evaluated at 4 dose-levels each. RG-NG-1017 was included for evaluation as a non-AMPA-R binding compound, as compared to RGLS4326 and RG-NG-1001, which bind AMPA-R. C57Bl/6J male mice (Jackson Laboratories), age 6-7 weeks, were used in this study. Mice were assigned randomly to treatment groups, and the study was blinded. Animals were allowed to acclimate for no less than 5 days and housed on a 12 hr light/dark cycle (lights on 7:00 AM). No more than 4 mice were house in each cage in a ventilated cage rack system. The diet consisted of standard rodent chow and water ad libitum.

MTD Pilot Study

The following parameters were used for this study:

1. Route(s) of administration: intracerebroventricular (ICV) dosing of RG-NG-1017, RG-NG-1001, RGLS4326
2. Dose Volume(s): 4 μL
3. Formulation(s): vehicle, $Ca^{2+}$ and $Mg^{2+}$ free dPBS
4. Dose Frequency: Once
5. Study duration: 8 Days
6. Number of Groups: 3
7. Number of animals per group: (2-4 each group)
8. Total number of animals: 54

For the ICV administration, mice were anesthetized and positioned for injections. The skin over the skull was incised, and a small hole was made in the skull above the target using a microdrill. The stereotactic coordinates were anteroposterior (AP), −0.4 mm; mediolateral (ML), +/−1.0-1.5 mm; dorsoventral (DV), −3.0 mm from the bregma for injection into both the right and left lateral cerebral ventricles (Hironaka et al, 2015). Animals were injected unilaterally with 4 μl into the right lateral cerebral ventricle. Compounds were injected over 1-2 min, and the needle was left in place for 0.5-1 min prior to withdrawal. The incision was closed with sutures, wound clips, or VetBond.

Following ICV treatment (Day 0), animals were monitored for 7 days in which daily health checks, body weight, and mortality was recorded. On Day 7, brain and kidney were collected and fixed (10% formalin) and stored pending histology.

Figure 3:
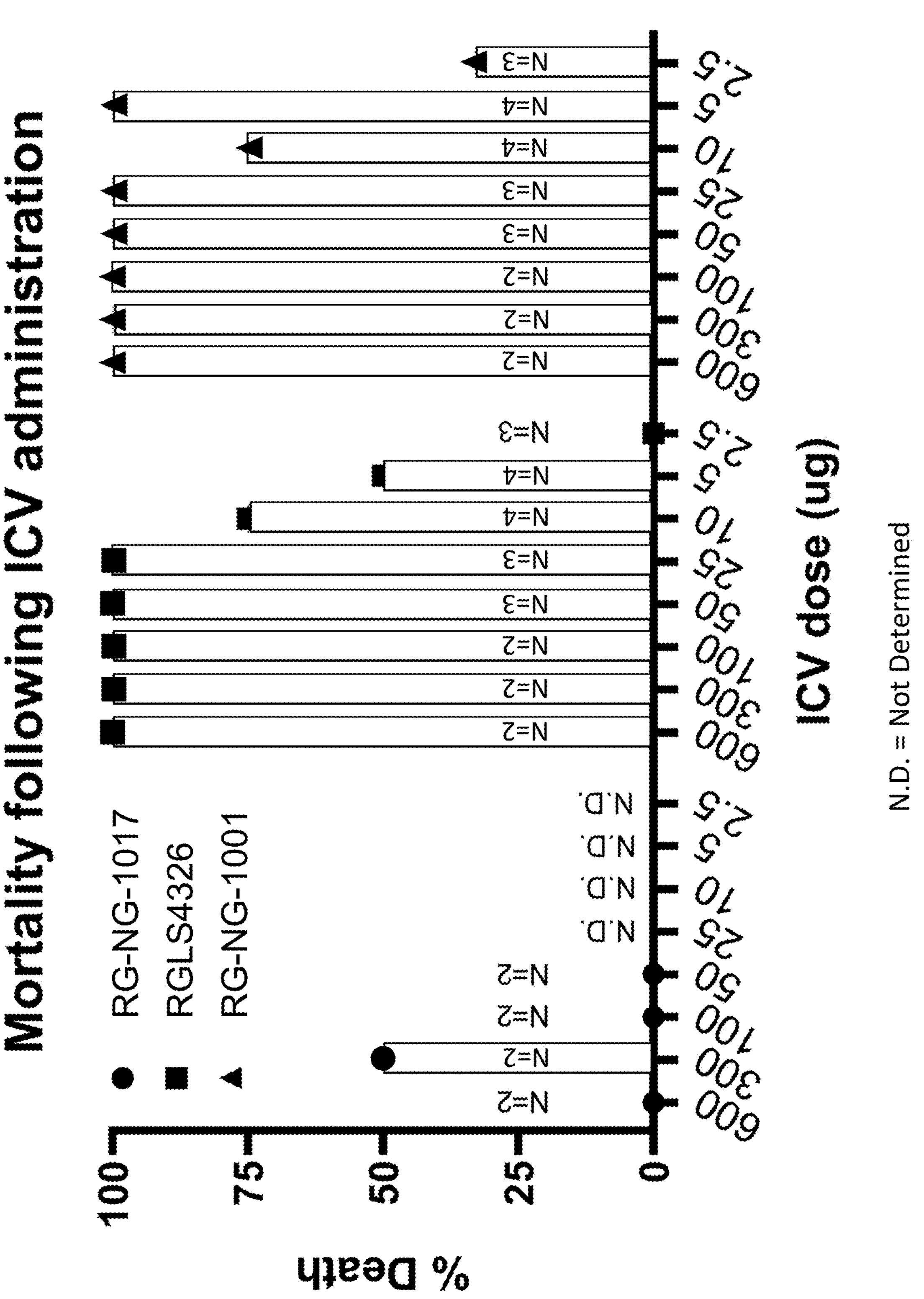
FIG. 3. Maximum Tolerated Dose (MTD) study and Comparative Dose Assessment of RG-NG-1001, RGLS4326, and RG-NG-1017. 6-7-week-old male C57BL/6J mice were dosed with a single intracerebroventricular (ICV) injection of RG-NG-1001 and RGLS4326 (anti-miR-17 oligos that inhibit AMPA-R) and RG-NG-1017 (anti-miR-17 oligos that does not inhibit AMPA-R; RG-NG-1017) at different dose levels in 4 μL volume and monitored for 7 days. Mortality of the mice is indicated for the three different compounds at different dosages.
Figure 4A:
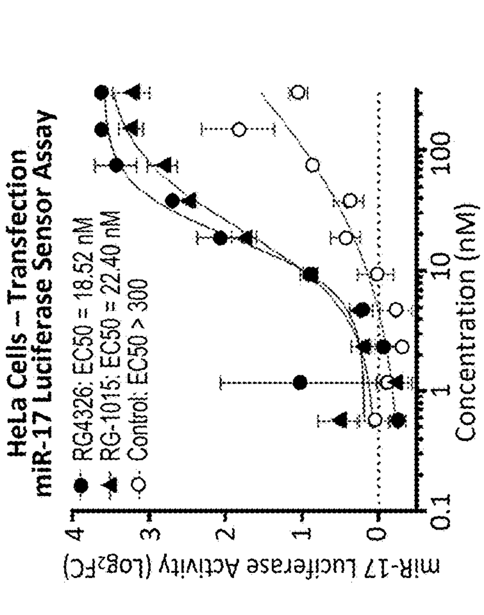
FIG. 4A-4F. Assessment of activity of RG-NG-1015 and RGLS4326 against miR-17 (4A), miR-20a (4B), miR-93 (4C), and miR106 (a) (4D) luciferase sensors activity in HeLa cells in vitro is set forth. Assessment of activity of RG-NG-1015 and RGLS4326 against luciferase sensors containing full length 3' untranslated region (UTR) of the miR-17 direct target genes PKD1 (4E) and PKD2 (4F) is set forth.
Figure 4B:
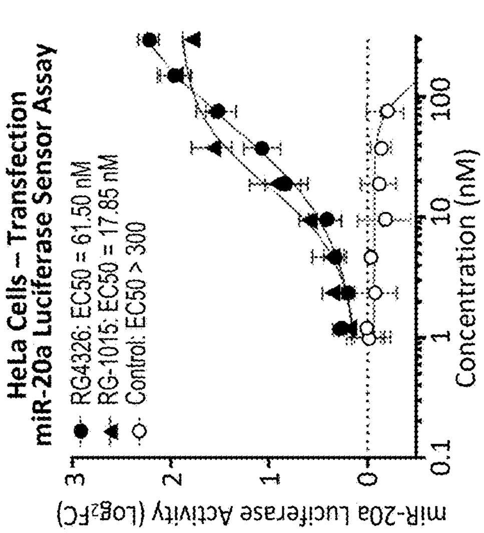
Figure 4C:
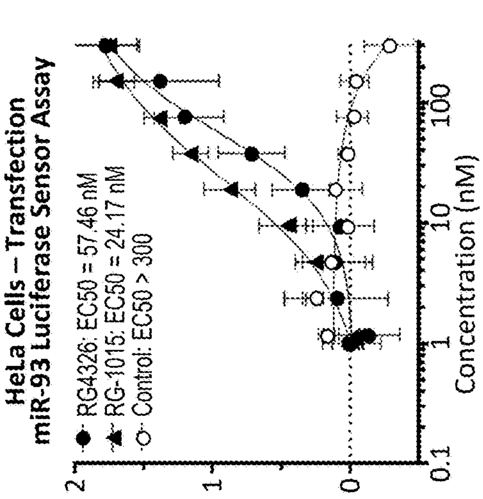
Figure 4D:
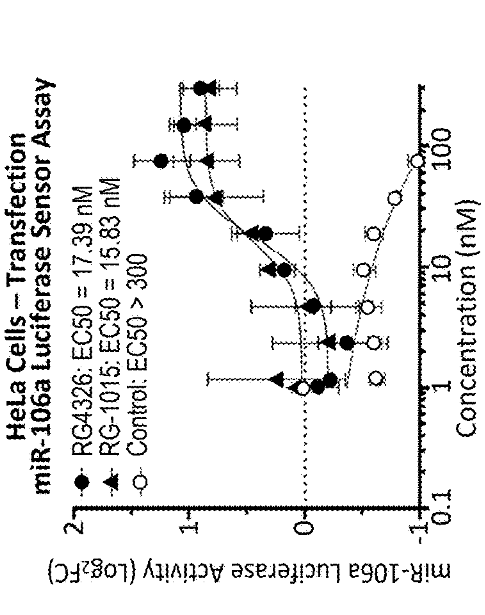
Figure 4E:
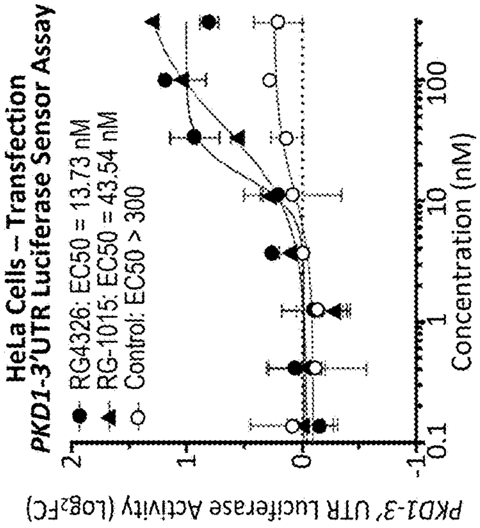
Figure 4F:
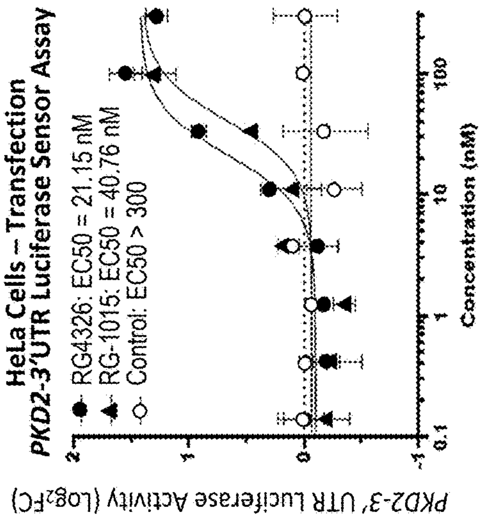
Figure 5A:
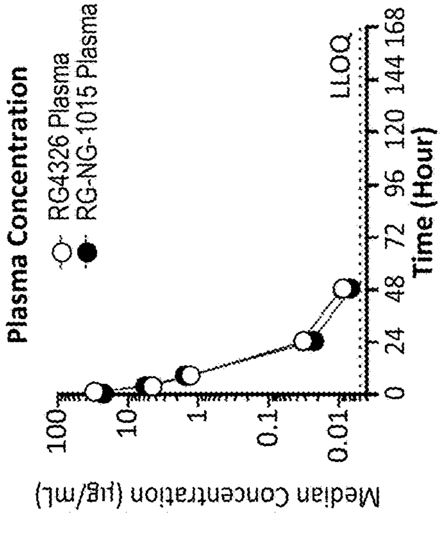
FIG. 5A-5D. Pharmacokinetic and target engagement (as measured by miPSA) of RGLS4326 and RG-NG-1015 following a single subcutaneous administration in C57BL6 mice were measured. Plasma concentration (5A), tissue concentration (5B), kidney target engagement (5C), and liver target engagement (5D) are shown.
Figure 5B:
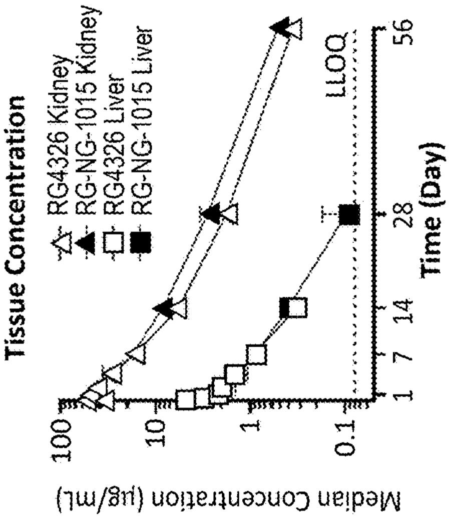
Figure 5C:
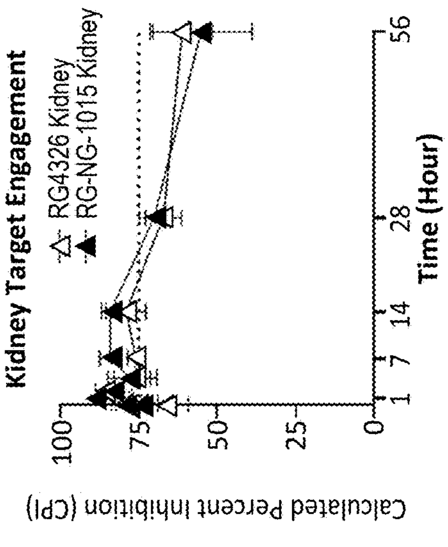
Figure 5D:
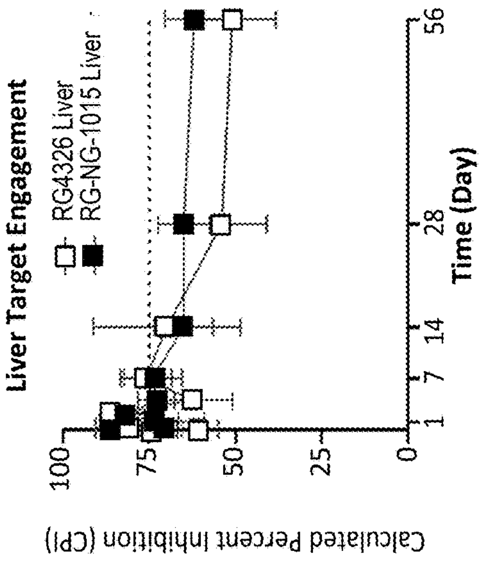

Results from the MTD study are shown in Table 10 and FIG. 3. All animal deaths were reported to occur within the first 5-8 hours post-ICV injection. Mice injected with 2.5 μg RG4326 were reported to display some immediate signs of respiratory distress and were provided heating pads. RG-NG-1017 (non-AMPA-R binding compound) was well-tolerated at high doses, with no established MTD for this compound (0 deaths at 600 μg, 100 μg, or 50 μg; 1 death at 300 μg). 100% mortality was observed at high doses for RG4326 and RG-NG-1001 (e.g., 600, 300, 100 μg), in addition to 100% mortality observed at 50 μg and 25 μg for both AMPA-R binding compounds. RG-NG-1001 MTD was not attained in this study, and was predicted to be under 2.5 μg. The MTD for RG4326 was predicted at ~2.5<5.0 μg by ICV. All animals were reported to fully recover on Day 2 of observation.

TABLE 10

| Summary Results from 7-day MTD Study | | | |
|---|---|---|---|
| Dose | Mortality/total number of mice | | |
| (μg) | RG-NG-1017 | RGLS4326 | RG-NG-1001 |
| 600 | 0/2 | 2/2 | 2/2 |
| 300 | 1/2 | 2/2 | 2/2 |
| 100 | 0/2 | 2/2 | 2/2 |
| 50 | 0/2 | 3/3 | 3/3 |
| 25 | | 3/3 | 3/3 |
| 10 | | 3/4 | 3/4 |
| 5 | | 2/4 | 4/4 |
| 2.5 | | 0/3 | 1/3 |

Maximum Tolerated Dose (MTD) Study for RGLS4326

A second MTD study for RGL4326 by ICV was conducted to assess dose selection for evaluating the compound in disease models (Table 11). In this study, a different mouse strain was evaluated (Swiss:Rjorl male mice, age 5 weeks, sourced from Janvier). Mice were placed under isoflurane anaesthesia (5% for induction and 2% for maintenance, under 100% O2) and given 5 mg/kg s.c. carprofen (Rimadyl®). They were then placed in a stereotaxic frame. A midline sagittal incision was made in the scalp and a hole was drilled in the skull over the left lateral ventricle. A stainless-steel cannula (external diameter 0.51 mm) was placed stereotaxically into the left lateral ventricle at the following coordinates: +0.5 posterior to Bregma, L±0.7 mm, V=−2.7 mm. After a 2-minute delay to allow the brain tissue to slide over the cannula, 4 μL of a solution containing 0.625 mg/mL of RG4326 was slowly infused over 2 minutes. After infusion, the cannula was left in place for a further 5 minutes to prevent backflow of the solution along the cannula track. Mice were given 5 mg/kg s.c. carprofen (Rimadyl®) at 24 and 48 hours, after surgery. Mice were monitored during 3-7 days after surgery (starting 24 h after ICV administration) and their body weight was taken daily to check their health status. For mice monitored over 7 days, body weight was taken on Day 1 and on Day 7 after surgery to check their health status.

TABLE 11

| Design of MTD Study for RGLS4326 | | | | | |
|---|---|---|---|---|---|
| Group | Number of animals | Treatment (RG4326) | Dose-level | Concentration (mg/mL) | Administration Volume |
| 1 | 4 males | RG4326 (i.c.v.) | 3 mg/mouse | 0.75 mg/mL | 4 mL/mouse |
| 2 | 4 males | RG4326 (i.c.v.) | 4 mg/mouse | 1 mg/mL | 4 mL/mouse |
| 3 | 4 males | RG4326 (i.c.v.) | 5 mg/mouse | 1.25 mg/mL | 4 mL/mouse |
| 4 | 4 males | RG4326 (i.c.v.) | 7.5 mg/mouse | 1.875 mg/mL | 4 mL/mouse |

In Study 1, 6 mice were injected with 4 μL of a solution at 0.625 mg/mL (2.5 μg total per ICV; Table 10). At the end of anesthesia, the mice remained lying on one side. They were quiet with some periods of scratching during the first hours after surgery. No toxic effects were observed at 24, 48 or 72 hours in the 6 mice administered. In Study 2, four mice were injected with 4 different doses of RGLS4326 (0.75, 1.0, 1.25 and 1.875 mg/mL, volume of 4 μL). One mouse that received the highest dose (1.875 mg/mL, i.e., 7.5 μg/mouse) was found dead around 24 hours after ICV injection. All other mice were in good health, until the end of the pilot study (7 days after administration).

Combined results from Studies 1 and 2 demonstrated that RG4326 was generally well-tolerated in test subjects, but only at doses considerably lower than RG-NG-1017 (see FIG. 3).

Table 12 summarizes the MTD data for RGLS4326 for the Study 1 and 2 mouse models. Based on these results from Study 2, an MTD of ~4 μg was predicted for RGLS4326 in the Swiss:Rjorl mouse strain.

TABLE 12

| 7-Day Survival Data for MTD Studies 1 and 2 | | |
|---|---|---|
| Dose (μg) | Dead/Total Mice | |
| RGLS4326 | Study 1 | Study 2 |
| 600 | 2/2 | |
| 300 | 2/2 | |
| 100 | 2/2 | |
| 50 | 3/3 | |
| 25 | 3/3 | |
| 10 | 3/4 | |
| 7.5 | — | 1/4 |
| 5 | 2/4 | 0/4 |
| 4 | | 0/4 |
| 3 | | 0/4 |
| 2.5 | 0/3 | 0/6 |

In summary, compounds RG-NG-1017, RGLS4326 and RG-NG-1001 were evaluated across two MTD studies, demonstrating significant differences in tolerability between non-AMPA-R binding (RG-NG-1017) and AMPA-R binding compounds (RGLS4326, RG-NG-1001) (see FIG. 3). Despite 1 death at the ICV dose of 300 μg, an MTD was not established for RG-NG-1017, as no deaths occurred at the higher tested dose of 600 μg. Additionally, no impact on mortality was observed at doses of 100 and 50 μg for RG-NG-1017. By comparison, a clear impact on mortality was evident for the AMPA-R binding compounds RGLS4326 and RG-NG-1001, with no surviving animals across the tested dosing range of 25 μg to 600 μg. A trend for improved survival was seen at lower doses of RGLS4326 (10 μg), with 50% survival in RGLS4326 treated animals at 5 μg, and 100% survival at 2.5 μg. Similarly, in the case of RG-NG-1001 (which shows stronger AMPA-R binding compared to RGLS4326), 100% mortality was evident at the low dose of 5 μg, with a trend toward improved survival at 2.5 μg. The results for RGLS43426 from Study 1 were further confirmed in a second MTD study (Study 2), utilizing a different mouse strain. This study found that modest differences may exist for RGLS4326 tolerability between strains, with survival observed to only impact mice at the top dose of 7.5 μg versus at 5 μg in Study 1 using C57/Bl/6J. However, these results still support that MTD for the AMPA-R binding RGLS4326 occurs between ~2.5 μg and 5-7.5 μg (depending on strain), as compared to a significantly higher MTD for non-AMPA-R binding RG-NG-1017 (at least >40-fold, or higher) (FIG. 3).

Example 6: In Vitro and In Vivo Potency of Anti-miR-17 Compounds

The in vitro potency of certain compounds was evaluated using a miR-17 luciferase sensor assay which uses a luciferase reporter vector for miR-17, with two fully complementary miR-17 binding sites in tandem in the 3'-UTR of the luciferase gene. HeLa cells were co-transfected with the luciferase reporter vector and an exogenous miR-17-expression vector that acted to repress the luciferase signal. HeLa cells were then individually treated with anti-miR-17 oligonucleotides at concentrations of 0.045, 0.137. 0.412, 1.23, 3.70, 11.1, 33.3, 100, and 300 nM. At the end of the 18- to 24-hour transfection period, luciferase activity was measured. RG5124 was included as a control compound. As shown in Table 13, these compounds inhibited miR-17 function and de-repressed miR-17 luciferases reporter activity with similar $EC_{50}$ values compared to RGLS4326 in vitro.

TABLE 13

| Inhibition of miR-17 in Luciferase Assay | | |
|---|---|---|
| Compound ID | EC50 (nM) | Log2FC (37.5 nM) |
| RGLS4326 | 18.50 | 2.70 |
| RG-NG-1032 | <1 | 3.85 |
| RG-NG-1015 | 22.40 | 2.51 |
| RG-NG-1016 | 20.30 | 2.32 |
| RG-NG-1017 | 15.00 | 2.67 |
| RG5124 | n/a | 0.40 |

As shown in FIG. 4, RG-NG-1015 inhibited miR-17, as well as miR-20a, miR-106a, and miR-93 in a luciferase assay in Hela cells, with similar $EC_{50}$ values compared to RGLS4326 in vitro. RG-NG-1015 also de-repressed luciferase sensors containing full-length 3' untranslated region (UTR) of the miR-17 direct target genes PKD1 and PKD2, with similar $EC_{50}$ values compared to RGLS4326 in vitro.

The activity of certain compounds was evaluated using a mouse miR-17 Pharmacodynamic-Signature (miR-17 PD-Sig), which consists of the expression of 18 unique miR-17 target genes normalized by six reference housekeeping genes, to provide an unbiased and comprehensive assessment of miR-17 activity. The mouse miR-17 PD-Sig score was the calculated average of the 18 genes' individual log 2 fold changes (normalized by six housekeeping genes) compared to mock transfection (Lee et al., *Nat. Commun.,* 2019, 10, 4148).

As shown in Table 13, the tested oligonucleotides inhibited miR-17 function and de-repressed expression of multiple direct miR-17 target genes (as measured by miR-17 PD-signature) in normal and PKD kidney cell lines (both mouse and human) with similar $EC_{50}$ values compared to RGLS4326 in vitro. The PD-Sig for RGLS4326 in mIMCD3 cells (77.2, indicated by "*") was not generated in this experiment; the value in Table 14 is that reported by Lee et al., *Nat. Commun.,* 2019, 10, 4148. Blank cells in the table indicate that a compound was not tested in a particular cell line.

TABLE 14 miR-17 PD-Sig in Normal and PKD Cell Lines

| | | | Anti-miR | | | | |
|---|---|---|---|---|---|---|---|
| Cell Line | Species | Derived from | RGLS4326 | RG-NG-1015 | RG-NG-1016 | RG-NG-1017 | RG5124 |
| mIMCD3 | mouse | Normal | 77.2* | 168 | 146.3 | 134.5 | n/a |
| D52B5 | mouse | PKD | 92.8 | 82.4 | | 74.1 | 506.6 |
| HK-2 | human | Normal | 47.8 | 55.6 | | 49.2 | |
| WT9-7 | human | PKD | 17.3 | 21.2 | | 20.1 | |

TABLE 15 miPSA Displacement Scores

| | | anti-miR Dose | | | |
|---|---|---|---|---|---|
| | | | 0.3 m/kg | 3 mg/kg | 30 mg/kg |
| RG-NG-1015 | Mean | | 2.238 | 2.562 | 2.718 |
| | SEM | | 0.1242 | 0.1303 | 0.118 |
| RG-NG-1016 | Mean | | 1.892 | 2.263 | 1.134 |
| | SEM | | 0.1088 | 0.1716 | 0.5324 |
| RG-NG-1017 | Mean | | 2.077 | 2.292 | 2.793 |
| | SEM | | 0.1513 | 0.08974 | 0.09685 |
| RGLS4326 | Mean | | 1.846 | 2.247 | 2.362 |
| | SEM | | 0.1234 | 0.0478 | 0.1439 |
| Vehicle (PBS) | Mean | 0 | | | |
| | SEM | 0.06318 | | | |
| RG5124 | Mean | | | | 0.5935 |
| | SEM | | | | 0.1784 |

Furthermore, as shown in Table 16 and FIG. 5A-5D, RGLS4326 and RG-NG-1015 have similar pharmacokinetic and Target Engagement (as measured by miPSA) profiles following a single subcutaneous administration in C57BL6 mice.

TABLE 16 pharmacokinetic and Target Engagement profiles

| Tissue | Test Article | Dose | $T_{max}$ | $C_{max}$ | $AUC_{last}$ | $T_{1/2}$ | Kidney-to-Liver Ratio by $AUC_{last}$ |
|---|---|---|---|---|---|---|---|
| Plasma | RGLS4326 | 26.0 mg/kg | 1 h | 32 mg/mL | 95.3 (mg * h)/mL | 2.9 h | — |
| | RG-NG-1015 | 26.9 mg/kg | 1 h | 26 mg/mL | 86.9 (mg * h)/mL | 2.6 h | — |
| Kidney | RGLS4326 | 26.0 mg/kg | 8 h | 54 mg/g | 395 (mg * d)/g | 9.4 d | 23.9 |
| | RG-NG-1015 | 26.9 mg/kg | 8 h | 53 mg/g | 447 (mg * d)/g | 9.9 d | 22.6 |
| Liver | RGLS4326 | 26.0 mg/kg | 1 h | 4.8 mg/g | 16.5 (mg * d)/g | 4.7 d | — |
| | RG-NG-1015 | 26.9 mg/kg | 1 h | 5.2 mg/g | 19.8 (mg * d)/g | 6.2 d | — |

In vivo potency was evaluated using the microRNA polysome shift assay (miPSA). This assay was used to determine the extent to which compounds directly engage the miR-17 target in the kidney in normal and PKD mice. The miPSA relies on the principle that active miRNAs bind to their mRNA targets in translationally active high molecular weight (HMW) polysomes, whereas the inhibited miRNAs reside in the low MW (LMW) polysomes. Treatment with anti-miR results in a shift of the microRNA from HMW polysomes to LMW polysomes. Thus, the miPSA provides a direct measurement of microRNA target engagement by a complementary anti-miR (Androsavich et al., *Nucleic Acids Research,* 2015, 44: e13).

Wild type mice were administered a single dose of 0.3 mg/kg, 3 mg/kg, or 30 mg/kg. Kidney tissue was collected seven days later and subjected to the miPSA. The mean displacement score for each treatment is shown in Table 15 (PBS, n=17; RGLS4326 30 mg/kg, n=10; all other treatments, n=4-5). The tested oligonucleotides displaced miR-17 from translationally active polysome (as measured by miPSA) in normal mouse kidneys.

Example 7: Efficacy of RG-NG-1015 in an Experimental Model of ADPKD

The efficacy of RG-NG-1015 was evaluated in the KspCre/PkdIF/RC (Pkd1-F/RC) mouse model. Pkd1-F/RC is an orthologous ADPKD model that contains a germline hypomorphic Pkd1 mutation (the mouse equivalent of the human PKD1-R3277C (RC mutation) on one allele and loxP sites flanking Pkd1 exons 2 and 4 on the other allele. KspCre-mediated recombination was used to delete the floxed Pkd1 exons and produce a compound mutant mouse with a renal tubule-specific, somatic null mutation on one allele and a germline hypomorphic mutation on the other. This is an aggressive, but long-lived model of ADPKD (Hajarnis et al., *Nat. Commun.,* 2017, 8, 14395).

On each of days 8, 10, 12, and 15 of age, sex-matched of Pkd1-F/RC mice were administered a subcutaneous injection of RGLS4326 at a dose of 20 mg/kg (n=8; 4 males and 4 females per treatment group), RG5124 at a dose of 20 mg/kg (n=8), or RG-NG-1015 at a dose of 20 mg/kg (n=8), or PBS (n=8). Mice were sacrificed at 18 days of age, and kidney weight, body weight, cyst index, serum creatinine level, and blood urea nitrogen (BUN) level were measured. BUN level is a marker of kidney function. A higher BUN level correlates with poorer kidney function, thus a reduction in BUN level is an indicator of reduced kidney injury and damage and improved function. Statistical significance was calculated by one-way ANOVA with Dunnett's multiple correction.

Figure 2A:
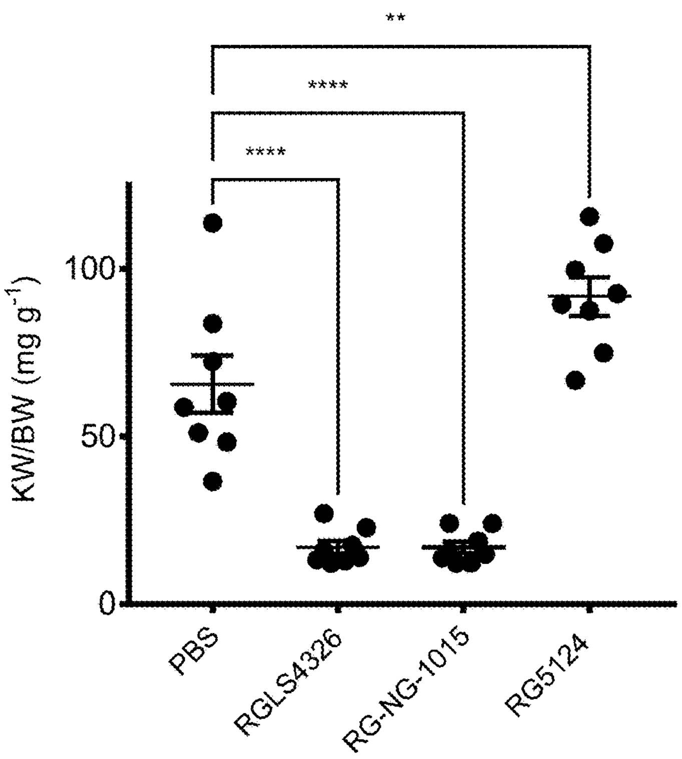
FIG. 2A-2C. Efficacy of RG-NG-1015 in the Pkd1-F/RC model of PKD. Effects of treatment on (2A) kidney-to-body weight ratio, (2B) blood urea nitrogen (BUN) level, and (2C) blood creatinine level.
Figure 2B:
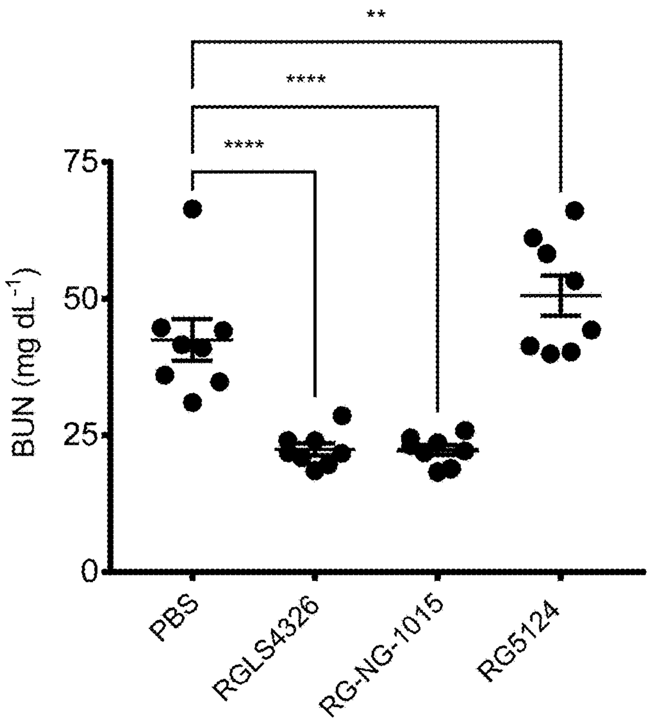
Figure 2C:
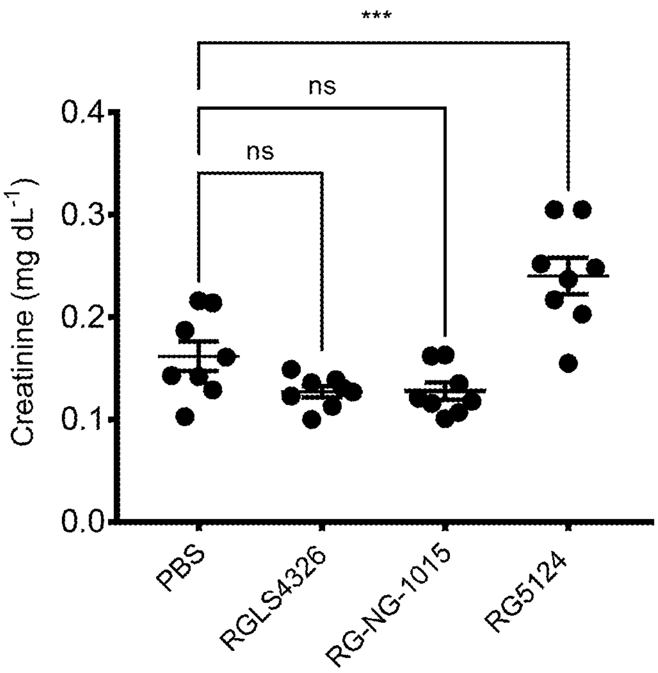

Results are shown in Table 17 and FIG. 2 (**=p<0.0001; *=p<0.001; =p<0.01; ns=not significant). The efficacy of RG-NG-1015 was similar to that of RGLS4326. The mean ratio of kidney weight to body weight (KW/BW ratio) was significantly lower in Pkd1-F/RC mice treated with RGLS4326 and RG-NG-1015, respectively, than the mean KW/BW ratio in Pkd1-F/RC mice administered PBS (FIG. 2A). Mean BUN levels were significantly reduced in Pkd1-F/RC mice treated with RGLS4326 and RG-NG-1015, respectively, compared to mice treated with PBS (FIG. 2B). Mean serum creatinine levels in Pkd1-F/RC mice were reduced in mice treated with RGLS4326 and RG-NG-1015, respectively, relative to mice treated with PBS, however the reduction was not statistically significant (FIG. 2**C). Treatment with the control oligonucleotide, RG5124, did not reduce kidney weight to body weight ratio, serum creatinine, or serum BUN, demonstrating that the results observed with RGLS4329 and RG-NG-1015 were specific to the inhibition of miR-17.

TABLE 17

Efficacy of RG-NG-1015 in a Mouse Model of ADPKD

| | PBS | RGLS4326 | RG-NG-1015 | RG5124 |
|---|---|---|---|---|
| Mean BW/KW Ratio | 65.61 | 16.81 | 16.83 | 91.75 |
| Mean Difference vs. PBS | | −48.8 | −48.79 | 26.14 |
| Adjusted P-Value | | <0.0001 | <0.0001 | 0.0045 |
| Mean Serum BUN | 42.48 | 22.41 | 22.26 | 50.61 |
| Mean Difference vs. PBS | | −20.06 | −20.21 | +8.138 |
| Adjusted P-Value | | <0.0001 | <0.0001 | 0.1142 |
| Mean Serum Creatine | 0.1619 | 0.1273 | 0.1279 | 0.2403 |
| Mean Difference vs. PBS | | −0.03463 | −0.03400 | +0.07838 |
| Adjusted P-Value | | 0.1456 | 0.1557 | 0.0004 |

The efficacy of RG-NG-1015 was also evaluated in the Pcy/DBA mouse model of PKD alone and in combination with tolvaptan. Pcy/DBA mice exhibit slowly progressing PKD caused by a missense mutation in the Nphp3 gene, which is responsible for adolescent nephronophthisis in humans (Takahashi et al., *J Am Soc Nephrol* 1991, 1:980-989; Olbrich et al., *Nat Genet* 2003, 34:455-459). In Pcy mice, cysts are derived from distal tubules, and whole-nephron segments become diffusely occupied by cysts accompanying disease progression by 30 weeks of age, often with the occurrence of ESRD (Nagao et al., *Exp Anim* 2012, 61:477-488). In particular, male Pcy/DBA mice has been used to characterize the pharmacological profiles of many investigational products for ADPKD treatment, including tolvaptan and RGLS4326, the first-generation anti-miR-17 (Aihara et al., *J Pharmacol Exp Ther* 2014 May; 349(2):258-67 and Lee et al., *Nat. Commun.*, 2019, 10, 4148). Studies in these mice typically involve initiation of treatment at ~5 weeks of age and continues through to 15-30 weeks of age.

Figure 6A:
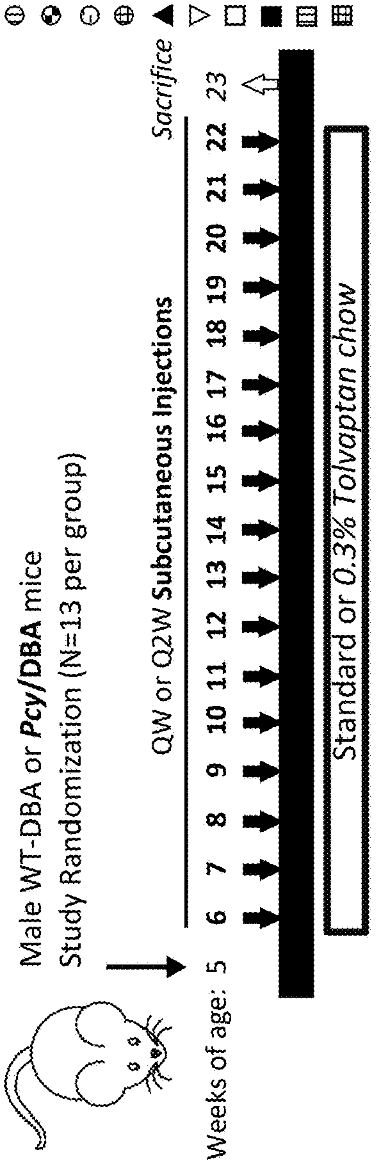
FIG. 6A-6E. Effect of RG-NG-1015 at different dosages and regimens and in combination with tolvaptan on Pcy/DBA mouse model of PKD was measured. The dosing schedule is shown in FIG. 6A, and the key to the graphs in FIGS. 6C-6E is shown in FIG. 6B. Kidney weight/body weight (6C), cystic area (%) (6D), and urine Ngal/Cr (6E) are shown. Error bars represent standard deviations. *$p<0.05$, $p<0.01$, *$p<0.001$, ****$p<0.001$, (ns)$p>0.05$ compared to Pcy vehicle treated group; One-way ANOVA Bonferroni's multiple comparison test. #$p<0.05$, ##$p<0.01$, ###$p<0.001$, ####$p<0.001$, (ns)$p>0.05$ compared to Tolvaptan alone treated group; One-way ANOVA Sadik's multiple comparison test. \$$p<0.05$, \$\$$p<0.01$, \$\$\$$p<0.001$, \$\$\$\$$p<0.001$, (ns)$p>0.05$ compared to dose-matched RG-NG-1015 alone treated group; One-way ANOVA Sadik's multiple comparison test.
Figure 6B:
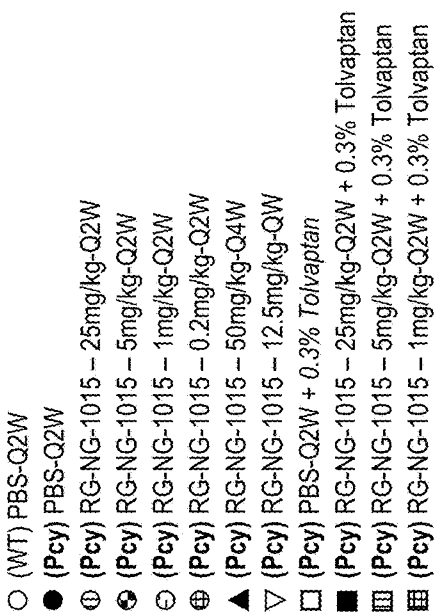

As outlined in FIGS. 6A and 6B, five groups of male Pcy/DBA mice (n=13 per treatment group) were treated subcutaneously with PBS or RG-NG-1015 at 25, 5, 1, or 0.2 mg/kg once every two weeks (Q2W). Two groups of male Pcy/DBA mice (n=13 per group) were also treated with RG-NG-1015 at 50 mg/kg once every four weeks (Q4W) or at 12.5 mg/kg once weekly (QW). Another four groups of male Pcy/DBA mice (n=13 per group) were treated subcutaneously with PBS or RG-NG-1015 at 25, 5, or 1 mg/kg Q2W in combination with tolvaptan at 0.3% (w/w chow) ad libitum. A group of male WT-BDA/2J mice received subcutaneous injections of PBS Q2W was included in the study as a normal range reference. Mice were randomized into treatment groups at 5 weeks of age, and treatment started at 6 weeks of age for 17 weeks and were sacrificed 7 days after the final treatment. Kidney weight, body weight, kidney cyst index, urine Ngal-to-Creatinine ratio (Ngal/Cr) were measured. Urine Ngal/Cr is a marker of kidney injuries.

Figure 6C:
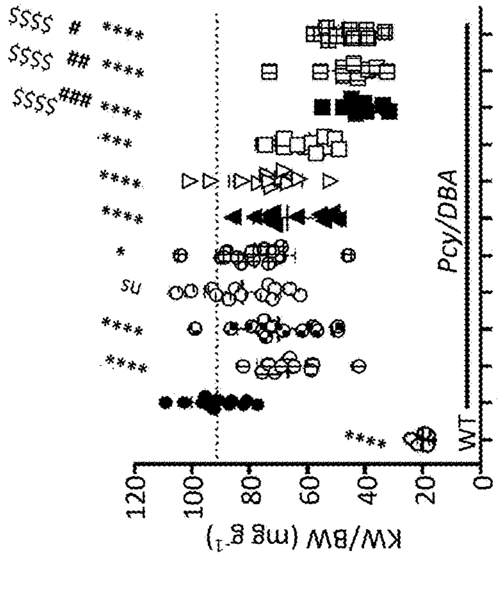
Figure 6D:
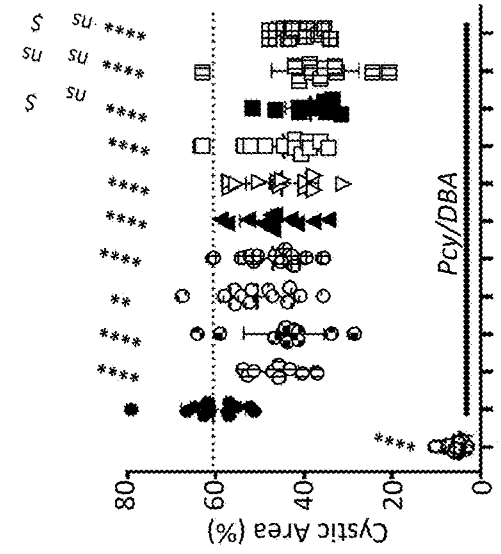
Figure 6E:
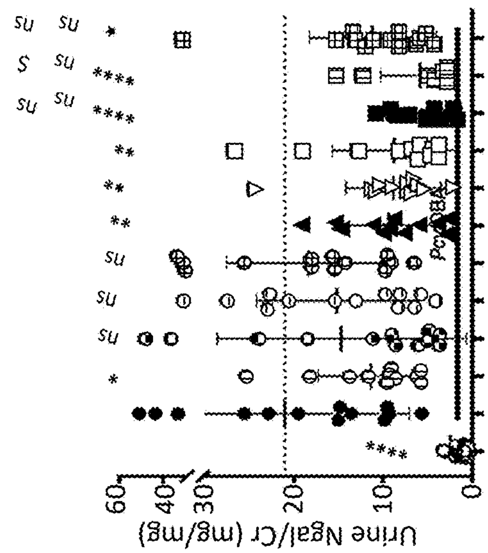

As seen in FIG. 6C-6E and Tables 18-20, RG-NG-1015 is effective in the Pcy/DBA mouse model of PKD at various dosages and regiments, and also provides additive or synergistic effects when used in combination with tolvaptan. In particular, RG-NG-1015 treatment significantly reduced mean KW/BW, urine Ngal/Cr, and kidney cyst index in Pcy/DBA mice in a dose-dependent manner (Table 18 and FIG. 6C-6E). In addition, RG-NG-1015 treatment by similar total dosage (total of 212.5-250 mg per mouse for the duration of the study) but different dosing regiments (including QW, Q2W, and Q4W) reduced mean KW/BW, urine Ngal/Cr, and kidney cyst index at similar levels in Pcy/DBA mice (Table 19; FIG. 6C-6E). Treatment with tolvaptan alone reduced mean KW/BW, urine Ngal/Cr and kidney cyst index in Pcy/DBA mice, and combination of RG-NG-1015 plus tolvaptan further reduced mean KW/BW, urine Ngal/Cr, and kidney cyst index (Table 20; FIG. 6C-6E). The observed effects of the drug combination on KW/BW, urine Ngal/Cr, and kidney cyst index were synergistic, mostly additive, and less than additive, respectively, as indicated by Bliss additivity analysis (Table 20).

TABLE 18

Effects of Dose

| Test Article 1 | Test Article 2 Chow | | | Mean KW/BW | | Mean Urine Ngal/Cr | | Mean Cystic Area | |
|---|---|---|---|---|---|---|---|---|---|
| SC Dosing | Supl. | Dose | Regimen | mg/kg | % Inhibition | mg/mg | % Inhibition | % | % Inhibition |
| Vehicle | — | — | Q2 W | 91.3 | 0 | 21.07 | 0 | 60.62 | 0 |
| RG-NG-1015 | — | 25 mg/kg | Q2 W | 66.87 | 34.3 | 11.36 | 48.8 | 46.46 | 26.0 |

TABLE 18-continued

Effects of Dose

| Test Article 1 SC Dosing | Test Article 2 Chow Supl. | Dose | Regimen | Mean KW/BW mg/kg | Mean KW/BW % Inhibition | Mean Urine Ngal/Cr mg/mg | Mean Urine Ngal/Cr % Inhibition | Mean Cystic Area % | Mean Cystic Area % Inhibition |
|---|---|---|---|---|---|---|---|---|---|
| RG-NG-1015 | — | 5 mg/kg | Q2 W | 70.02 | 29.9 | 14.65 | 32.3 | 44.58 | 29.4 |
| RG-NG-1015 | — | 1 mg/kg | Q2 W | 82.43 | 12.5 | 15.18 | 29.6 | 50.58 | 18.4 |
| RG-NG-1015 | — | 0.2 mg/kg | Q2 W | 78.02 | 18.7 | 18.38 | 13.5 | 47.09 | 24.8 |

TABLE 19

Effects of Regimen

| Test Article 1 SC Dosing | Test Article 2 Chow Supl. | Dose | Regimen | Mean KW/BW mg/kg | Mean KW/BW % Inhibition | Mean Urine Ngal/Cr mg/mg | Mean Urine Ngal/Cr % Inhibition | Mean Cystic Area % | Mean Cystic Area % Inhibition | Number of doses | Total doses (mg) |
|---|---|---|---|---|---|---|---|---|---|---|---|
| Vehicle | — | — | Q2 W | 91.3 | 0 | 21.07 | 0 | 60.62 | 0 | 17 | |
| RG-NG-1015 | — | 25 mg/kg | Q2 W | 66.87 | 34.3 | 11.36 | 48.8 | 46.46 | 26.0 | 9 | 225 |
| RG-NG-1015 | — | 50 mg/kg | Q4 W | 67.09 | 34.0 | 9.32 | 59.1 | 47.35 | 24.3 | 5 | 250 |
| RG-NG-1015 | — | 12.5 mg/kg | QW | 74.52 | 23.6 | 8.82 | 61.6 | 44.99 | 28.7 | 17 | 212.5 |

TABLE 20

Effects of Combination

| Test Article 1 SC Dosing | Test Article 2 Chow Suppl. | Dose | Regimen | Mean KW/BW mg/kg | Mean KW/BW % Inhibition | Mean KW/BW Bliss Analysis | Mean Urine Ngal/Cr mg/mg | Mean Urine Ngal/Cr % Inhibition | Mean Urine Ngal/Cr Bliss Analysis | Mean Cystic Area % | Mean Cystic Area % Inhibition | Mean Cystic Area Bliss Analysis |
|---|---|---|---|---|---|---|---|---|---|---|---|---|
| Vehicle | — | — | Q2 W | 91.3 | 0 | — | 21.07 | 0 | — | 60.62 | 0 | — |
| Vehicle | 0.3% Tolvaptan | — | — | 59.26 | 44.9 | — | 8.73 | 62.1 | — | 44.68 | 29.2 | — |
| RG-NG-1015 | — | 25 mg/kg | Q2 W | 66.87 | 34.3 | — | 11.36 | 48.8 | — | 46.46 | 26.0 | — |
| RG-NG-1015 | 0.3% Tolvaptan | 25 mg/kg | Q2 W | 42.21 | 68.9 | Synergistic | 5.04 | 80.6 | Additive | 38.61 | 40.4 | <Additive |
| RG-NG-1015 | — | 5 mg/kg | Q2 W | 70.02 | 29.9 | — | 14.65 | 32.3 | — | 44.58 | 29.4 | — |
| RG-NG-1015 | 0.3% Tolvaptan | 5 mg/kg | Q2 W | 45.62 | 64.1 | Synergistic | 5.84 | 76.6 | Additive | 37.47 | 42.5 | <Additive |
| RG-NG-1015 | — | 1 mg/kg | Q2 W | 82.43 | 12.5 | — | 15.18 | 29.6 | — | 50.58 | 18.4 | — |
| RG-NG-1015 | 0.3% Tolvaptan | 1 mg/kg | Q2 W | 47.11 | 62.0 | Synergistic | 11.16 | 49.8 | <Additive | 41.91 | 34.3 | <Additive |

Example 8: Metabolites of RG-NG-1015

In vitro and in vivo studies were conducted to investigate the metabolism of RG-NG-1015. For both in vitro and in vivo samples, tissue samples were homogenized in lysis buffer on ice and RG-NG-1015 and/or metabolites were isolated from plasma, tissue homogenates, or urine via liquid-liquid extraction and solid-phase extraction steps. Calibration samples containing known amounts of RG-NG-1015 were extracted in parallel with test tissue homogenates, plasma, or urine samples. The molecular weight (MW) of RG-NG-1015 and potential metabolites were calculated from the MS signal and compared with theoretical values.

The in vitro metabolic stability of RG-NG-1015 was assessed in mouse, monkey, and human tissues (i.e., kidney and liver lysates) as well as serum. RG-NG-1015 was incubated in these matrices at a concentration of 5 μM with kidney and liver homogenates (corresponding to 307 μg/g tissue) or serum samples (corresponding to 15.3 μg/mL) for 24 hours at 37° C. RG-NG-1015 and metabolites were then extracted and analyzed by HPLC-TOF.

In vivo metabolism was evaluated in liver and kidney after a single dose of RG-NG-1015 to CD-1 mice, and in plasma, tissues, and urine after single and/or repeated administration to monkeys. CD-1 mice received a single SC dose of RG-NG-1015 at 2000 mg/kg, and monkeys received up to 5 weekly SC doses of RG-NG-1015 at 15, 75, or 150 mg/kg. RG-NG-1015 and metabolites were then extracted and analyzed by HPLC-TOF.

RG-NG-1015 undergoes sequential hydrolysis from both 3' and 5' ends to produce chain-shortened metabolites (See Table 21). Nine potential metabolites were identified: 5' N-1, 5' N-2, 5' N-3, 5' N-4, 3' N-1, 3' N-2, 3' N-3, 3' N-4, and 3' N-5 as set forth below in Table 21. All metabolites differed from RG-NG-1015 by sequential removal of terminal nucleotides and are terminated in hydroxyl groups on the 3' and 5' ends. 5' end shortmers (from N-5 to N-8) and 3' end shortmers (from N-6 to N-8) were not observed.

TABLE 21

Sequences, exact mass of neutral molecule, m/z and charge state of RG-NG-1015 and its potential metabolites

| Compound Name | SEQ ID NO | Compound Sequence (5'->3')* | Exact Mass of Neutral Molecule | Mass to Charge Ratio (m/z) | Charge State | Comment |
|---|---|---|---|---|---|---|
| RG-NG-1015 | | $A_SG_SC_MA_FC_FU_FU_MU_SA_S$ | 3064.31 | 1531.15 | −2 | Parent Molecule |
| 3'N − 1 | | $A_SG_SC_MA_FC_FU_FU_MU_S$ | 2693.26 | 1345.63 | −2 | Metabolite |
| 3'N − 2 | | $A_SG_SC_MA_FC_FU_FU_M$ | 2345.24 | 1171.62 | −2 | Metabolite |
| 3'N − 3 | | $A_SG_SC_MA_FC_FU_F$ | 2009.22 | 1003.61 | −2 | Metabolite |
| 3'N − 4 | | $A_SG_SC_MA_FC_F$ | 1685.23 | 841.61 | −2 | Metabolite |
| 3'N − 5 | | $A_SG_SC_MA_F$ | 1362.21 | 680.11 | −2 | Metabolite |
| 3'N − 6 | | $A_SG_SC_M$ | 1015.19 | 506.59 | −2 | Not Observed |
| 3'N − 7 | | $A_SG_S$ | 680.15 | 339.08 | −2 | Not Observed |
| 3'N − 8 | | $A_S$ | 293.11 | 145.56 | −2 | Not Observed |
| 5'N − 1 | | $G_SC_MA_FC_FU_FU_MU_SA_S$ | 2693.26 | 1345.63 | −2 | Metabolite |
| 5'N − 2 | | $C_MA_FC_FU_FU_MU_SA_S$ | 2306.22 | 1152.11 | −2 | Metabolite |
| 5'N − 3 | | $A_FC_FU_FU_MU_SA_S$ | 1971.19 | 984.59 | −2 | Metabolite |
| 5'N − 4 | | $C_FU_FU_MU_SA_S$ | 1624.16 | 811.08 | −2 | Metabolite |
| 5'N − 5 | | $U_FU_MU_SA_S$ | 1301.15 | 649.57 | −2 | Not Observed |
| 5'N − 6 | | $U_MU_SA_S$ | 977.15 | 487.57 | −2 | Not Observed |
| 5'N − 7 | | $U_SA_S$ | 641.13 | 319.57 | −2 | Not Observed |
| 5'N − 8 | | $A_S$ | 293.11 | 145.56 | −2 | Not Observed |
| 5'N + 1 | 29 | $A_SA_SG_SC_MA_FC_FU_FU_MU_SA_S$ | 3435.35 | 1717.17 | −2 | Synthetic |

What is claimed is:
1. A modified oligonucleotide having the structure:
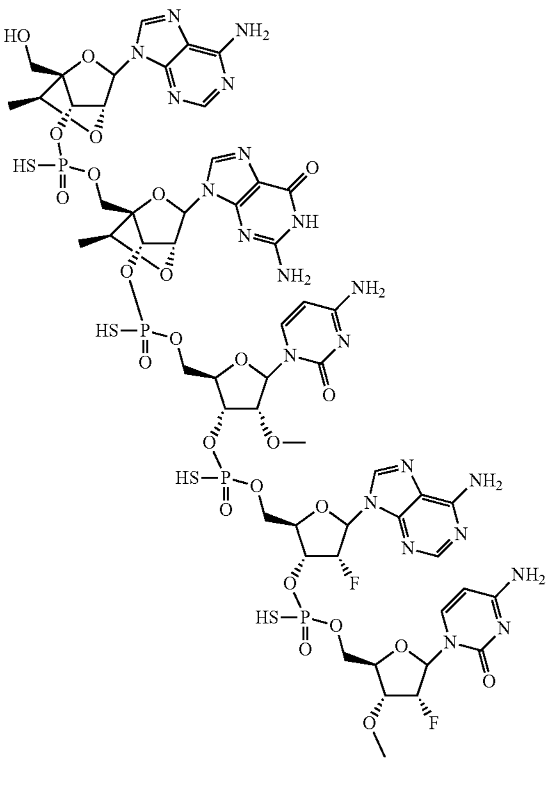
-continued
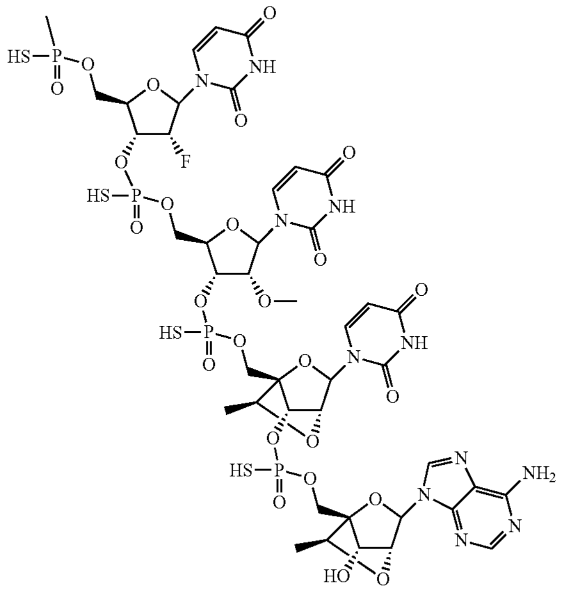
or a pharmaceutically acceptable salt thereof.
2. The modified oligonucleotide of claim 1, wherein the pharmaceutically acceptable salt is a sodium salt.
3. A modified oligonucleotide having the structure:
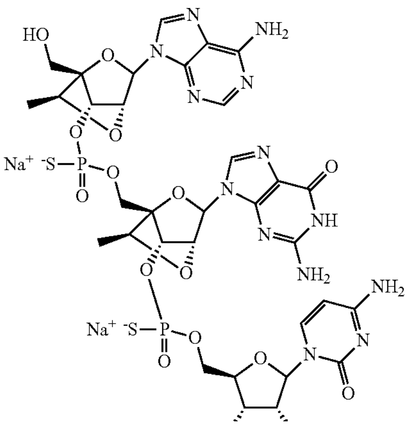

-continued

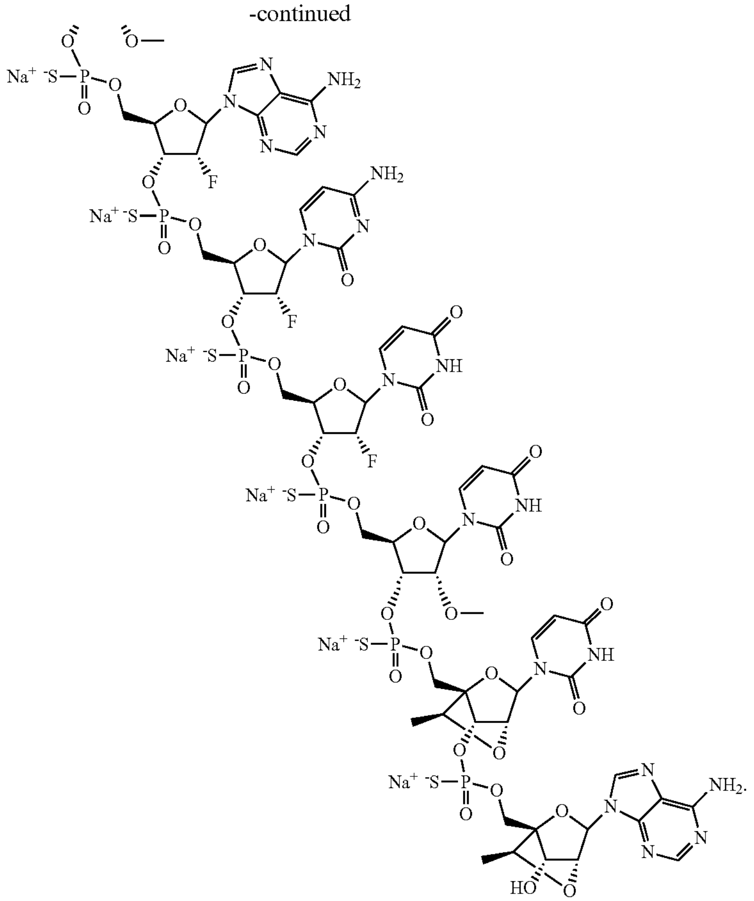

4. A pharmaceutical composition comprising the modified oligonucleotide of claim 1 and a pharmaceutically acceptable diluent.

5. The pharmaceutical composition of claim 4, wherein the pharmaceutically acceptable diluent is an aqueous solution.

6. The pharmaceutical composition of claim 5, wherein the aqueous solution is a saline solution.

7. A pharmaceutical composition comprising a modified oligonucleotide of claim 2 and a pharmaceutically acceptable diluent.

8. The pharmaceutical composition of claim 7, wherein the pharmaceutically acceptable diluent is an aqueous solution.

9. The pharmaceutical composition of claim 8, wherein the aqueous solution is a saline solution.

10. A pharmaceutical composition comprising a modified oligonucleotide of claim 3 and a pharmaceutically acceptable diluent.

11. The pharmaceutical composition of claim 10, wherein the pharmaceutically acceptable diluent is an aqueous solution.

12. The pharmaceutical composition of claim 11, wherein the aqueous solution is a saline solution.

13. A pharmaceutical composition comprising a modified oligonucleotide of claim 1, which is a lyophilized composition.

14. A pharmaceutical composition comprising a modified oligonucleotide of claim 2, which is a lyophilized composition.

15. A pharmaceutical composition comprising a modified oligonucleotide of claim 3, which is a lyophilized composition.

* * * * *